US012262890B2

(12) United States Patent
Shelton, IV et al.

(10) Patent No.: US 12,262,890 B2
(45) Date of Patent: Apr. 1, 2025

(54) ADJUSTMENT OF THE MOTOR CONTROL PROGRAM BASED ON DETECTION OF INDIVIDUAL DEVICE DRIVE TRAIN PROPERTIES

(71) Applicant: Cilag GmbH International, Zug (CH)

(72) Inventors: Frederick E. Shelton, IV, Hillsboro, OH (US); Shane R. Adams, Lebanon, OH (US); Eric B. LaFay, Madeira, OH (US); Taylor W. Aronhalt, Loveland, OH (US); Jose Luis De Cordoba Matilla, Malaga (ES); Nicholas J. Ross, Franklin, OH (US); Matthew D. Cowperthwait, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 193 days.

(21) Appl. No.: 17/957,975

(22) Filed: Sep. 30, 2022

(65) Prior Publication Data

US 2024/0108338 A1 Apr. 4, 2024

Related U.S. Application Data

(60) Provisional application No. 63/411,445, filed on Sep. 29, 2022.

(51) Int. Cl.
*A61B 17/072* (2006.01)
*A61B 17/00* (2006.01)
(Continued)

(52) U.S. Cl.
CPC ...... *A61B 17/07207* (2013.01); *A61B 17/068* (2013.01); *A61B 17/0684* (2013.01);
(Continued)

(58) Field of Classification Search
CPC ............ A61B 17/07207; A61B 17/068; A61B 17/0684; A61B 17/072; A61B 17/320092;
(Continued)

(56) References Cited

U.S. PATENT DOCUMENTS 5,403,312 A 4/1995 Yates et al.
5,817,084 A 10/1998 Jensen
(Continued)

OTHER PUBLICATIONS

"ATM-MPLS Network Interworking Version 2.0, af-aic-0178.001" ATM Standard, The ATM Forum Technical Committee, published Aug. 2003.
(Continued)

*Primary Examiner* — David Luo
(74) *Attorney, Agent, or Firm* — TROUTMAN PEPPER LOCKE LLP

(57) ABSTRACT

A surgical stapling system includes a motor, a gear reducer assembly, a drive train, and a motor controller. A method of controlling the motor includes applying a first signal to the motor, receiving drive train operational data, comparing the drive train data to baseline data, and applying a signal having a different shape than the first signal to the motor. A method of characterizing the motor includes transmitting a perturbation signal, receiving motor function parameters, determining stapler system characteristics, and adjusting a controller function. A method of controlling a stepper motor includes applying a signal to the stepper motor, receiving stepper motor operational data, comparing the data to baseline data, and adjusting the signal. Another method of controlling the motor includes receiving motor rotational data, receiving gear rotation data, calculating a mechanical transfer function, determining non-idealities of the stapling system, and modifying a control signal based on the non-idealities.

17 Claims, 26 Drawing Sheets

(51) Int. Cl.

| | | |
|---|---|---|
| *A61B 17/068* | (2006.01) | |
| *A61B 17/29* | (2006.01) | |
| *A61B 17/32* | (2006.01) | |
| *A61B 18/00* | (2006.01) | |
| *A61B 18/14* | (2006.01) | |
| *A61B 34/20* | (2016.01) | |
| *A61B 34/30* | (2016.01) | |
| *A61B 90/00* | (2016.01) | |
| *G16H 40/63* | (2018.01) | |
| *H02K 7/116* | (2006.01) | |
| *H02K 7/14* | (2006.01) | |

(52) U.S. Cl.
 CPC .... *A61B 17/072* (2013.01); *A61B 17/320092* (2013.01); *A61B 18/1445* (2013.01); *A61B 34/30* (2016.02); *G16H 40/63* (2018.01); *H02K 7/116* (2013.01); *H02K 7/145* (2013.01); *A61B 2017/00017* (2013.01); *A61B 2017/00022* (2013.01); *A61B 2017/00039* (2013.01); *A61B 2017/00075* (2013.01); *A61B 2017/00132* (2013.01); *A61B 2017/00185* (2013.01); *A61B 2017/0019* (2013.01); *A61B 2017/00221* (2013.01); *A61B 2017/00398* (2013.01); *A61B 2017/07257* (2013.01); *A61B 2017/07271* (2013.01); *A61B 2017/07278* (2013.01); *A61B 2017/07285* (2013.01); *A61B 2017/2932* (2013.01); *A61B 2017/320074* (2017.08); *A61B 2018/00642* (2013.01); *A61B 2018/0072* (2013.01); *A61B 2034/2059* (2016.02); *A61B 2090/064* (2016.02)

(58) Field of Classification Search
 CPC .... A61B 18/1445; A61B 34/30; G16H 40/63; H02K 7/116; H02K 7/145
 USPC .............................................. 318/3, 599, 560
 See application file for complete search history.

(56) References Cited

U.S. PATENT DOCUMENTS

| | | | |
|---|---|---|---|
| 5,878,193 A | 3/1999 | Wang et al. | |
| 6,132,368 A | 10/2000 | Cooper | |
| 7,000,818 B2 | 2/2006 | Shelton, IV et al. | |
| 7,422,139 B2 | 9/2008 | Shelton, IV et al. | |
| 7,464,849 B2 | 12/2008 | Shelton, IV et al. | |
| 7,524,320 B2 | 4/2009 | Tierney et al. | |
| 7,670,334 B2 | 3/2010 | Hueil et al. | |
| 7,753,245 B2 | 7/2010 | Boudreaux et al. | |
| 7,845,537 B2 | 12/2010 | Shelton, IV et al. | |
| 7,980,443 B2 | 7/2011 | Scheib et al. | |
| 8,020,743 B2* | 9/2011 | Shelton, IV | A61B 17/07207 227/19 |
| 8,210,411 B2* | 7/2012 | Yates | A61B 17/3205 227/19 |
| 8,220,688 B2 | 7/2012 | Laurent et al. | |
| 8,308,040 B2 | 11/2012 | Huang et al. | |
| 8,393,514 B2 | 3/2013 | Shelton, IV et al. | |
| 8,505,802 B2 | 8/2013 | Viola et al. | |
| 8,561,870 B2 | 10/2013 | Baxter, III et al. | |
| 8,608,045 B2 | 12/2013 | Smith et al. | |
| 8,685,004 B2 | 4/2014 | Zemlock et al. | |
| 8,733,613 B2 | 5/2014 | Huitema et al. | |
| 8,901,779 B2* | 12/2014 | Kesler | H02J 7/00309 307/104 |
| 9,016,540 B2 | 4/2015 | Whitman et al. | |
| 9,050,083 B2 | 6/2015 | Yates et al. | |
| 9,072,535 B2 | 7/2015 | Shelton, IV et al. | |
| 9,101,358 B2 | 8/2015 | Kerr et al. | |
| 9,345,481 B2 | 5/2016 | Hall et al. | |
| 9,804,618 B2 | 10/2017 | Leimbach et al. | |
| 9,808,246 B2 | 11/2017 | Shelton, IV et al. | |
| 9,913,642 B2 | 3/2018 | Leimbach et al. | |
| 9,987,095 B2 | 6/2018 | Chowaniec et al. | |
| 9,999,472 B2 | 6/2018 | Weir et al. | |
| 10,159,483 B2 | 12/2018 | Beckman et al. | |
| 10,368,865 B2 | 8/2019 | Harris et al. | |
| 10,448,948 B2 | 10/2019 | Shelton, IV et al. | |
| 10,639,037 B2 | 5/2020 | Shelton, IV et al. | |
| 10,646,220 B2 | 5/2020 | Shelton, IV et al. | |
| 10,695,057 B2 | 6/2020 | Shelton, IV et al. | |
| 10,716,565 B2 | 7/2020 | Shelton, IV et al. | |
| 10,758,226 B2 | 9/2020 | Weir et al. | |
| 10,828,028 B2 | 11/2020 | Harris et al. | |
| 10,835,245 B2 | 11/2020 | Swayze et al. | |
| 10,842,523 B2 | 11/2020 | Shelton, IV et al. | |
| 10,863,986 B2* | 12/2020 | Yates | A61B 17/00 |
| 10,881,399 B2 | 1/2021 | Shelton, IV et al. | |
| 10,888,321 B2 | 1/2021 | Shelton, IV et al. | |
| 10,973,519 B2 | 4/2021 | Weir et al. | |
| 11,324,501 B2 | 5/2022 | Shelton, IV et al. | |
| 11,369,366 B2 | 6/2022 | Scheib et al. | |
| 11,382,704 B2 | 7/2022 | Overmyer et al. | |
| 11,419,630 B2 | 8/2022 | Yates et al. | |
| 11,628,006 B2 | 4/2023 | Henderson et al. | |
| 11,791,759 B2* | 10/2023 | Combes | H02M 7/5395 318/811 |
| 2007/0175955 A1 | 8/2007 | Shelton et al. | |
| 2014/0263541 A1 | 9/2014 | Leimbach et al. | |
| 2014/0263552 A1 | 9/2014 | Hall et al. | |
| 2017/0079642 A1 | 3/2017 | Overmyer et al. | |
| 2019/0200981 A1 | 7/2019 | Harris et al. | |
| 2019/0201027 A1 | 7/2019 | Shelton, IV et al. | |
| 2020/0345356 A1 | 11/2020 | Leimbach et al. | |
| 2021/0244407 A1 | 8/2021 | Shelton, IV et al. | |

OTHER PUBLICATIONS

IEEE Std 802.3-2012 (Revision of IEEE Std 802.3-2008, published Dec. 28, 2012.

* cited by examiner

ADJUSTMENT OF THE MOTOR CONTROL PROGRAM BASED ON DETECTION OF INDIVIDUAL DEVICE DRIVE TRAIN PROPERTIES

CROSS-REFERENCE TO RELATED APPLICATIONS

This application claims the benefit under 35 U.S.C. § 119(e) to U.S. Provisional Patent Application Ser. No. 63/411,445, titled METHOD FOR CONTROLLING SURGICAL SYSTEM DURING TISSUE TREATMENT MOTION, filed Sep. 29, 2022, the disclosure of which is herein incorporated by reference in its entirety.

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
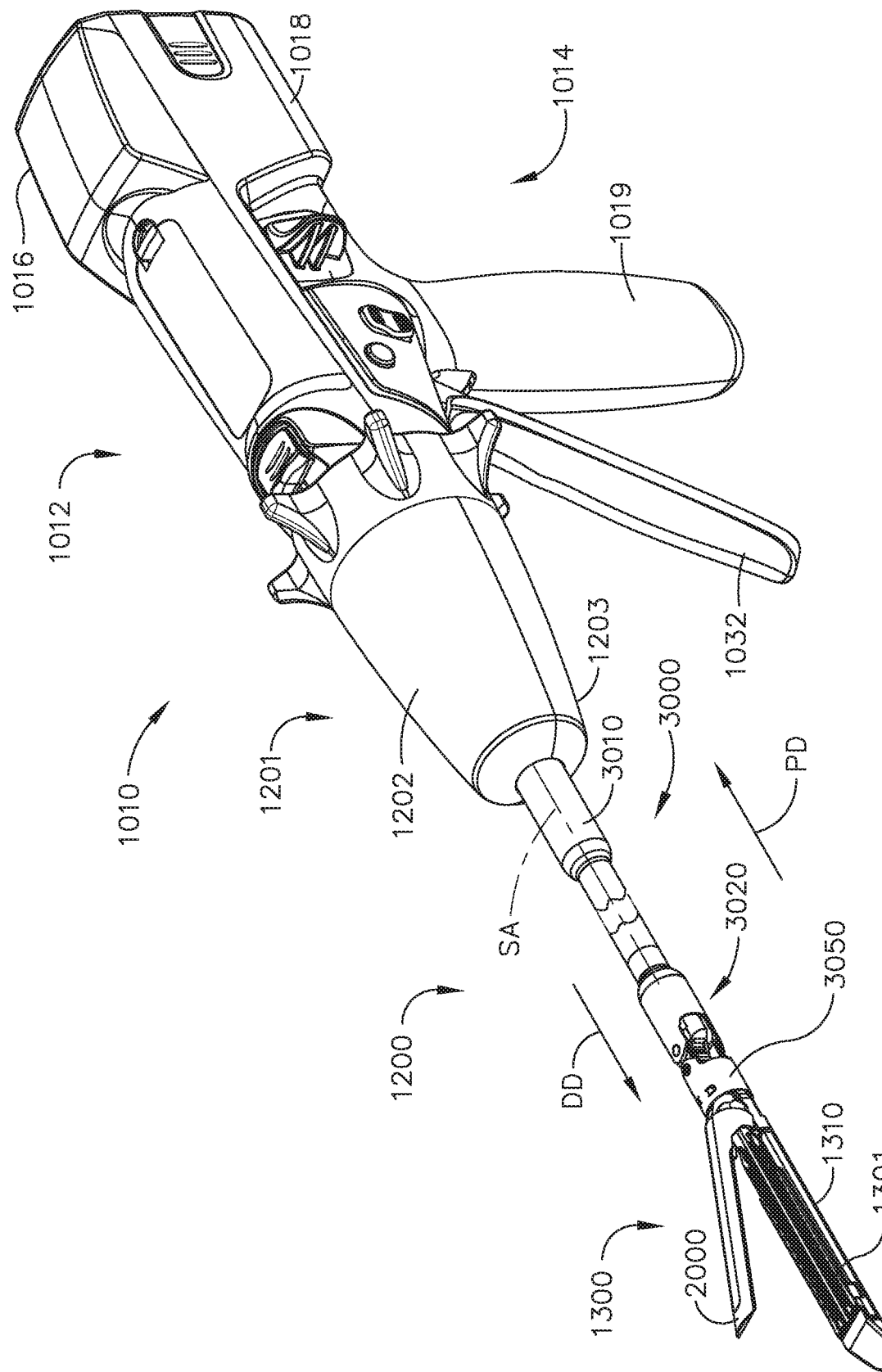
FIG. 1 is a perspective view of a powered surgical stapling system.

Applicant of the present application owns the following U.S. patent applications that were filed on Sep. 30, 2022 and which are each herein incorporated by reference in their respective entireties:

U.S. patent application Ser. No. 17/957,917, titled METHOD FOR CONTROLLING SURGICAL SYSTEM DURING TISSUE TREATMENT MOTION; published as U.S. Patent Application Publication No. 2024/0108334;

U.S. patent application Ser. No. 17/957,923, titled ADAPTING TISSUE TREATMENT MOTION PARAMETERS BASED ON SITUATIONAL PARAMETERS; published as U.S. Patent Application Publication No. 2024/0108331;

U.S. patent application Ser. No. 17/957,933, titled ADAPTIVE FIRING CONTROL ALGORITHM BASED ON MECHANICAL ACTUATION OF USER CONTROLS; published as U.S. Patent Application Publication No. 2024/0108335;

U.S. patent application Ser. No. 17/957,946, titled ADAPTATION OF INDEPENDENT FIRING AND CLOSURE POWERED STAPLING SYSTEMS; published as U.S. Patent Application Publication No. 2024/0108336;

U.S. patent application Ser. No. 17/957,954, titled MONITORING ONE DRIVE SYSTEM TO ADAPT THE MOTOR DRIVEN ASPECT OF A SECOND DRIVE SYSTEM; published as U.S. Patent Application Publication No. 2024/0108337;

U.S. patent application Ser. No. 17/957,984, titled ADJUSTMENT OF A MOTOR CONTROL COMMAND SIGNAL TO ADAPT TO SYSTEM CHANGES; published as U.S. Patent Application Publication No. 2024/0108339;

U.S. patent application Ser. No. 17/957,990, titled MOTOR ADJUSTMENTS IN ABSENCE OF MOTOR DRIVE SIGNAL; patented as U.S. Pat. No. 11,974,825;

U.S. patent application Ser. No. 17/957,995, titled SURGICAL SYSTEMS WITH SYNCHRONIZED DISTRIBUTED PROCESSING CAPABILITIES; published as U.S. Patent Application Publication No. 2024/0112798;

U.S. patent application Ser. No. 17/958,001, titled SURGICAL SYSTEM WITH MOTOR RELATIVE CAPACITY INTERROGATIONS; published as U.S. Patent Application Publication No. 2024/0108333;

U.S. patent application Ser. No. 17/958,008, titled MOTOR CONTROL OF SURGICAL INSTRUMENT SYSTEMS; published as U.S. Patent Application Publication No. 2024/0108329;

U.S. patent application Ser. No. 17/958,013, titled SURGICAL SYSTEM WITH AMPLITUDE AND PULSE WIDTH MODULATION ADJUSTMENTS; published as U.S. Patent Application Publication No. 2024/0108421;

U.S. patent application Ser. No. 17/958,024, titled SURGICAL ALGORITHMS WITH INCREMENTAL SENSORY ACTIONS; published as U.S. Patent Application Publication No. 2024/0108340;

U.S. patent application Ser. No. 17/958,028, titled UTILIZING LOCAL FIRING PARAMETERS TO INITIATE MOTOR CONTROL ADJUSTMENTS IN SURGICAL SYSTEMS; published as U.S. Patent Application Publication No. 2024/0108341; and U.S. patent application Ser. No. 17/958,037, titled SURGICAL SYSTEMS WITH DYNAMIC FORCE TO FIRE ADJUSTMENTS; published as U.S. Patent Application Publication No. 2024/0108342.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Figure 2:
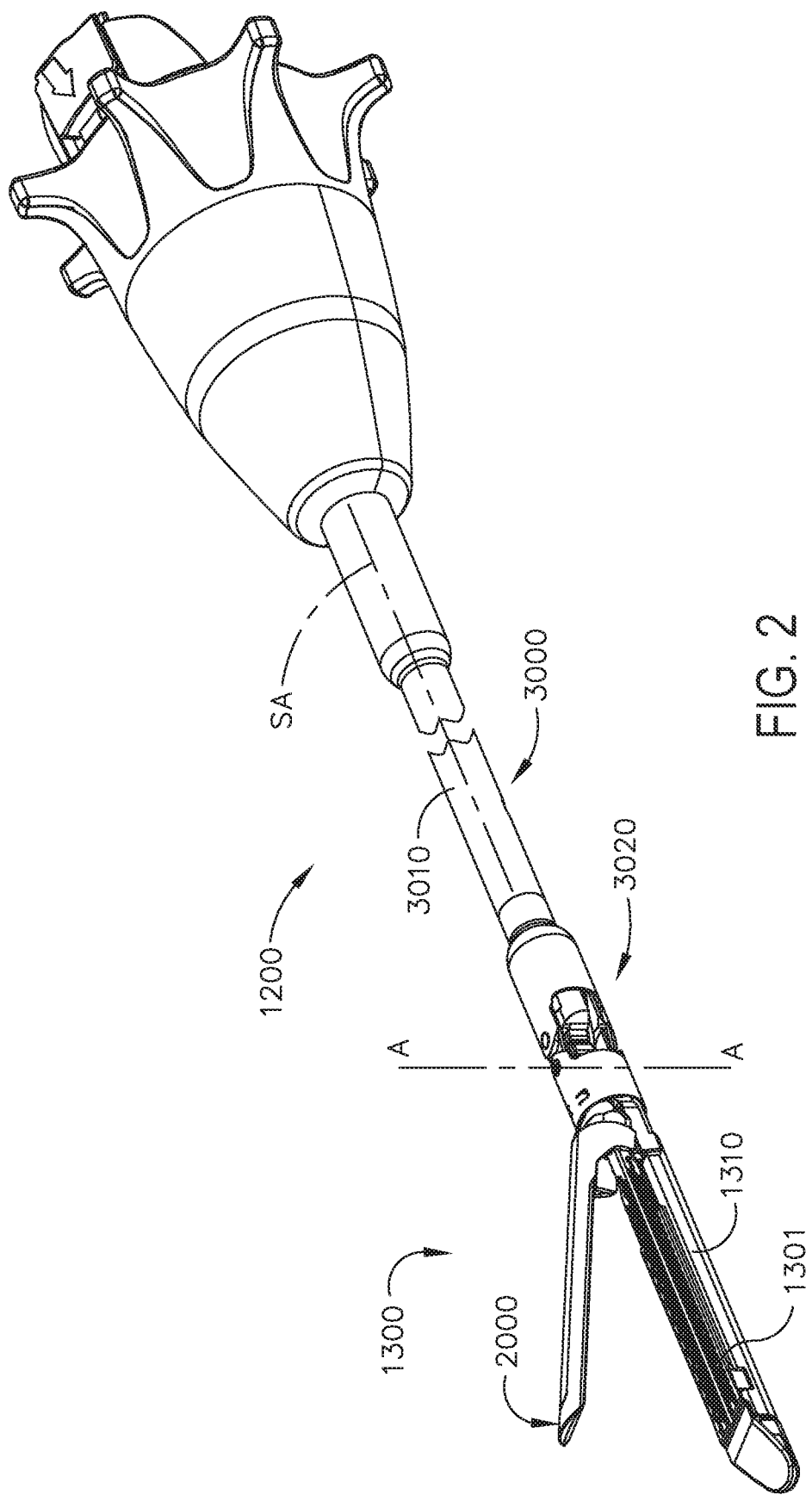
FIG. 2 is a perspective view of an interchangeable surgical shaft assembly of the powered surgical stapling system of FIG. 1.
Figure 3:
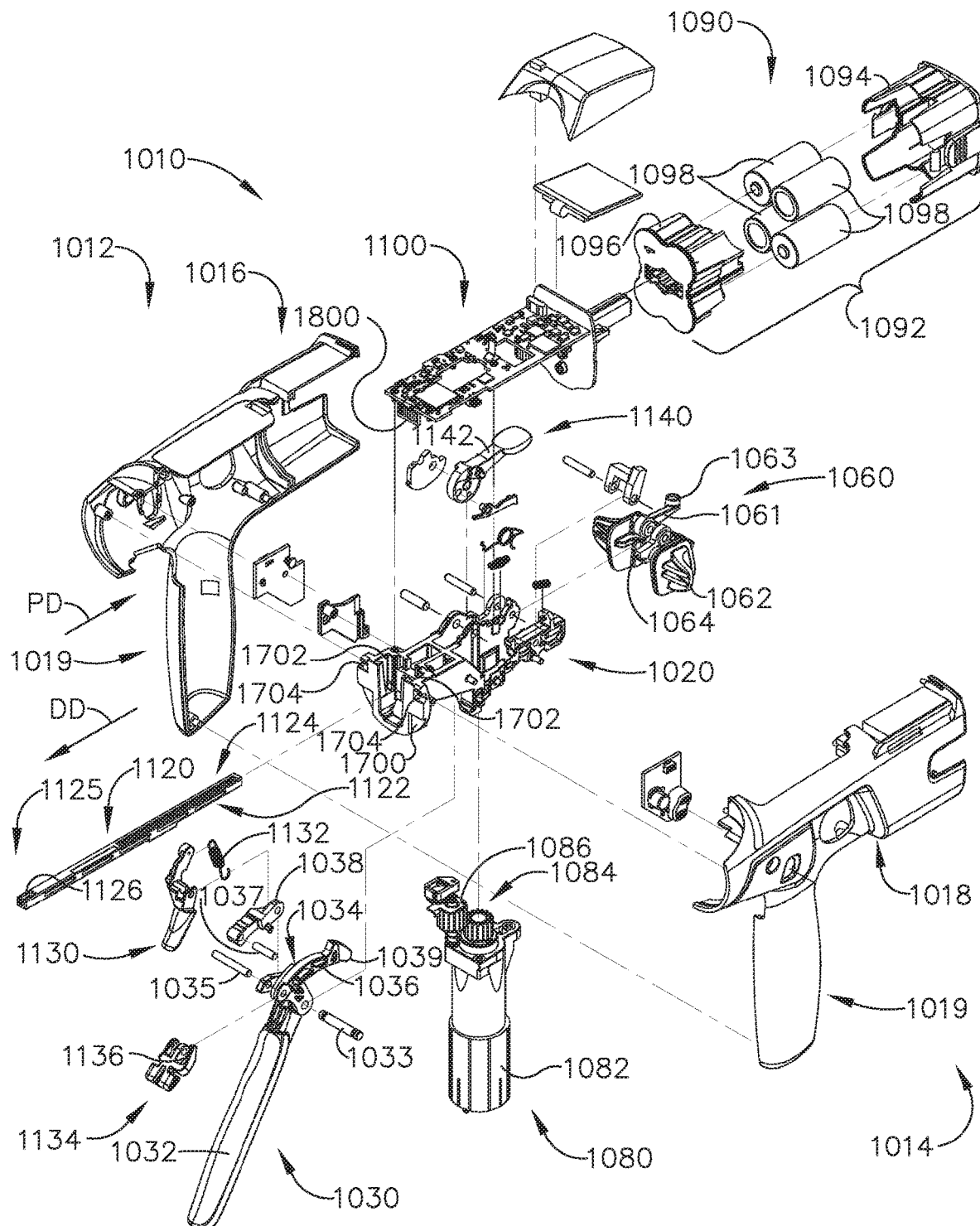
FIG. 3 is an exploded assembly view of portions of a handle assembly of the powered surgical stapling system of FIG. 1.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife, FIG. 1 illustrates the surgical instrument 1010 that includes an interchangeable shaft assembly 1200 operably coupled to a housing 1012. FIG. 2 illustrates the interchangeable shaft assembly 1200 detached from the housing 1012 or handle 1014. As can be seen in FIG. 3, the handle 1014 may comprise a pair of interconnectable handle housing segments 1016 and 1018 that may be interconnected by screws, snap features, adhesive, etc. In the illustrated arrangement, the handle housing segments 1016, 1018 cooperate to form a pistol grip portion 1019. FIGS. 1 and 3 depict a motor-driven surgical cutting and fastening instrument 1010 that may or may not be reused. In the illustrated embodiment, the instrument 1010 includes a proximal housing 1012 that comprises a handle 1014 that is configured to be grasped, manipulated and actuated by the clinician. The housing 1012 is configured for operable attachment to an interchangeable shaft assembly 1200 that has a surgical end effector 1300 operably coupled thereto that is configured to perform one or more surgical tasks or procedures. As the present Detailed Description proceeds, it will be understood that the various forms of interchangeable shaft assemblies disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the interchangeable shaft assemblies disclosed herein and their respective equivalents. In addition, various components may be "housed" or contained in the housing or various components may be "associated with" a housing. In such instances, the components may not be contained within the housing or supported directly by the housing. The term "frame" may refer to a portion of a handheld surgical instrument. The term "frame" may also represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, that is incorporated by reference herein in its entirety.

The proximal housing 1012 depicted in FIG. 1 is shown in connection with an interchangeable shaft assembly 1200 (FIGS. 2, 4 and 5) that includes an end effector 1300 that comprises a surgical cutting and fastening device that is configured to operably support a surgical staple cartridge 1301 therein. The housing 1012 may be configured for use in connection with interchangeable shaft assemblies that include end effectors that are adapted to support different sizes and types of staple cartridges, have different shaft lengths, sizes, and types, etc. In addition, the housing 1012 may also be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener that can be gripped and manipulated by the clinician. As will be discussed in further detail below, the handle 1014 operably supports a plurality of drive systems therein that are configured to generate and apply various control motions to corresponding portions of the interchangeable shaft assembly that is operably attached thereto.

Referring now to FIG. 3, the handle 1014 may further include a frame 1020 that operably supports a plurality of drive systems. For example, the frame 1020 can operably support a "first" or closure drive system, generally designated as 1030, which may be employed to apply closing and opening motions to the interchangeable shaft assembly 1200 that is operably attached or coupled thereto. In at least one form, the closure drive system 1030 may include an actuator in the form of a closure trigger 1032 that is pivotally supported by the frame 1020. More specifically, as illustrated in FIG. 3, the closure trigger 1032 is pivotally coupled to the handle 1014 by a pin 1033. Such arrangement enables the closure trigger 1032 to be manipulated by a clinician such that when the clinician grips the pistol grip portion 1019 of the handle 1014, the closure trigger 1032 may be easily pivoted from a starting or "unactuated" position to an "actuated" position and more particularly to a fully compressed or fully actuated position. The closure trigger 1032 may be biased into the unactuated position by spring or other biasing arrangement (not shown). In various forms, the closure drive system 1030 further includes a closure linkage assembly 1034 that is pivotally coupled to the closure trigger 1032. As can be seen in FIG. 3, the closure linkage assembly 1034 may include a first closure link 1036 and a second closure link 1038 that are pivotally coupled to the closure trigger 1032 by a pin 1035. The second closure link 1038 may also be referred to herein as an "attachment member" and include a transverse attachment pin 1037.

Still referring to FIG. 3, it can be observed that the first closure link 1036 may have a locking wall or end 1039 thereon that is configured to cooperate with a closure release assembly 1060 that is pivotally coupled to the frame 1020. In at least one form, the closure release assembly 1060 may comprise a release button assembly 1062 that has a distally protruding locking pawl 1064 formed thereon. The release button assembly 1062 may be pivoted in a counterclockwise direction by a release spring (not shown). As the clinician depresses the closure trigger 1032 from its unactuated position towards the pistol grip portion 1019 of the handle 1014, the first closure link 1036 pivots upward to a point wherein the locking pawl 1064 drops into retaining engagement with the locking wall 1039 on the first closure link 1036 thereby preventing the closure trigger 1032 from returning to the unactuated position. Thus, the closure release assembly 1060 serves to lock the closure trigger 1032 in the fully actuated position. When the clinician desires to unlock the closure trigger 1032 to permit it to be biased to the unactuated position, the clinician simply pivots the closure release button assembly 1062 such that the locking pawl 1064 is moved out of engagement with the locking wall 1039 on the first closure link 1036. When the locking pawl 1064 has been moved out of engagement with the first closure link 1036, the closure trigger 1032 may pivot back to the unactuated position. Other closure trigger locking and release arrangements may also be employed.

An arm 1061 may extend from the closure release button assembly 1062. A magnetic element 1063, such as a permanent magnet, for example, may be mounted to the arm 1061. When the closure release button assembly 1062 is rotated from its first position to its second position, the magnetic element 1063 can move toward a circuit board 1100. The circuit board 1100 can include at least one sensor that is configured to detect the movement of the magnetic element 1063. In at least one embodiment, for example, a "Hall Effect" sensor (not shown) can be mounted to the bottom surface of the circuit board 1100. The Hall Effect sensor can be configured to detect changes in a magnetic field surrounding the Hall Effect sensor caused by the movement of the magnetic element 1063. The Hall Effect sensor can be in signal communication with a microcontroller, for example, which can determine whether the closure release button assembly 1062 is in its first position, which is associated with the unactuated position of the closure trigger 1032 and the open configuration of the end effector, its second position, which is associated with the actuated position of the closure trigger 1032 and the closed configuration of the end effector, and/or any position between the first position and the second position.

In at least one form, the handle 1014 and the frame 1020 may operably support another drive system referred to herein as a firing drive system 1080 that is configured to apply firing motions to corresponding portions of the interchangeable shaft assembly attached thereto. The firing drive system 1080 may also be referred to herein as a "second drive system". The firing drive system 1080 may employ an electric motor 1082 that is located in the pistol grip portion 1019 of the handle 1014. In various forms, the motor 1082 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 1082 may be powered by a power source 1090 that in one form may comprise a removable power pack 1092. As can be seen in FIG. 3, for example, the power pack 1092 may comprise a proximal housing portion 1094 that is configured for attachment to a distal housing portion 1096. The proximal housing portion 1094 and the distal housing portion 1096 are configured to operably support a plurality of batteries 1098 therein. Batteries 1098 may each comprise, for example, a Lithium Ion ("LI") or other suitable battery. The distal housing portion 1096 is configured for removable operable attachment to the circuit board 1100 which is also operably coupled to the motor 1082. A number of batteries 1098 may be connected in series may be used as the power source for the surgical instrument 1010. In addition, the power source 1090 may be replaceable and/or rechargeable.

As outlined above with respect to other various forms, the electric motor 1082 can include a rotatable shaft (not shown) that operably interfaces with a gear reducer assembly 1084 that is mounted in meshing engagement with a set, or rack, of drive teeth 1122 on a longitudinally movable drive member 1120. In use, a voltage polarity provided by the power source 1090 can operate the electric motor 1082 in a clockwise direction wherein the voltage polarity applied to the electric motor by the battery can be reversed in order to operate the electric motor 1082 in a counter-clockwise direction. When the electric motor 1082 is rotated in one direction, the drive member 1120 will be axially driven in the distal direction "DD". When the motor 1082 is driven in the opposite rotary direction, the drive member 1120 will be axially driven in a proximal direction "PD". The handle 1014 can include a switch which can be configured to reverse the polarity applied to the electric motor 1082 by the power source 1090. As with the other forms described herein, the handle 1014 can also include a sensor that is configured to detect the position of the drive member 1120 and/or the direction in which the drive member 1120 is being moved.

Actuation of the motor 1082 can be controlled by a firing trigger 1130 that is pivotally supported on the handle 1014. The firing trigger 1130 may be pivoted between an unactuated position and an actuated position. The firing trigger 1130 may be biased into the unactuated position by a spring 1132 or other biasing arrangement such that when the clinician releases the firing trigger 1130, it may be pivoted or otherwise returned to the unactuated position by the spring 1132 or biasing arrangement. In at least one form, the firing trigger 1130 can be positioned "outboard" of the closure trigger 1032 as was discussed above. In at least one form, a firing trigger safety button 1134 may be pivotally mounted to the closure trigger 1032 by the pin 1035. The safety button 1134 may be positioned between the firing trigger 1130 and the closure trigger 1032 and have a pivot arm 1136 protruding therefrom. When the closure trigger 1032 is in the unactuated position, the safety button 1134 is contained in the handle 1014 where the clinician cannot readily access it and move it between a safety position preventing actuation of the firing trigger 1130 and a firing position wherein the firing trigger 1130 may be fired. As the clinician depresses the closure trigger 1032, the safety button 1134 and the firing trigger 1130 pivot down wherein they can then be manipulated by the clinician.

As indicated above, in at least one form, the longitudinally movable drive member 1120 has a rack of teeth 1122 formed thereon for meshing engagement with a corresponding drive gear 1086 of the gear reducer assembly 1084. At least one form also includes a manually-actuatable "bailout" assembly 1140 that is configured to enable the clinician to manually retract the longitudinally movable drive member 1120 should the motor 1082 become disabled. The bailout assembly 1140 may include a lever or bailout handle assembly 1142 that is configured to be manually pivoted into ratcheting engagement with teeth 1124 also provided in the drive member 1120. Thus, the clinician can manually retract the drive member 1120 by using the bailout handle assembly 1142 to ratchet the drive member 1120 in the proximal direction "PD". U.S. Pat. No. 8,608,045, entitled POWERED SURGICAL CUTTING AND STAPLING APPARATUS WITH MANUALLY RETRACTABLE FIRING SYSTEM, discloses bailout arrangements and other components, arrangements and systems that may also be employed with the various instruments disclosed herein. U.S. Pat. No. 8,608,045, is hereby incorporated by reference herein in its entirety.

Figure 4:
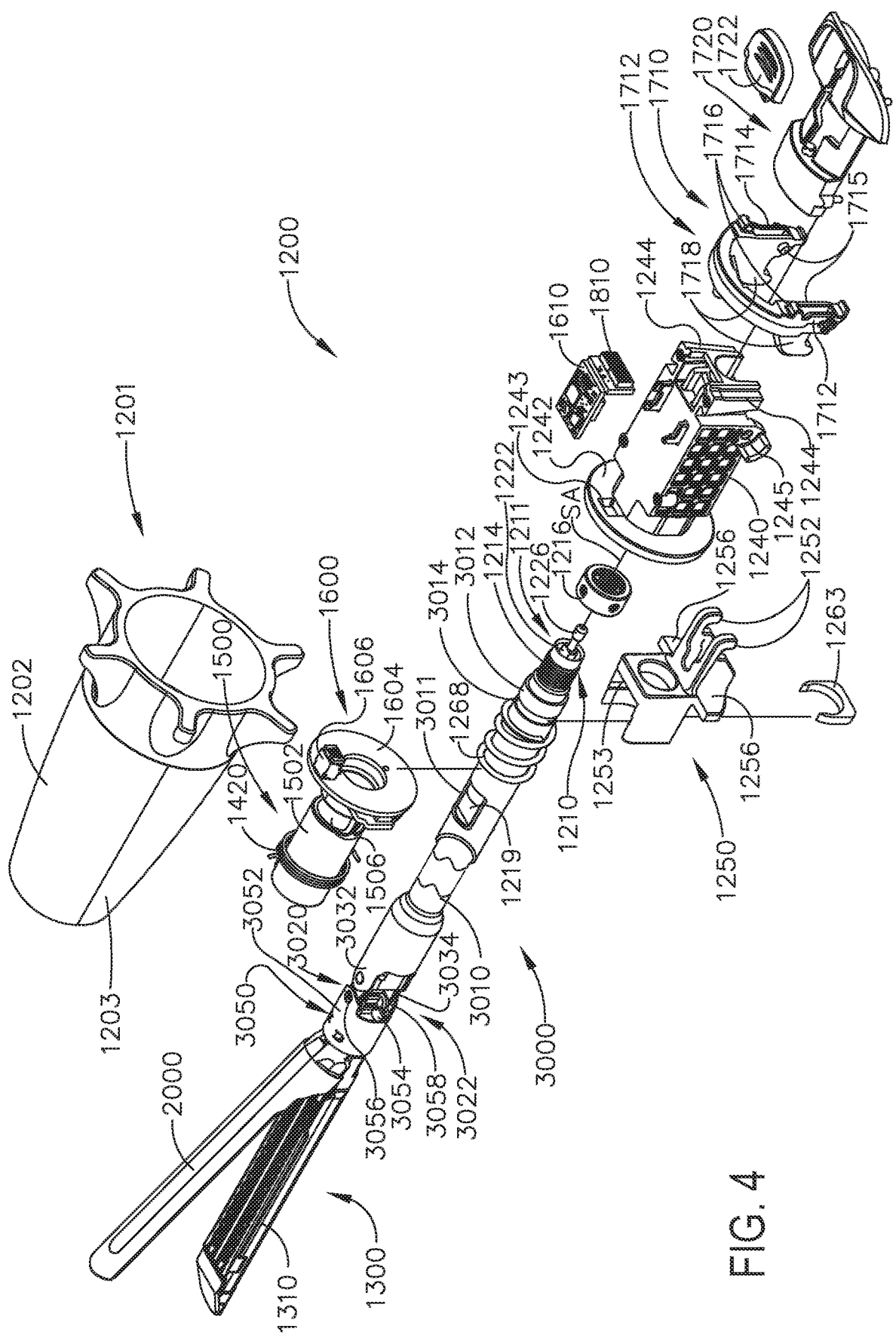
FIG. 4 is an exploded assembly view of the interchangeable surgical shaft assembly of FIG. 2.
Figure 5:
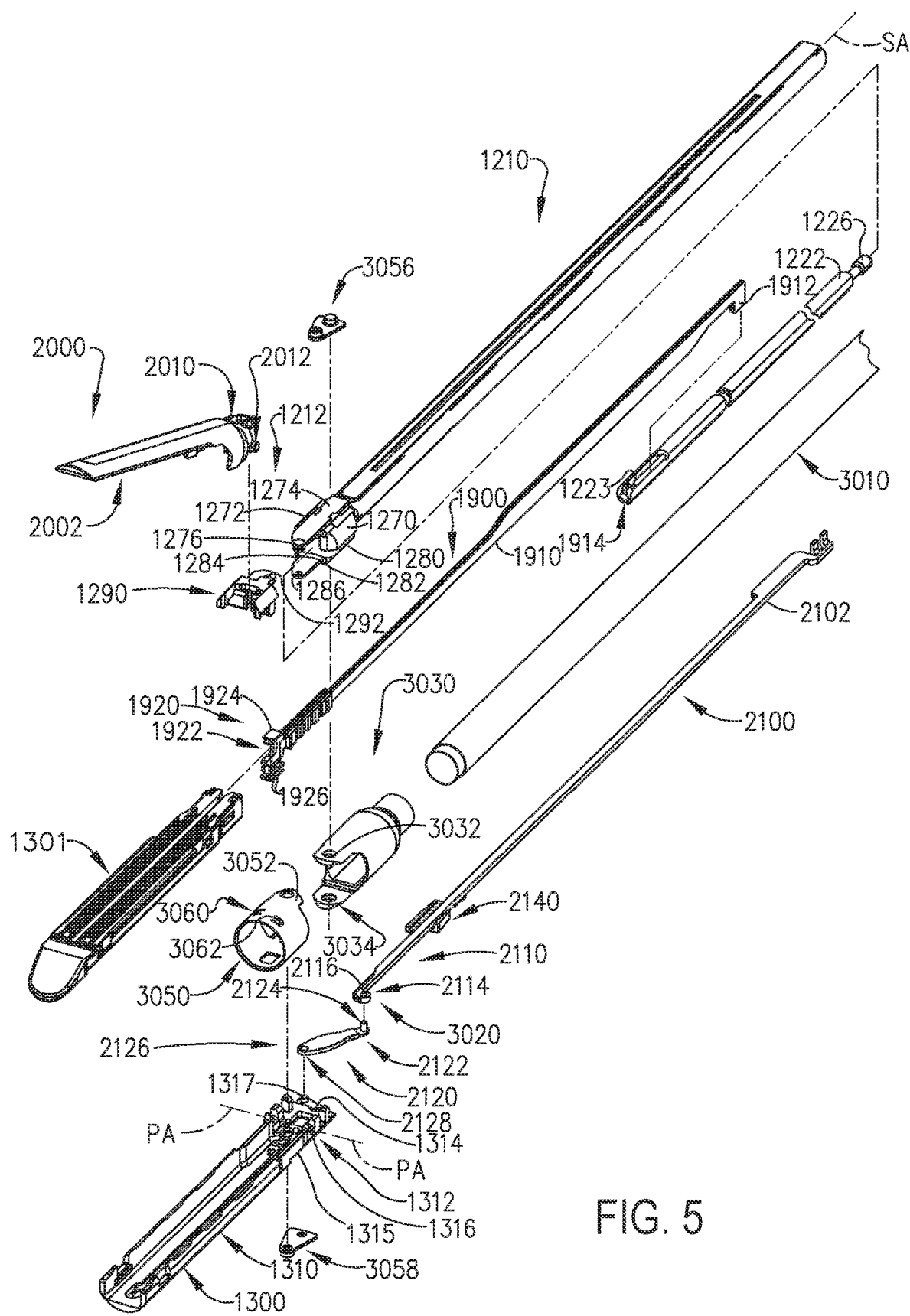
FIG. 5 is another partial exploded assembly view of a portion of the interchangeable surgical shaft assembly of FIG. 4.

Turning now to FIGS. 2 and 5, the interchangeable shaft assembly 1200 includes a surgical end effector 1300 that comprises an elongate channel 1310 that is configured to operably support a staple cartridge 1301 therein. The end effector 1300 may further include an anvil 2000 that is pivotally supported relative to the elongate channel 1310. The interchangeable shaft assembly 1200 may further include an articulation joint 3020 and an articulation lock 2140 which can be configured to releasably hold the end effector 1300 in a desired position relative to a shaft axis SA. Examples of various features of at least one form of the end effector 1300, the articulation joint 3020 and articulation locks may be found in U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541. The entire disclosure of U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541, is hereby incorporated by reference herein. As can be seen in FIG. 4, the interchangeable shaft assembly 1200 can further include a proximal housing or nozzle 1201 comprised of nozzle portions 1202 and 1203.

The interchangeable shaft assembly 1200 can further include a closure system or closure member assembly 3000 which can be utilized to close and/or open the anvil 2000 of the end effector 1300. The shaft assembly 1200 can include a spine 1210 that is configured to, one, slidably support a firing member therein and, two, slidably support the closure member assembly 3000 which extends around the spine 1210. As can be seen in FIG. 5, a distal end 1212 of spine 1210 terminates in an upper lug mount feature 1270 and in a lower lug mount feature 1280. The upper lug mount feature 1270 is formed with a lug slot 1272 therein that is adapted to mountingly support an upper mounting link 1274 therein. Similarly, the lower lug mount feature 1280 is formed with a lug slot 1282 therein that is adapted to mountingly support a lower mounting link 1284 therein. The upper mounting link 1274 includes a pivot socket 1276 therein that is adapted to rotatably receive therein a pivot pin 1292 that is formed on a channel cap or anvil retainer 1290 that is attached to a proximal end portion 1312 of the elongate channel 1310. The lower mounting link 1284 includes lower pivot pin 1286 that adapted to be received within a pivot hole 1314 formed in the proximal end portion 1312 of the elongate channel 1310. See FIG. 5. The lower pivot pin 1286 is vertically aligned with the pivot socket 1276 to define an articulation axis AA about which the surgical end effector 1300 may articulate relative to the shaft axis SA. See FIG. 2.

In the illustrated example, the surgical end effector 1300 is selectively articulatable about the articulation axis AA by an articulation system 2100. In one form, the articulation system 2100 includes proximal articulation driver 2102 that is pivotally coupled to an articulation link 2120. As can be most particularly seen in FIG. 5, an offset attachment lug 2114 is formed on a distal end 2110 of the proximal articulation driver 2102. A pivot hole 2116 is formed in the offset attachment lug 2114 and is configured to pivotally receive therein a proximal link pin 2124 formed on the proximal end 2122 of the articulation link 2120. A distal end 2126 of the articulation link 2120 includes a pivot hole 2128 that is configured to pivotally receive therein a channel pin 1317 formed on the proximal end portion 1312 of the elongate channel 1310. Thus, axial movement of proximal articulation driver 2102 will thereby apply articulation motions to the elongate channel 1310 to thereby cause the surgical end effector 1300 to articulate about the articulation axis AA relative to the spine 1210. Further details concerning the construction and operation of the articulation system 2100 may be found in various references incorporated by reference herein including U.S. patent application Ser. No. 15/635,631, filed Jun. 28, 2017, entitled SURGICAL INSTRUMENT WITH AXIALLY MOVABLE CLOSURE MEMBER, now U.S.

Patent Application Publication No. 2019/0000464, the entire disclosure of which is hereby incorporated by reference herein. In various circumstances, the proximal articulation driver 2102 can be held in position by an articulation lock 2140 when the proximal articulation driver 2102 is not being moved in the proximal or distal directions. Additional details regarding an example of an articulation lock 2140 may be found in U.S. patent application Ser. No. 15/635,631, now U.S. Patent Application Publication No. 2019/0000464, as well as in other references incorporated by reference herein.

In various circumstances, the spine 1210 can comprise a proximal end 1211 which is rotatably supported in a chassis 1240. In one arrangement, for example, the proximal end 1211 of the spine 1210 has a thread 1214 formed thereon for threaded attachment to a spine bearing 1216 configured to be supported within the chassis 1240. See FIG. 4. Such an arrangement facilitates rotatable attachment of the spine 1210 to the chassis 1240 such that the spine 1210 may be selectively rotated about a shaft axis SA relative to the chassis 1240.

Referring primarily to FIG. 4, the interchangeable shaft assembly 1200 includes a closure shuttle 1250 that is slidably supported within the chassis 1240 such that it may be axially moved relative thereto. The closure shuttle 1250 includes a pair of proximally-protruding hooks 1252 that are configured for attachment to the attachment pin 1037 (FIG. 3) that is attached to the second closure link 1038 as will be discussed in further detail below. In at least one example, the closure member assembly 3000 comprises a proximal closure member segment 3010 that has a proximal end 3012 that is coupled to the closure shuttle 1250 for relative rotation thereto. For example, a U shaped connector 1263 is inserted into an annular slot 3014 in the proximal end 3012 of the proximal closure member segment 3010 and is retained within vertical slots 1253 in the closure shuttle 1250. Such an arrangement serves to attach the proximal closure member segment 3010 to the closure shuttle 1250 for axial travel therewith while enabling the proximal closure member segment 3010 to rotate relative to the closure shuttle 1250 about the shaft axis SA. A closure spring 1268 is journaled on the proximal closure member segment 3010 and serves to bias the proximal closure member segment 3010 in the proximal direction "PD" which can serve to pivot the closure trigger 1032 into the unactuated position when the shaft assembly is operably coupled to the handle 1014.

In at least one form, the interchangeable shaft assembly 1200 may further include an articulation joint 3020. Other interchangeable shaft assemblies, however, may not be capable of articulation. As can be seen in FIG. 5, for example, a distal closure member or distal closure tube segment 3030 is coupled to the distal end of the proximal closure member segment 3010. The articulation joint 3020 includes a double pivot closure sleeve assembly 3022. According to various forms, the double pivot closure sleeve assembly 3022 includes an end effector closure tube 3050 having upper and lower distally projecting tangs 3052, 3054. An upper double pivot link 3056 includes upwardly projecting distal and proximal pivot pins that engage respectively an upper distal pin hole in the upper proximally projecting tang 3052 and an upper proximal pin hole in an upper distally projecting tang 3032 on the distal closure tube segment 3030. A lower double pivot link 3058 includes upwardly projecting distal and proximal pivot pins that engage respectively a lower distal pin hole in the lower proximally projecting tang 3054 and a lower proximal pin hole in the lower distally projecting tang 3034. See FIGS. 4 and 5. As will be discussed in further detail below, the closure member assembly 3000 is translated distally (direction "DD") to close the anvil 2000, for example, in response to the actuation of the closure trigger 1032. The anvil 2000 is opened by proximally translating the closure member assembly 3000 which causes the end effector closure sleeve to interact with the anvil 2000 and pivot it to an open position.

As was also indicated above, the interchangeable shaft assembly 1200 further includes a firing member 1900 that is supported for axial travel within the spine 1210. The firing member 1900 includes an intermediate firing shaft portion 1222 that is configured for attachment to a distal cutting portion or knife bar 1910. The intermediate firing shaft portion 1222 may include a longitudinal slot 1223 in the distal end thereof which can be configured to receive a tab 1912 on the proximal end of the distal knife bar 1910. The longitudinal slot 1223 and the proximal end tab 1912 can be sized and configured to permit relative movement therebetween and can comprise a slip joint 1914. The slip joint 1914 can permit the intermediate firing shaft portion 1222 of the firing member 1900 to be moved to articulate the end effector 1300 without moving, or at least substantially moving, the knife bar 1910. Once the end effector 1300 has been suitably oriented, the intermediate firing shaft portion 1222 can be advanced distally until a proximal sidewall of the longitudinal slot 1223 comes into contact with the tab 1912 in order to advance the knife bar 1910 and fire the staple cartridge 1301 positioned within the channel 1310. The knife bar 1910 includes a knife portion 1920 that includes a blade or tissue cutting edge 1922 and includes an upper anvil engagement tab 1924 and lower channel engagement tabs 1926. Various firing member configurations and operations are disclosed in various other references incorporated herein by reference.

Embodiments are also envisioned where, in lieu of a slip joint 1914, a shifter assembly can be used. Details of such a shifter assembly and corresponding components, assemblies, and systems can be found in U.S. patent application Ser. No. 15/635,521, entitled SURGICAL INSTRUMENT LOCKOUT ARRANGEMENT, which is incorporated by reference herein in its entirety.

As can be seen in FIG. 4, the shaft assembly 1200 further includes a switch drum 1500 that is rotatably received on proximal closure member segment 3010. The switch drum 1500 comprises a hollow shaft segment 1502 that has a shaft boss formed thereon for receiving an outwardly protruding actuation pin therein. In various circumstances, the actuation pin extends through a longitudinal slot provided in the lock sleeve to facilitate axial movement of the lock sleeve when it is engaged with the articulation driver. A rotary torsion spring 1420 is configured to engage the boss on the switch drum 1500 and a portion of the nozzle housing 1203 to apply a biasing force to the switch drum 1500. The switch drum 1500 can further comprise at least partially circumferential openings 1506 defined therein which can be configured to receive circumferential mounts extending from the nozzle portions 1202, 1203 and permit relative rotation, but not translation, between the switch drum 1500 and the nozzle 1201. The mounts also extend through openings 3011 in the proximal closure member segment 3010 to be seated in recesses 1219 in the spine 1210. Rotation of the switch drum 1500 about the shaft axis SA will ultimately result in the rotation of the actuation pin and the lock sleeve between its engaged and disengaged positions. In one arrangement, the rotation of the switch drum 1500 may be linked to the axial advancement of the closure tube or closure member. Thus, in essence, actuation of the closure system may operably engage and disengage the articulation drive system with the firing drive system in the various manners described in further detail in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, and U.S. Pat. No. 9,913,642, entitled SURGICAL INSTRUMENT COMPRISING A SENSOR SYSTEM, the entire disclosures of each being hereby incorporated by reference herein. For example, when the closure tube is in its proximal-most position corresponding to a "jaws open" position, the closure member segment 3010 will have positioned the switch drum 1500 so as to link the articulation system with the firing drive system. When, the closure tube has been moved to its distal position corresponding to a "jaws closed" position, the closure tube has rotated the switch drum 1500 to a position wherein the articulation system is delinked from the firing drive system.

As also illustrated in FIG. 4, the shaft assembly 1200 can comprise a slip ring assembly 1600 which can be configured to conduct electrical power to and/or from the end effector 1300 and/or communicate signals to and/or from the end effector 1300, for example. The slip ring assembly 1600 can comprise a proximal connector flange 1604 that is mounted to a chassis flange 1242 that extends from the chassis 1240 and a distal connector flange that is positioned within a slot defined in the shaft housings. The proximal connector flange 1604 can comprise a first face and the distal connector flange can comprise a second face which is positioned adjacent to and movable relative to the first face. The distal connector flange can rotate relative to the proximal connector flange 1604 about the shaft axis SA. The proximal connector flange 1604 can comprise a plurality of concentric, or at least substantially concentric, conductors defined in the first face thereof. A connector can be mounted on the proximal side of the connector flange and may have a plurality of contacts wherein each contact corresponds to and is in electrical contact with one of the conductors. Such an arrangement permits relative rotation between the proximal connector flange 1604 and the distal connector flange while maintaining electrical contact therebetween. The proximal connector flange 1604 can include an electrical connector 1606 which can place the conductors in signal communication with a shaft circuit board 1610 mounted to the shaft chassis 1240, for example. In at least one instance, a wiring harness comprising a plurality of conductors can extend between the electrical connector 1606 and the shaft circuit board 1610. The electrical connector 1606 may extend proximally through a connector opening 1243 defined in the chassis flange 1242. See FIG. 4. Further details regarding slip ring assembly 1600 may be found in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552, and U.S. Pat. No. 9,345,481, entitled STAPLE CARTRIDGE TISSUE THICKNESS SENSOR SYSTEM, for example. U.S. patent application Ser. No. 13/803,086, now U.S. Patent Application Publication No. 2014/0263541, U.S. patent application Ser. No. 13/800,067, now U.S. Patent Application Publication No. 2014/0263552, and U.S. Pat. No. 9,345,481 are each hereby incorporated by reference herein in their respective entireties.

As discussed above, the shaft assembly 1200 can include a proximal portion which is fixably mounted to the handle 1014 and a distal portion which is rotatable about a longitudinal axis. The rotatable distal shaft portion can be rotated relative to the proximal portion about the slip ring assembly 1600, as discussed above. The distal connector flange of the slip ring assembly 1600 can be positioned within the rotatable distal shaft portion. Moreover, further to the above, the switch drum 1500 can also be positioned within the rotatable distal shaft portion. When the rotatable distal shaft portion is rotated, the distal connector flange and the switch drum 1500 can be rotated synchronously with one another. In addition, the switch drum 1500 can be rotated between a first position and a second position relative to the distal connector flange. When the switch drum 1500 is in its first position, the articulation drive system may be operably disengaged from the firing drive system and, thus, the operation of the firing drive system may not articulate the end effector 1300 of the shaft assembly 1200. When the switch drum 1500 is in its second position, the articulation drive system may be operably engaged with the firing drive system and, thus, the operation of the firing drive system may articulate the end effector 1300 of the shaft assembly 1200. When the switch drum 1500 is moved between its first position and its second position, the switch drum 1500 is moved relative to the distal connector flange. In various instances, the shaft assembly 1200 can comprise at least one sensor configured to detect the position of the switch drum 1500.

Referring again to FIG. 4, the chassis 1240 includes at least one, and preferably two, tapered attachment portions 1244 formed thereon that are adapted to be received within corresponding dovetail slots 1702 formed within a distal attachment flange portion 1700 of the frame 1020. See FIG. 3. Each dovetail slot 1702 may be tapered or, stated another way, be somewhat V-shaped to seatingly receive the attachment portions 1244 therein. As can be further seen in FIG. 4, a shaft attachment lug 1226 is formed on the proximal end of the intermediate firing shaft portion 1222. As will be discussed in further detail below, when the interchangeable shaft assembly 1200 is coupled to the handle 1014, the shaft attachment lug 1226 is received in a firing shaft attachment cradle 1126 formed in a distal end 1125 of the longitudinal drive member 1120. See FIG. 3.

Various shaft assembly embodiments employ a latch system 1710 for removably coupling the shaft assembly 1200 to the housing 1012 and more specifically to the frame 1020. As can be seen in FIG. 4, for example, in at least one form, the latch system 1710 includes a lock member or lock yoke 1712 that is movably coupled to the chassis 1240. In the illustrated embodiment, for example, the lock yoke 1712 has a U-shape with two spaced downwardly extending legs 1714. The legs 1714 each have a pivot lug 1715 formed thereon that are adapted to be received in corresponding holes 1245 formed in the chassis 1240. Such arrangement facilitates pivotal attachment of the lock yoke 1712 to the chassis 1240. The lock yoke 1712 may include two proximally protruding lock lugs 1716 that are configured for releasable engagement with corresponding lock detents or grooves 1704 in the distal attachment flange portion 1700 of the frame 1020. See FIG. 3. In various forms, the lock yoke 1712 is biased in the proximal direction by spring or biasing member (not shown). Actuation of the lock yoke 1712 may be accomplished by a latch button 1722 that is slidably mounted on a latch actuator assembly 1720 that is mounted to the chassis 1240. The latch button 1722 may be biased in a proximal direction relative to the lock yoke 1712. As will be discussed in further detail below, the lock yoke 1712 may be moved to an unlocked position by biasing the latch button in the distal direction which also causes the lock yoke 1712 to pivot out of retaining engagement with the distal attachment flange portion 1700 of the frame 1020. When the lock yoke 1712 is in "retaining engagement" with the distal attachment flange portion 1700 of the frame 1020, the lock lugs 1716 are retainingly seated within the corresponding lock detents or grooves 1704 in the distal attachment flange portion 1700.

When employing an interchangeable shaft assembly that includes an end effector of the type described herein that is adapted to cut and fasten tissue, as well as other types of end effectors, it may be desirable to prevent inadvertent detachment of the interchangeable shaft assembly from the housing during actuation of the end effector. For example, in use the clinician may actuate the closure trigger 1032 to grasp and manipulate the target tissue into a desired position. Once the target tissue is positioned within the end effector 1300 in a desired orientation, the clinician may then fully actuate the closure trigger 1032 to close the anvil 2000 and clamp the target tissue in position for cutting and stapling. In that instance, the first drive system 1030 has been fully actuated. After the target tissue has been clamped in the end effector 1300, it may be desirable to prevent the inadvertent detachment of the shaft assembly 1200 from the housing 1012. One form of the latch system 1710 is configured to prevent such inadvertent detachment.

As can be most particularly seen in FIG. 4, the lock yoke 1712 includes at least one and preferably two lock hooks 1718 that are adapted to contact corresponding lock lug portions 1256 that are formed on the closure shuttle 1250. When the closure shuttle 1250 is in an unactuated position (i.e., the first drive system 1030 is unactuated and the anvil 2000 is open), the lock yoke 1712 may be pivoted in a distal direction to unlock the interchangeable shaft assembly 1200 from the housing 1012. When in that position, the lock hooks 1718 do not contact the lock lug portions 1256 on the closure shuttle 1250. However, when the closure shuttle 1250 is moved to an actuated position (i.e., the first drive system 1030 is actuated and the anvil 2000 is in the closed position), the lock yoke 1712 is prevented from being pivoted to an unlocked position. Stated another way, if the clinician were to attempt to pivot the lock yoke 1712 to an unlocked position or, for example, the lock yoke 1712 was inadvertently bumped or contacted in a manner that might otherwise cause it to pivot distally, the lock hooks 1718 on the lock yoke 1712 will contact the lock lug portions 1256 on the closure shuttle 1250 and prevent movement of the lock yoke 1712 to an unlocked position.

Attachment of the interchangeable shaft assembly 1200 to the handle 1014 will now be described. To commence the coupling process, the clinician may position the chassis 1240 of the interchangeable shaft assembly 1200 above or adjacent to the distal attachment flange portion 1700 of the frame 1020 such that the tapered attachment portions 1244 formed on the chassis 1240 are aligned with the dovetail slots 1702 in the frame 1020. The clinician may then move the shaft assembly 1200 along an installation axis that is perpendicular to the shaft axis SA to seat the attachment portions 1244 in "operable engagement" with the corresponding dovetail slots 1702. In doing so, the shaft attachment lug 1226 on the intermediate firing shaft portion 1222 will also be seated in the cradle 1126 in the longitudinally movable drive member 1120 and the portions of the pin 1037 on the second closure link 1038 will be seated in the corresponding hooks 1252 in the closure shuttle 1250. As used herein, the term "operable engagement" in the context of two components means that the two components are sufficiently engaged with each other so that upon application of an actuation motion thereto, the components may carry out their intended action, function and/or procedure.

At least five systems of the interchangeable shaft assembly 1200 can be operably coupled with at least five corresponding systems of the handle 1014. A first system can comprise a frame system which couples and/or aligns the frame 1020 or spine 1210 of the shaft assembly 1200 with the frame 1020 of the handle 1014. Another system can comprise a closure drive system 1030 which can operably connect the closure trigger 1032 of the handle 1014 and a closure tube of the shaft assembly 1200. As outlined above, the closure shuttle 1250 of the shaft assembly 1200 can be engaged with the pin 1037 on the second closure link 1038. Another system can comprise the firing drive system 1080 which can operably connect the firing trigger 1130 of the handle 1014 with the intermediate firing shaft portion 1222 of the shaft assembly 1200. As outlined above, the shaft attachment lug 1226 can be operably connected with the cradle 1126 of the longitudinal drive member 1120. Another system can comprise an electrical system which can signal to a controller in the handle 1014, such as microcontroller, for example, that a shaft assembly, such as shaft assembly 1200, for example, has been operably engaged with the handle 1014 and/or, two, conduct power and/or communication signals between the shaft assembly 1200 and the handle 1014. For instance, the shaft assembly 1200 can include an electrical connector 1810 that is operably mounted to the shaft circuit board 1610. The electrical connector 1810 is configured for mating engagement with a corresponding electrical connector 1800 on the circuit board 1100. Further details regarding the circuitry and control systems may be found in U.S. patent application Ser. No. 13/803,086, now U.S. Patent Application Publication No. 2014/0263541 entitled ARTICULATABLE SURGICAL INSTRUMENT COMPRISING AN ARTICULATION LOCK, and U.S. patent application Ser. No. 14/226,142, now U.S. Pat. No. 9,913,642 entitled SURGICAL INSTRUMENT COMPRISING A SENSOR SYSTEM, the entire disclosures of each which were previously incorporated by reference herein. The fifth system may consist of the latching system for releasably locking the shaft assembly 1200 to the handle 1014.

The anvil 2000 in the illustrated example includes an anvil body 2002 that terminates in an anvil mounting portion 2010. The anvil mounting portion 2010 is movably or pivotably supported on the elongate channel 1310 for selective pivotal travel relative thereto about a fixed anvil pivot axis PA that is transverse to the shaft axis SA. In the illustrated arrangement, a pivot member or anvil trunnion 2012 extends laterally out of each lateral side of the anvil mounting portion 2010 to be received in a corresponding trunnion cradle 1316 formed in the upstanding walls 1315 of the proximal end portion 1312 of the elongate channel 1310. The anvil trunnions 2012 are pivotally retained in their corresponding trunnion cradle 1316 by the channel cap or anvil retainer 1290. The channel cap or anvil retainer 1290 includes a pair of attachment lugs that are configured to be retainingly received within corresponding lug grooves or notches formed in the upstanding walls 1315 of the proximal end portion 1312 of the elongate channel 1310. See FIG. 5.

Still referring to FIG. 5, in at least one arrangement, the distal closure member or end effector closure tube 3050 employs two axially offset, proximal and distal positive jaw opening features 3060 and 3062. The positive jaw opening features 3060, 3062 are configured to interact with corresponding relieved areas and stepped portions formed on the anvil mounting portion 2010 as described in further detail in U.S. patent application Ser. No. 15/635,631, entitled SURGICAL INSTRUMENT WITH AXIALLY MOVABLE CLOSURE MEMBER, now U.S. Patent Application Publication No. 2019/0000464, the entire disclosure which has been herein incorporated by reference. Other jaw opening arrangements may be employed.

Figure 6:
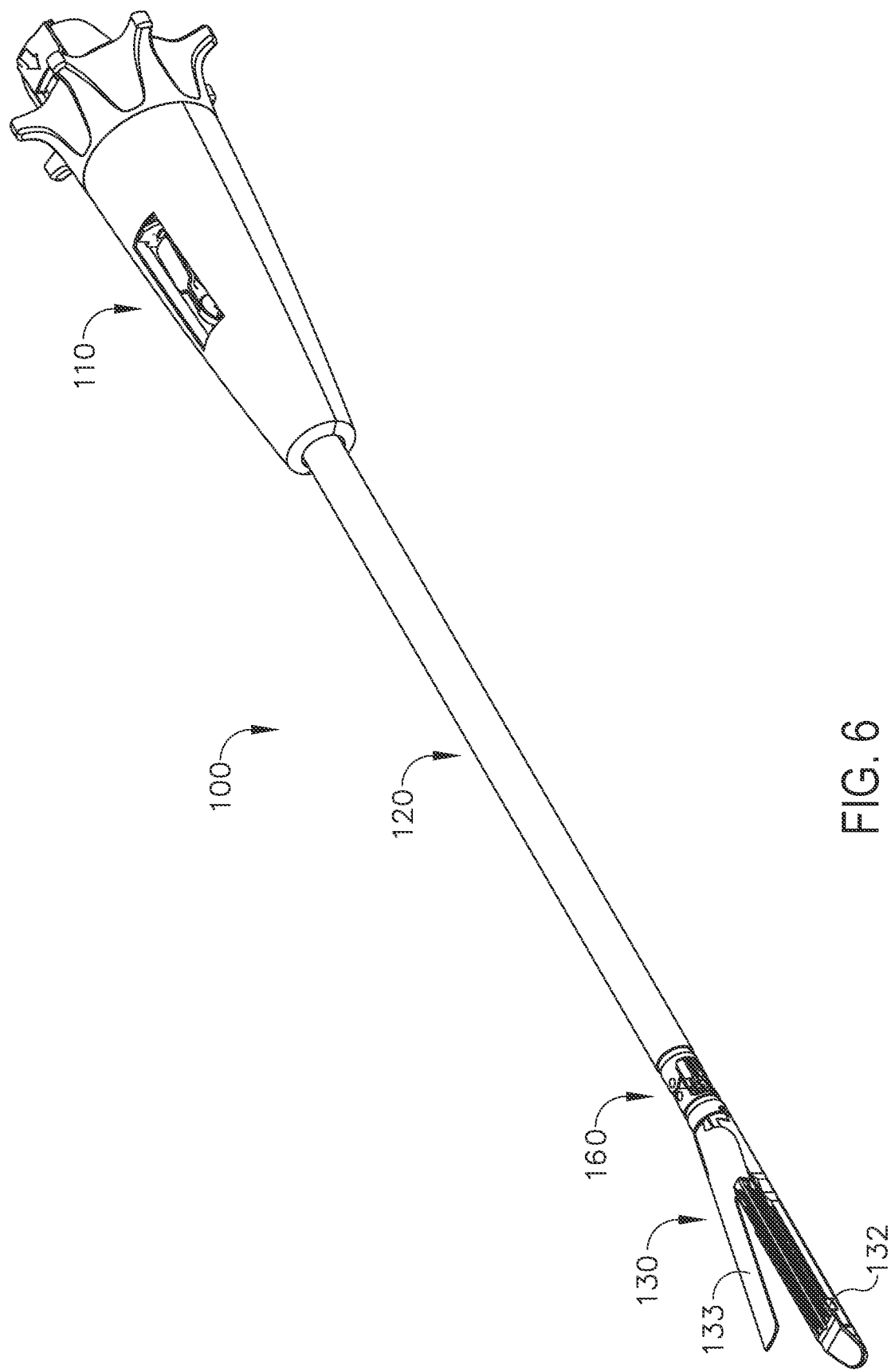
FIG. 6 is a perspective view of a shaft assembly in accordance with at least one embodiment.
Figure 7:
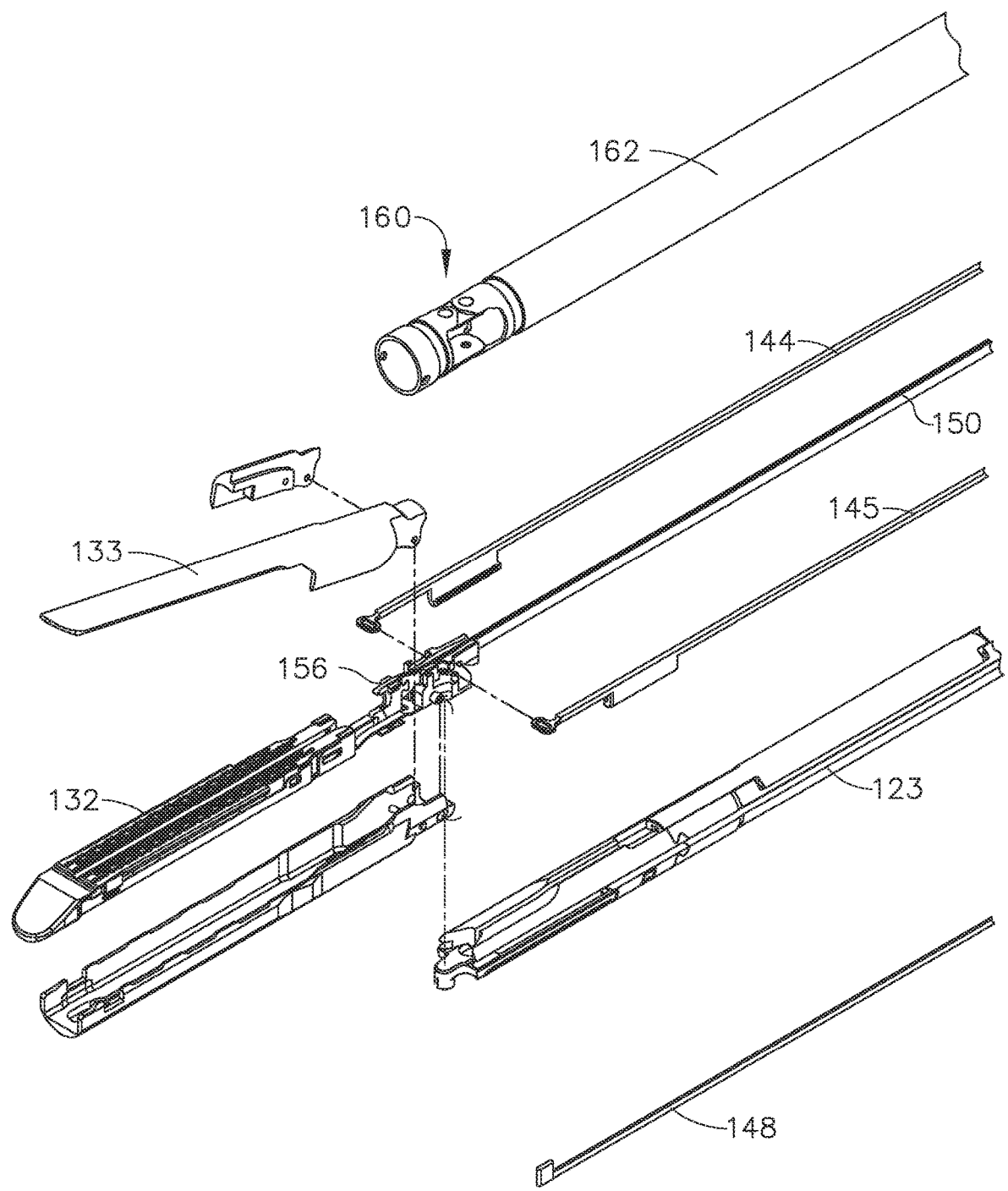
FIG. 7 is an exploded view of a distal end of the shaft assembly of FIG. 6.

A shaft assembly 100 is illustrated in FIGS. 6 and 7. The shaft assembly 100 comprises an attachment portion 110, a shaft 120 extending distally from the attachment portion 110, and an end effector 130 attached to the shaft 120. The shaft assembly 100 is configured to clamp, staple, and cut tissue. The attachment portion 110 is configured to be attached to a handle of a surgical instrument and/or the arm of a surgical robot, for example.

Referring to FIG. 7, the shaft assembly 100 comprises cooperating articulation rods 144, 145 configured to articulate the end effector 130 relative to the shaft 120 about an articulation joint 160. The shaft assembly 100 further comprises an articulation lock bar 148, an outer shaft tube 162, and a spine portion 123.

Referring to FIG. 7, the shaft assembly 100 comprises a firing shaft 150 including a firing member 156 attached to a distal end of the firing shaft 150. The firing member 156 comprises upper camming flanges configured to engage an anvil jaw 133 and lower camming members configured to engage a cartridge jaw 132. The firing shaft 150 is configured to be advanced distally through a closure stroke to clamp the anvil jaw 133 relative to the cartridge jaw 132 with the camming members. Further advancement of the firing shaft 150 through a firing stroke is configured to advance the firing member 156 through the cartridge jaw 132 to deploy staples from the cartridge jaw 132 and cut tissue during the firing stroke. More details of the shaft assembly 100 can be found in U.S. patent application Ser. No. 15/385,887 entitled METHOD FOR ATTACHING A SHAFT ASSEMBLY TO A SURGICAL INSTRUMENT AND, ALTERNATIVELY, TO A SURGICAL ROBOT, which is incorporated by reference in its entirety.

Figure 8:
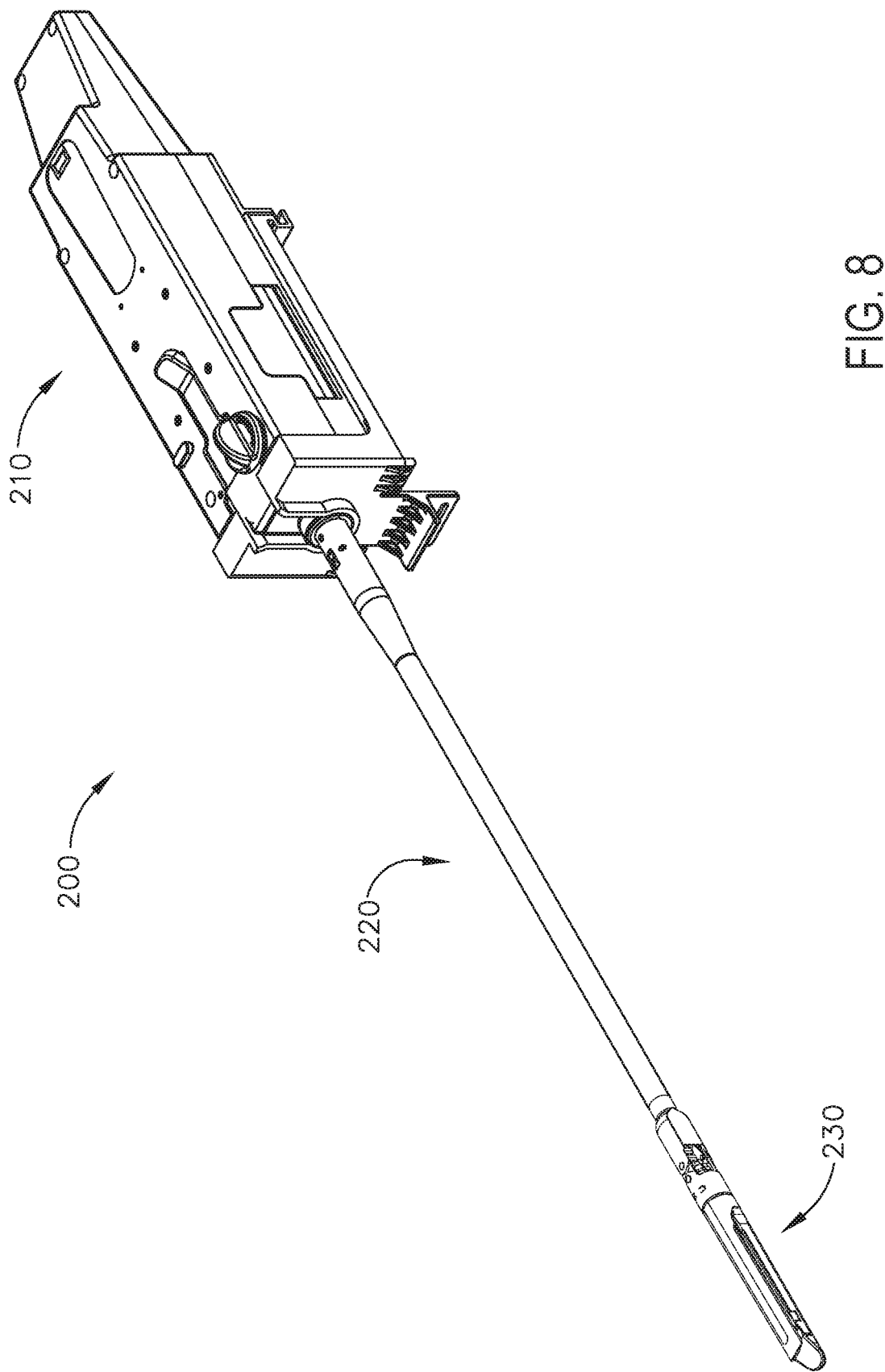
FIG. 8 is a perspective view of a surgical instrument assembly comprising a proximal control interface, a shaft assembly, and an end effector assembly.
Figure 9:
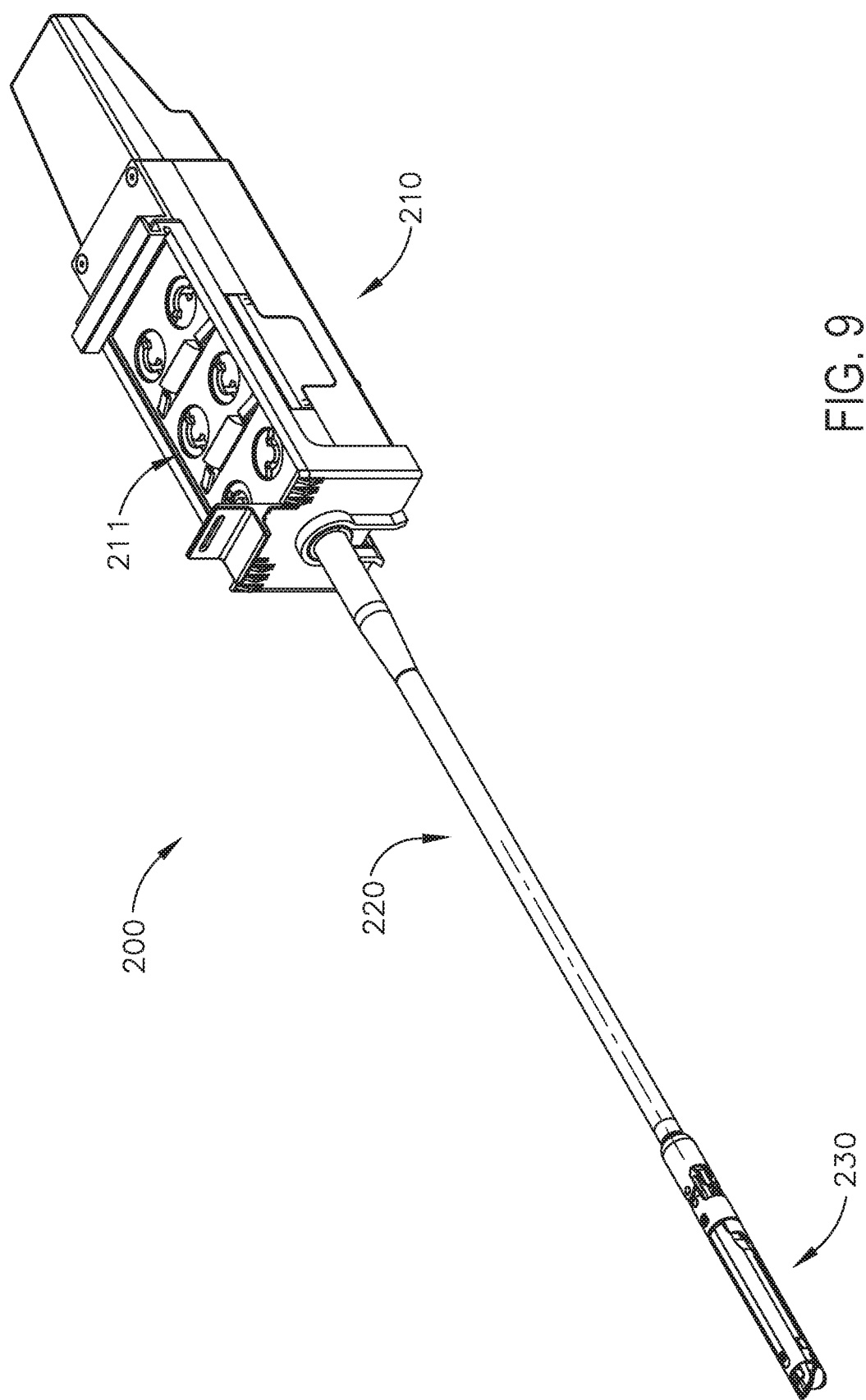
FIG. 9 is a bottom perspective view of the surgical instrument assembly of FIG. 8.

FIGS. 8 and 9 depict a surgical instrument assembly 200 configured to be used with a surgical robot. The surgical instrument assembly 200 is configured to staple and cut tissue, although the surgical instrument assembly 200 could be adapted to treat tissue in any suitable way, such as by applying heat energy, electrical energy, and/or vibrations to the tissue, for example. The surgical instrument assembly 200 comprises a proximal control interface 210 configured to be coupled to a robotic arm of a surgical robot and a shaft assembly 220 configured to be attached to the proximal control interface 210. The shaft assembly 220 comprises an end effector 230 configured to clamp, cut, and staple tissue. The proximal control interface 210 comprises a plurality of drive discs 211, each for actuating one or more functions of the surgical instrument assembly 200. Each drive disc 211 can be independently driven and/or cooperatively driven with one or more other drive discs 211 by one or more motors of the surgical robot and/or robotic arm of the surgical robot. More details about the surgical instrument assembly 200 can be found in U.S. patent application Ser. No. 15/847,297, entitled SURGICAL INSTRUMENTS WITH DUAL ARTICULATION DRIVERS, which is incorporated by reference in its entirety.

Figure 10:
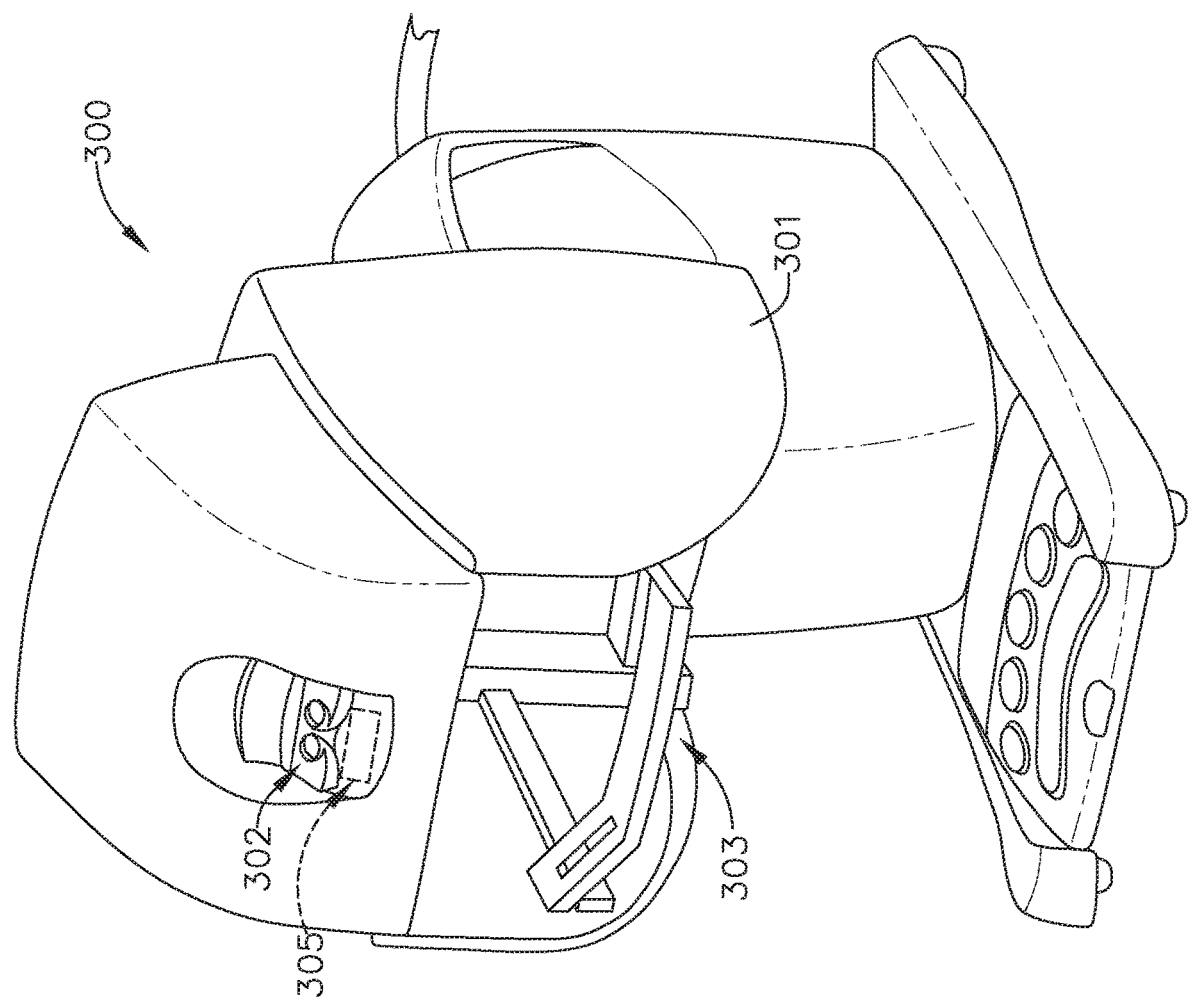
FIG. 10 is a perspective view of an example of one form of robotic controller according to one aspect of this disclosure.
Figure 11:
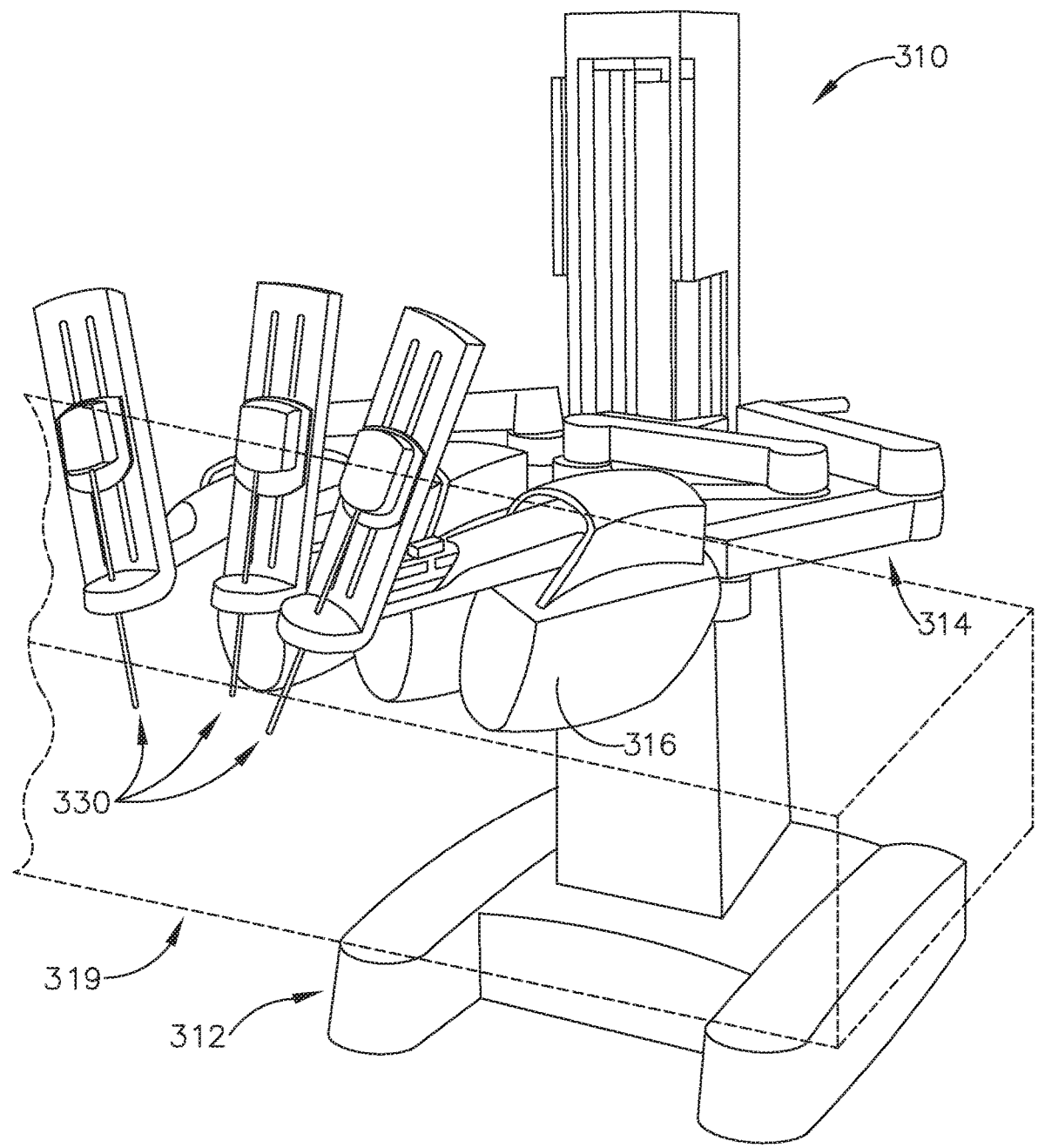
FIG. 11 is a perspective view of an example of one form of robotic surgical arm cart/manipulator of a robotic surgical system operably supporting a plurality of surgical tools according to one aspect of this disclosure.
Figure 12:
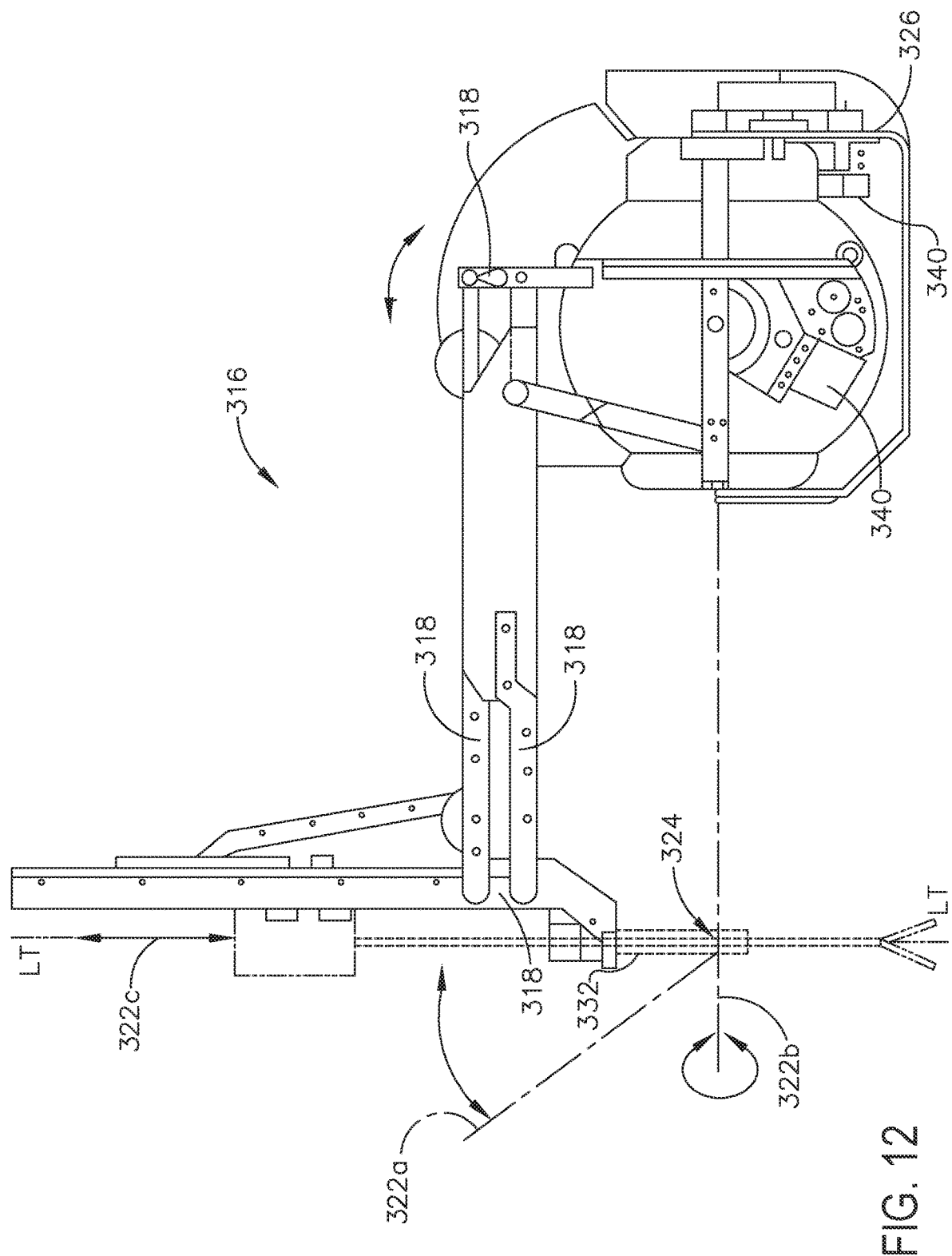
FIG. 12 is a side view of the robotic surgical arm cart/manipulator depicted in FIG. 11 according to one aspect of this disclosure.

Various embodiments disclosed herein may be employed in connection with a robotic system 300 of the type depicted in FIGS. 10-12, for example. FIG. 10 depicts one version of a master controller 301 that may be used in connection with a robotic arm slave cart 310 of the type depicted in FIG. 11. Master controller 301 and robotic arm slave cart 310, as well as their respective components and control systems are collectively referred to herein as a robotic system 300. Examples of such systems and devices are disclosed in U.S. Pat. No. 7,524,320, entitled MECHANICAL ACTUATOR INTERFACE SYSTEM FOR ROBOTIC SURGICAL TOOLS, as well as U.S. Pat. No. 9,072,535, entitled SURGICAL STAPLING INSTRUMENTS WITH ROTATABLE STAPLE DEPLOYMENT ARRANGEMENTS, which are each hereby incorporated by reference herein in their respective entireties. Thus, various details of such devices will not be described in detail herein beyond that which may be necessary to understand various embodiments and forms of the present disclosure. As is known, the master controller 301 generally includes master controllers (generally represented as 303 in FIG. 10) which are grasped by the surgeon and manipulated in space while the surgeon views the procedure via a stereo display 302. The master controllers 301 generally comprise manual input devices which preferably move with multiple degrees of freedom, and which often further have an actuatable handle for actuating tools (for example, for closing grasping jaws, applying an electrical potential to an electrode, or the like).

As can be seen in FIG. 11, in one form, the robotic arm cart 310 may be configured to actuate one or more surgical tools, generally designated as 330. Various robotic surgery systems and methods employing master controller and robotic arm cart arrangements are disclosed in U.S. Pat. No. 6,132,368, entitled MULTI-COMPONENT TELEPRESENCE SYSTEM AND METHOD the entire disclosure of which is hereby incorporated by reference herein. In various forms, the robotic arm cart 310 includes a base 312 from which, in the illustrated embodiment, surgical tools may be supported. In various forms, the surgical tool(s) may be supported by a series of manually articulatable linkages, generally referred to as set-up joints 314, and a robotic manipulator 316. In various embodiments, the linkage and joint arrangement may facilitate rotation of a surgical tool around a point in space, as more fully described in issued U.S. Pat. No. 5,817,084, entitled REMOTE CENTER POSITIONING DEVICE WITH FLEXIBLE DRIVE, the entire disclosure of which is hereby incorporated by reference herein. The parallelogram arrangement constrains rotation to pivoting about an axis 322a, sometimes called the pitch axis. The links supporting the parallelogram linkage are pivotally mounted to set-up joints 314 (FIG. 11) so that the surgical tool further rotates about an axis 322b, sometimes called the yaw axis. The pitch and yaw axes 322a, 322b intersect at the remote center 324, which is aligned along an elongate shaft of a surgical tool. The surgical tool may have further degrees of driven freedom as supported by manipulator 316, including sliding motion of the surgical tool along the longitudinal axis "LT-LT". As the surgical tool slides along the tool axis LT-LT relative to manipulator 316 (arrow 322c), remote center 324 remains fixed relative to base 326 of manipulator 316. Hence, the entire manipulator is generally moved to re-position remote center 324. Linkage 318 of manipulator 316 may be driven by a series of motors 340. These motors actively move linkage 318 in response to commands from a processor of a control system. The motors 340 may also be employed to manipulate the surgical tool. Alternative joint structures and set up arrangements are also contemplated. Examples of other joint and set up arrangements, for example, are disclosed in U.S. Pat. No. 5,878,193, entitled AUTOMATED ENDOSCOPE SYSTEM FOR OPTIMAL POSITIONING, the entire disclosure of which is hereby incorporated by reference herein. Additionally, while the data communication between a robotic component and the processor of the robotic surgical system is primarily described herein with reference to communication between the surgical tool and the master controller 301, it should be understood that similar communication may take place between circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like. In accordance with at least one aspect, various surgical instruments disclosed herein may be used in connection with other robotically-controlled or automated surgical systems and are not necessarily limited to use with the specific robotic system components shown in FIGS. 10-12 and described in the aforementioned references.

Figure 13:
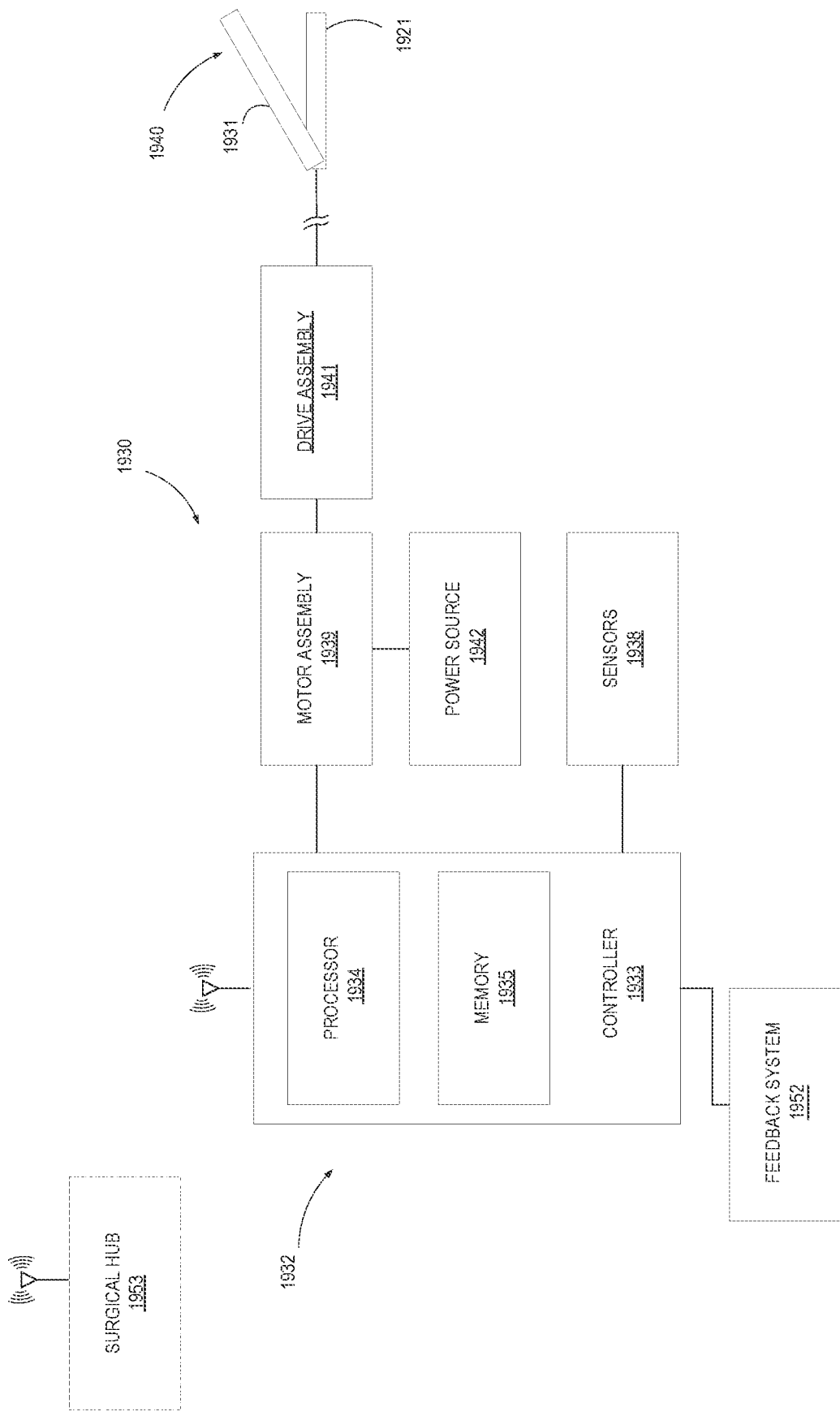
FIG. 13 illustrates a block diagram of a surgical system for use with one or more surgical instruments, tools, and/or robotic systems in accordance with one or more aspects of the present disclosure.

FIG. 13 illustrates a block diagram of a surgical system 1930 for use with one or more surgical instruments, tools, and/or robotic systems in accordance with one or more aspects of the present disclosure. The system 1930 includes a control circuit 1932. The control circuit 1932 includes a microcontroller 1933 comprising a processor 1934 and a storage medium such as, for example, a memory 1935.

A motor assembly 1939 includes one or more motors, driven by motor drivers. The motor assembly 1939 operably couples to a drive assembly 1941 to drive, or effect, one or more motions at an end effector 1940. The drive assembly 1941 may include any number of components suitable for transmitting motion to the end effector 1940 such as, for example, one or more linkages, bars, tubes, and/or cables, for example.

One or more of sensors 1938, for example, provide real-time feedback to the processor 1934 about one or more operational parameters monitored during a surgical procedure being performed by the surgical system 1930. The operational parameters can be associated with a user performing the surgical procedure, a tissue being treated, and/or one or more components of the surgical system 1930, for example. The sensor 1938 may comprise any suitable sensor, such as, for example, a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

Further to the above, in various arrangements, the sensors 1938 may comprise any suitable sensor for detecting one or more conditions at the end effector 1940 including, without limitation, a tissue thickness sensor such as a Hall Effect Sensor or a reed switch sensor, an optical sensor, a magneto-inductive sensor, a force sensor, a pressure sensor, a piezo-resistive film sensor, an ultrasonic sensor, an eddy current sensor, an accelerometer, a pulse oximetry sensor, a temperature sensor, a sensor configured to detect an electrical characteristic of a tissue path (such as capacitance or resistance), or any combination thereof. As another example, and without limitation, the sensors 1938 may include one or more sensors located at, or about, an articulation joint extending proximally from the end effector 1940. Such sensors may include, for example, a potentiometer, a capacitive sensor (slide potentiometer), piezo-resistive film sensor, a pressure sensor, a pressure sensor, or any other suitable sensor type. In some arrangements, the sensor 1938 may comprise a plurality of sensors located in multiple locations in the end effector 1940.

In certain aspects, the system 1930 includes a feedback system 1952 which includes one or more devices for providing a sensory feedback to a user. Such devices may comprise, for example, visual feedback devices (e.g., an LCD display screen, a touch screen, LED indicators), audio feedback devices (e.g., a speaker, a buzzer) or tactile feedback devices (e.g., haptic actuators).

The microcontroller 1933 may be programmed to perform various functions such as precise control over the speed and position of the drive assembly 1941. In one aspect, the microcontroller 1933 may be any single-core or multicore processor such as those known under the trade name ARM Cortex by Texas Instruments. In one aspect, the main microcontroller 1933 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

The microcontroller 1933 may be configured to compute a response in the software of the microcontroller 1933. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

The motor assembly 1939 includes one or more electric motors and one or more motor drivers. The electric motors can be in the form of a brushed direct current (DC) motor with a gearbox and mechanical links to the drive assembly 1941. In one aspect, a motor driver may be an A3941 available from Allegro Microsystems, Inc.

In various forms, the motor assembly 1939 includes a brushed DC driving motor having a maximum rotational speed of approximately 25,000 RPM. In other arrangements, the motor assembly 1939 may include a brushless motor, a cordless motor, a synchronous motor, a stepper motor, or any other suitable electric motor. The motor driver may comprise an H-bridge driver comprising field-effect transistors (FETs), for example.

The motor assembly 1939 can be powered by a power source 1942. In certain aspects, the power source 1942 includes one or more batteries which may include a number of battery cells connected in series that can be used as the power source to power the motor assembly 1939. In certain circumstances, the battery cells of the power assembly may be replaceable and/or rechargeable. In at least one example, the battery cells can be lithium-ion batteries which can be couplable to and separable from the power assembly.

Further to the above, the end effector 1940 includes a first jaw 1921 and a second jaw 1931. At least one of the first jaw 1921 and the second jaw 1931 is rotatable relative to the other during a closure motion that transitions the end effector 1940 from an open configuration toward a closed configuration. The closure motion may cause the jaws 1921, 1931 to grasp tissue therebetween. In certain arrangements, sensors, such as, for example, a strain gauge or a micro-strain gauge, are configured to measure one or more parameters of the end effector 1940, such as, for example, the amplitude of the strain exerted on the one or both of the jaws 1921, 1931 during a closure motion, which can be indicative of the closure forces applied to the jaws 1921, 1931. The measured strain is converted to a digital signal and provided to the processor 1934, for example. Alternatively, additionally, sensors such as, for example, a load sensor, can measure a closure force and/or a firing force applied to the jaws 1921, 1931.

In various arrangements, a current sensor can be employed to measure the current drawn by a motor of the motor assembly 1939. The force required to advance the drive assembly 1941 can correspond to the current drawn by the motor, for example. The measured force is converted to a digital signal and provided to the processor 1934.

In one form, strain gauge sensors can be used to measure the force applied to the tissue by the end effector 1940, for example. A strain gauge can be coupled to the end effector 1940 to measure the force on the tissue being treated by the end effector 1940. In one aspect, the strain gauge sensors can measure the amplitude or magnitude of the strain exerted on a jaw of an end effector 1940 during a closure motion which can be indicative of the tissue compression. The measured strain is converted to a digital signal and provided to a processor 1934.

The measurements of the tissue compression, the tissue thickness, and/or the force required to close the end effector on the tissue, as respectively measured by the sensors 1938 can be used by the microcontroller 1933 to characterize the selected position of one or more components of the drive assembly 1941 and/or the corresponding value of the speed of one or more components of the drive assembly 1941. In one instance, a memory (e.g. memory 1935) may store a technique, an equation, and/or a lookup table which can be employed by the microcontroller 1933 in the assessment.

The system 1930 may comprise wired or wireless communication circuits to communicate with surgical hubs (e.g. surgical hub 1953), communication hubs, and/or robotic surgical hubs, for example. Additional details about suitable interactions between a system 1930 and the surgical hub 1953 are disclosed in U.S. patent application Ser. No. 16/209,423 entitled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981, the entire disclosure of which is incorporated by reference in its entirety herein.

In various aspects, the control circuit 1932 can be configured to implement various processes described herein. In certain aspects, the control circuit 1932 may comprise a microcontroller comprising one or more processors (e.g., microprocessor, microcontroller) coupled to at least one memory circuit. The memory circuit stores machine-executable instructions that, when executed by the processor, cause the processor to execute machine instructions to implement various processes described herein. The processor may be any one of a number of single-core or multicore processors known in the art. The memory circuit may comprise volatile and non-volatile storage media. The processor may include an instruction processing unit and an arithmetic unit. The instruction processing unit may be configured to receive instructions from the memory circuit of this disclosure.

Alternatively, in certain instances, the control circuit 1932 can be in the form of a combinational logic circuit configured to implement various processes described herein. The combinational logic circuit may comprise a finite state machine comprising a combinational logic configured to receive data, process the data by the combinational logic, and provide an output.

Alternatively, in certain instances, the control circuit 1932 can be in the form of a sequential logic circuit. The sequential logic circuit can be configured to implement various processes described herein. The sequential logic circuit may comprise a finite state machine. The sequential logic circuit may comprise a combinational logic, at least one memory circuit, and a clock, for example. The at least one memory circuit can store a current state of the finite state machine. In certain instances, the sequential logic circuit may be synchronous or asynchronous. In other instances, the control circuit 1932 may comprise a combination of a processor (e.g., processor 1934) and a finite state machine to implement various processes herein. In other aspects, the finite state machine may comprise a combination of a combinational logic circuit (and the sequential logic circuit, for example.

Figure 14:
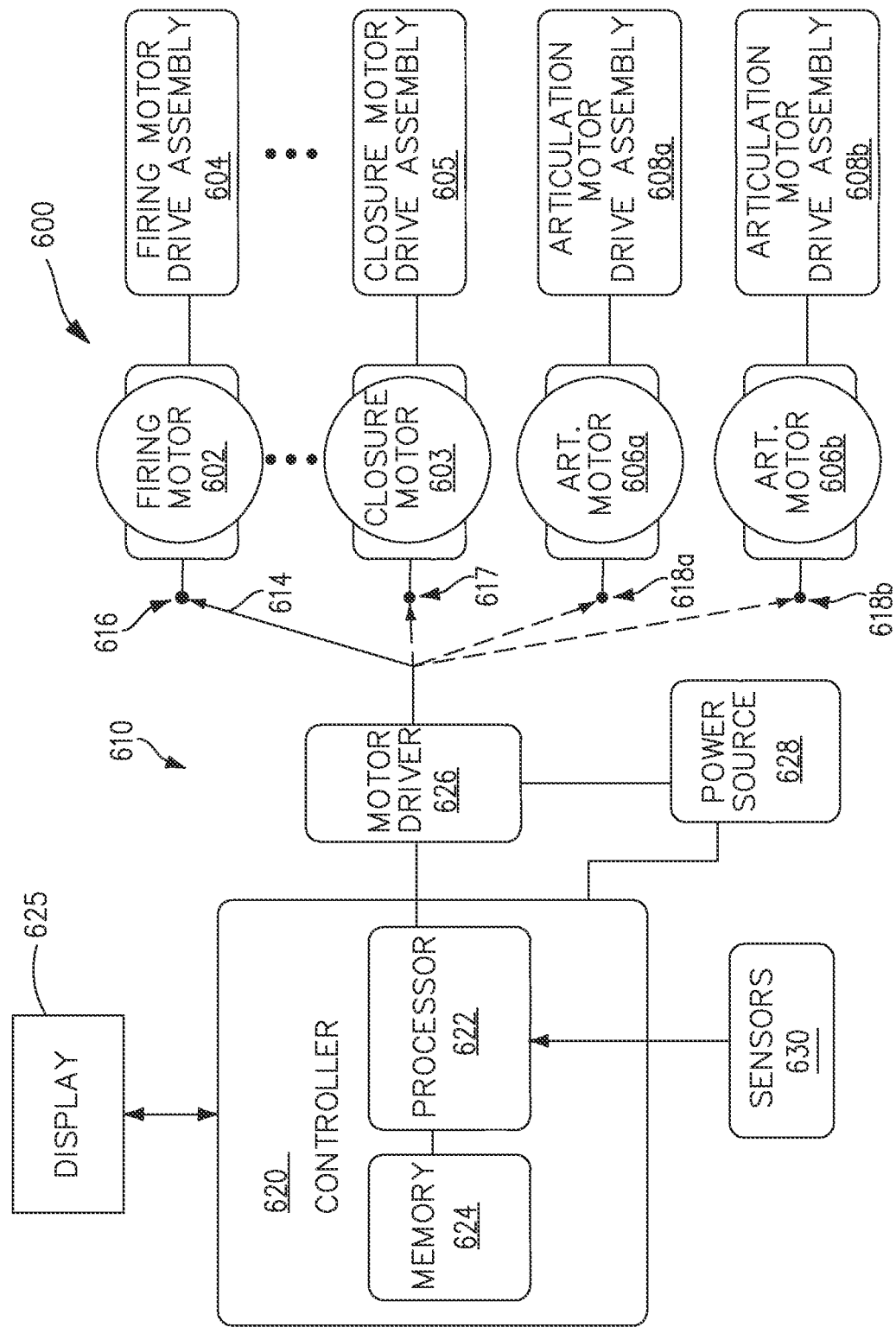
FIG. 14 illustrates a block diagram of a surgical system for use with one or more surgical instruments, tools, and/or robotic systems in accordance with one or more aspects of the present disclosure.

FIG. 14 illustrates a block diagram of a surgical system 600 for use with one or more surgical instruments, tools, and/or robotic systems in accordance with one or more aspects of the present disclosure. The surgical system 600 is similar in many respects to the surgical system 1930, which are not repeated herein at the same of detail for brevity. For example, like the surgical system 1930, the surgical system 600 includes a control circuit comprising a microcontroller 620 comprising a processor 622 and a memory 624, sensors 630, and a power source 628, which are similar, respectively, to the microcontroller 1933, the processor 1934, the memory 1935, and the power source 1942. Additionally, the surgical system 600 includes a plurality of motors and corresponding driving assemblies that can be activated to perform various functions.

In certain instances, a first motor can be activated to perform a first function, a second motor can be activated to perform a second function, a third motor can be activated to perform a third function, a fourth motor can be activated to perform a fourth function, and so on. In certain instances, the plurality of motors can be individually activated to cause firing, closure, and/or articulation motions in an end effector 1940, for example. The firing, closure, and/or articulation motions can be transmitted to the end effector 1940 through a shaft assembly, for example.

In certain instances, the system 600 may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from a staple cartridge into tissue captured by the end effector 1940 and/or the cutting edge of the I-beam element to be advanced to cut the captured tissue, for example. The I-beam element may be retracted by reversing the direction of the motor 602.

In certain instances, the system 600 may include a closure motor 603. The closure motor 603 may be operably coupled to a closure motor drive assembly 605 which can be configured to transmit closure motions, generated by the motor 603 to the end effector 1940, in particular to displace a closure tube to close an anvil and compress tissue between the anvil and the staple cartridge. The closure motions may cause the end effector 1940 to transition from an open configuration to an approximated configuration to grasp tissue, for example. The end effector 1940 may be transitioned to an open position by reversing the direction of the motor 603.

In certain instances, the system 600 may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to a shaft, for example.

As described above, the system 600 may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube and the I-beam element to advance distally as described in more detail hereinbelow.

In certain instances, the system 600 may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 14, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 14, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

As disclosed above, a powered surgical stapling system is composed of multiple mechanical and electrical subsystems. The components may include, without limitation, an end effector composed of a first jaw and a second jaw, in which the first jaw is configured to include a staple cartridge and the second jaw includes an anvil configured to clamp one or more staples to a tissue grasped by the jaws when they close. The end effector may also include a blade or tissue cutting edge capable of a reciprocating motion to sever the tissue once the one or more staples have been affixed to the tissue. The end effector may be mounted on a shaft assembly which may further include an articulation joint. The articulation joint may be configured to rotate about an articulation axis, thereby rotating the end effector about the articulation axis with respect to a longitudinal axis of the shaft assembly.

In some aspects, a user may cause the anvil to close on a tissue supported by the first jaw using a manual trigger mechanism. In an alternative aspect, the anvil may be closed on the first jaw by a drive train actuated by a motor energized by a motor power supply when the trigger mechanism is depressed. In some aspects, the reciprocating motion of the blade or tissue cutting edge may be driven by an electrically activated motor. In some other aspects, the articulation joint may be rotated either by the same electrically activated motor that drives the blade, or a separate motor. The motor may be controlled by a combination of activation switches and one or more motor controllers through a series of motor control signals.

Thus, as disclosed above, the powered surgical stapling device is composed of a number of high-precision mechanical components working together to effect the stapling and cutting of the tissue. In some sub-systems, mechanical components may work together to cause the blade to slide in a distal direction to cut tissue, and slide back to a home position once the cutting operation is completed. In another sub-system, mechanical components may work together to cause the articulation joint to rotate in a first direction and then back to a second position. In yet another sub-system, mechanical components may work together to cause the anvil to close on the first jaw, thereby compressing and stapling a tissue and then cause the anvil to move away from the first jaw after the tissue has been compressed and stapled. These sub-systems may require the interaction of multiple mechanical linkages (drive-trains) with a motor with or without a gear reducer assembly. One or more sensors may be used to detect the types and speeds of the motions of the components of the drive-trains for use as feed-back to a motor controller.

The motor controller may include one or more algorithms—implemented either in hardware, software, or firmware—designed to actuate the drive-trains in a manner responsive to the surgical environment. In one aspect, the surgical environment may reflect the type or thickness of a tissue grasped, stapled, and cut in the jaws. In another aspect, the surgical environment may reflect obstructions around the articulation joint. In yet another aspect, the surgical environment may reflect the thickness of a tissue being compressed and stapled by the anvil and the first jaw. The motor controller should be configured to adjust the motor control signals so that the activation of the motor or motors may be optimized for the task at hand.

Additionally, the powered stapling system may be designed to proactively make small performance corrections to negate any performance deficiencies of a sub-system, such as the tissue cutting sub-system, the jaw-clamping sub-system, or the articulation sub-system. These adjustments may be gauged against past historical data from pervious cycles or anticipated for subsequent cycles based on the trending performance. These type of enhancements may normalize the performance of the device over repeated uses or normalize manufacturing deviations in performance between devices.

In the operation of various DC motors, the motor operation may be controlled by a pulse-width modulation (PWM) system. A PWM system generates a signal based on a base frequency defined by a time period in which current pulses are supplied to the motor. Each current pulse occurs over some portion of the time period of the base frequency and may represent any percentage of the time period from 0% (no current supplied over the time period) to 100% (current supplied over the entire time period). The speed of the motor may depend on the portion of the time period during which the current is supplied, Hence, the motor speed may be modulated by the pulse width of the current over the time period.

Typically, the PWM pulse train is composed of square-wave signals, in which the current pulses are either off or on at a fixed current for the duration of the pulse. The motor may actuate during the on-current phase, and may be unactuated when the current is off. This rotational motion may be transferred to a gear reducer assembly mechanically coupled to the motor. The gear reducer assembly is then mechanically coupled to the components of one or more drive trains, associated, for example, with a rotational motion of the anvil, a transverse motion of the tissue cutting blade, or rotational motion of an articulation joint. Under ideal conditions, the motions associated with the gear reducer assembly and the associated components of the drive trains would move synchronously with the motion of the motor and with the square pulse train of the PWM motor control signal. Thus, all of the drive train components may move during the on-current phase, and may be unactuated when the current is off.

However, non-idealities may exist in the motions of the gear reducer assembly and the drive train components. Such non-idealities may include, without limitations, gear backlash, stiction at gear interfaces, friction at the interfaces of smooth components, and bowing of elongated components such as a firing member, an articulation system, or a firing shaft portion. It may be further recognized that such mechanical non-idealities may change over time reflecting wear and use of the mechanical components. As a result, the motions of the gear reducer assembly and the drive train components may not follow the sharp rise and fall of the current pulse train. It would therefore be useful to modify the shape of the PWM current pulses so that the mechanical components would be more aligned with the PWM current output. In this manner, the mechanical coupling of the motor to the overall system response may be accomplished by adapting the motor control signal to system configurations or physical properties of the parts of the drive train. Such control system adaptation may compensate for the previously identified variances in the surgical stapling system from the nominal, ideal, or average system.

Adjustments may be made to the motor control algorithm based on detection of individual device drive train properties. The powered surgical stapler system may monitor system drive train reaction relative to input motor control signals and adjust the input control signals based on the individual system response relative to pre-established baseline performance. In some non-limiting aspects, the monitored responses could be frictional loss, acceleration or deceleration responses to a stepped input signal, PID control variation, harmonics of the system, noise, or force/speed of the motor. In some aspects, the adaptation to the motor control algorithm may include modifications of the PID control parameters, triggering delay of dynamic braking, level or function window around the triggering thresholds, power, current, voltage, or PWM signals.

Figure 15:
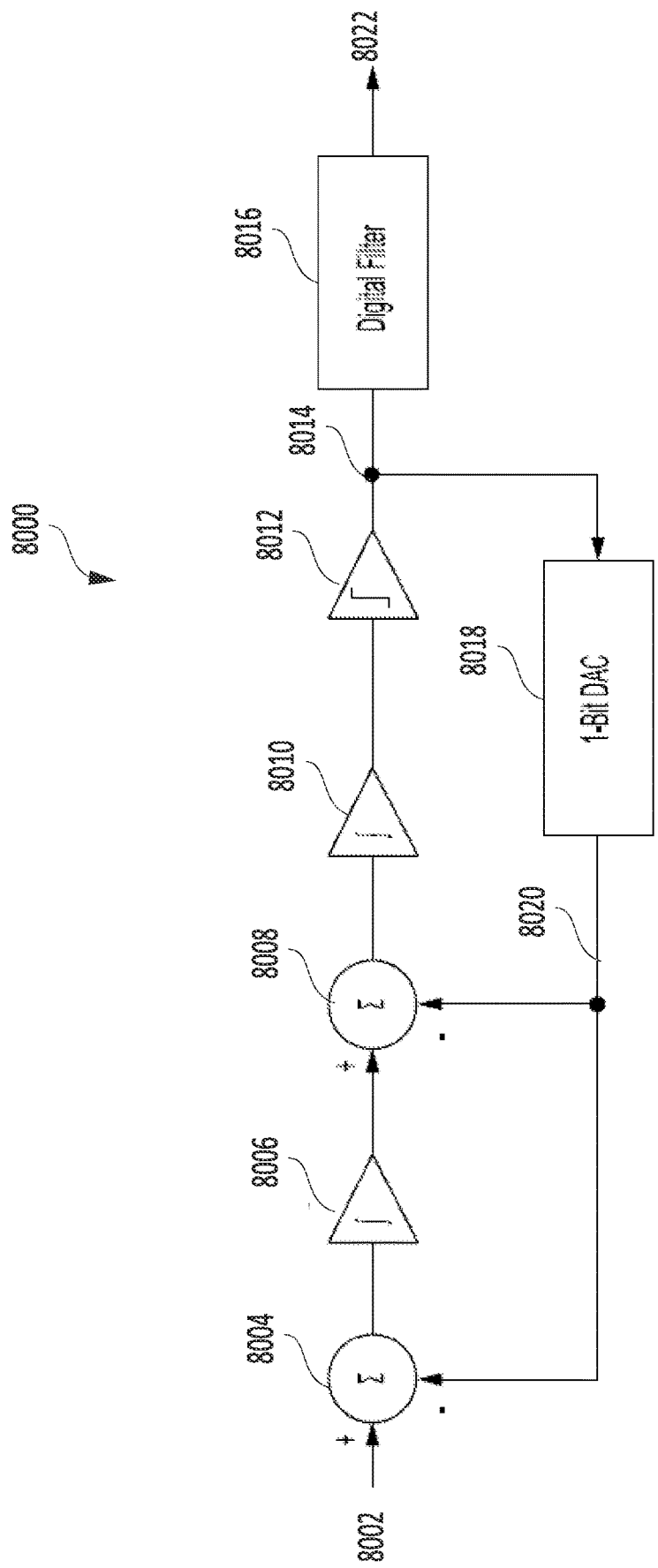
FIG. 15 illustrates a block diagram of one example of a delta-sigma modulation (DSM) based bit-stream controller according to one aspect of this disclosure.

In some aspects, variation to the waveform of the PWM signal (either as current or voltage to the motor) may include the use of a delta-sigma modulation (DSM) based bit-stream controller to a drive a motor. The DSM may essentially be configured as an analog output to generate a quasi-PWM signal in hardware. FIG. 15 illustrates a block diagram of one example of a DSM controller 8000. In the example of the DSM controller 8000, a signal input 8002 enters the positive branch of a first summer 8004. The output of the first summer 8004 is sourced to a first signal integrator 8006. The output of the first signal integrator 8006 is used in the positive branch of a second summer 8008. The output of the second summer 8008 is integrated by second signal integrator 8010. The output of the second signal integrator 8010 becomes the input of a comparator 8012. It may be understood that the signal input 8002, and the outputs of the first summer 8004, first signal integrator 8006, the second summer 8008, and the second signal integrator 8010 are all analog signals. The output of the comparator 8012 is a digitized signal ranging from a first (low) voltage to a second (high) voltage. The output of the comparator 8012 becomes an input to both a digital filter 8016 and a 1-bit digital-to-analog converter (DAC) 8018. The DAC output 8020 is used in a negative feedback manner at the negative branches of both the first summer 8004 and the second summer 8008. The output 8022 of the digital filter 8016 may be used as a motor control signal.

Figure 16:
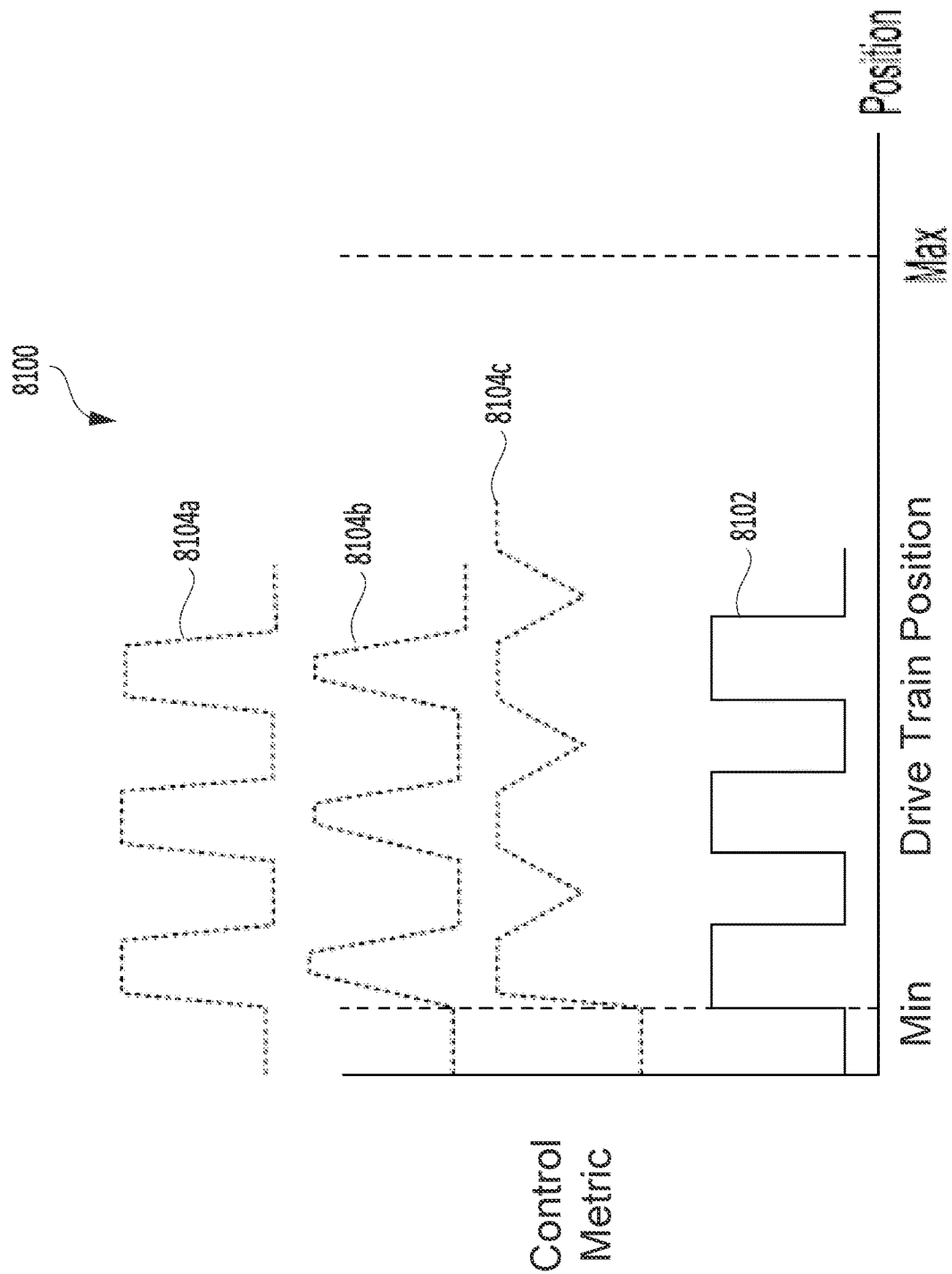
FIG. 16 illustrates a graph of irregular pulse-width modulation (PWM) motor control signals according to one aspect of this disclosure.

The DSM signal may be used to control the waveform shape of a motor control signal to compensate for changes in motor, gear, or drive train performance due to friction, changes in component tolerance, component fit, or wear. The adjusted motor control signal may be characterized as an irregular PWM which may be used to simulate a ramped response (instead of traditional sinusoidal) to drive a motor. FIG. 16 illustrates a graph 8100 of some irregular PWM motor control signals compared to a desired drive train component response. The y-axis of the graph 8100 represents any control metric such as component speed, motor signal amplitude or current, or similar. The x-axis of graph 8100 represents the motion of the drive train component from its minimal position (Min) to its maximum position (Max). The idealized waveform 8102 is a square wave of drive train component motion corresponding to a square wave current input to the motor. Irregular PWM wave signals 8104a, 8104b, and 8104c may overcome the non-idealities of the drive train component motion (due to friction, stiction, and other effects disclosed above). As a result, the irregular PWM wave signals 8104a, 8104b, and 8104c may result in better control of the drive train component motion.

In some aspects, the irregular PWM wave signals may be used intermittently in addition to the regular PWM wave signals. For example, the irregular PWM wave signals may be used only when the drive train components are moving within a portion of their complete range of motion. Thus, the irregular PWM wave signal may be used when a drive train component corresponds to a sub-system operating within a lockout zone and not when the sub-system is operating within the rest of the range of motion. In one non-limiting example in the last 0.02″ of closure tube stroke of a tissue cutting blade with respect to the first 0.23″.

Alternatively, the irregular PWM wave signals may be used throughout the entire range of motion of the drive train components. Additionally, the pulse shape of the irregular PWM wave signals may be adjusted over time. Non-limiting examples of pulse shape changes may include adjusting a leading edge of an irregular PWM wave signal differently than a trailing edge of the signal (for example, a triangular rising edge versus a square trailing edge.) Such different edge shapes may work to compensate against frictional loss at the beginning of the motion versus working with frictional losses at the end of the motion. Thus, the leading edge of the signal describes the rising profile of the "on" time of the motor, while the trailing edge of the signal describes the falling profile from the "on" time of the motor. These asymmetric adjustments to the motor signal profile may be used for tissues that may respond to varies types of leading and trailing edge motions of the tissue cutting blade. The powered surgical stapling system may detect the slope of the leading or trailing signals which indicate the system response based on the set profile. The powered surgical stapling system may then adjust the next profile to react to the system and provide increased control performance to benefit patient outcomes.

Figure 17:
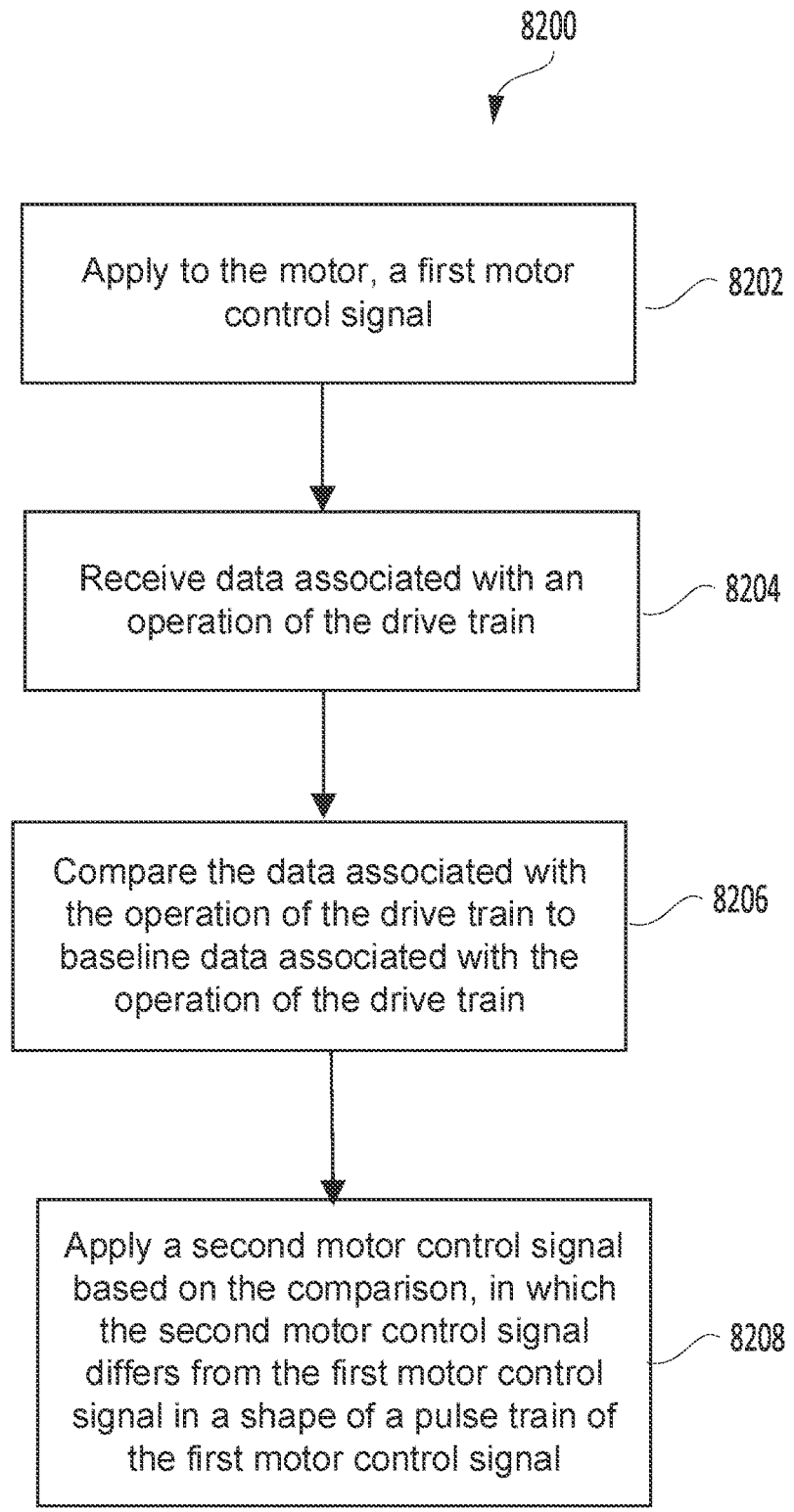
FIG. 17 is a flow chart of a method of controlling a motor in a powered surgical stapling system based on changing a shape of a motor control signal according to one aspect of this disclosure.

FIG. 17 depicts a flow chart 8200 of a method of controlling a motor in a powered surgical stapling system based on changing a shape of a motor control signal. A motor controller may apply 8202 a first motor control signal, for example a square wave PWM control signal. The motor controller may then receive 8204 data associated with an operation of one or more components of the drive train. Such data may include, without limitation, a position, a speed, an acceleration, or a deceleration of one or more components of the drive train throughout their respective motions. Such data may be obtained from sensors configured to detect these data, such as positional sensors. The motor controller may compare 8206 the data associated with the operation of the drive train to baseline data associated with the operation of the drive train. Such baseline data may be acquired either from manufacturer testing or acceptance trials, or may be obtained from the powered surgical stapling system during its initial use. The motor controller may apply 8208 a second motor control signal based on the comparison. The second motor control signal may differ from the first motor control signal in a pulse train shape from the first motor control signal. The change in pulse train shape may reflect a change in pulse amplitude, a change in a pulse leading edge, a change in a trailing edge, or other change in the pulse train shape. As discussed above, in some aspects, such a change may result in an irregular PWM control signal.

In some aspects, the data associated with an operation of the drive train may include data associated with a frictional loss of the drive train, an acceleration response of the drive train, a deceleration response of the drive train, or mechanical harmonics of the drive train.

In some additional aspects, applying the first motor control signal may include using a delta-sigma modulation based bit-stream controller to generate the motor control signal. In alternative aspects, applying the second motor control signal may include using a delta-sigma modulation based bit-stream controller to generate the motor control signal.

In yet another aspect, applying the second motor control signal may include adjusting a PID control parameter, triggering a delay of a dynamic braking function, changing a level or a function window around a triggering threshold, adjusting a power applied to the motor from the motor power supply, or adjusting a pulse-width modulation signal applied to the motor. In a non-limiting example, adjusting a pulse-width modulation signal applied to the motor may include adjusting a shape of the pulse-width modulation signal rising portion, maximum amplitude portion, or falling portion.

In some further aspects, it may be useful to characterize one or more functions of the sub-systems of the powered surgical stapling system during operation. Such characterizations may be useful if a fault condition or an anomalous behavior is detected during the course of a surgical procedure. An example of a fault condition may include, without limitation, a stall condition in the operation for example of a tissue cutting knife, or in a rotation motion about an articulation joint. The motor control signal may be reduced under load, and a perturbation signal at a known frequency may be applied to the motor in order to extract drive train loading information when a motor is in a stalled or full torque condition. This perturbation signal may be introduced to the regular motor control signal during the operation of the drive trains in order to interrogate combined sub-system component loss.

One type of perturbation signal may be characterized as a "load dithering" signal of the system. A "dithering" signal may be one which may cause a sub-system component to alternately operate in a forward and reverse direction at a frequency higher than a standard frequency of motion. The motor controller may use this signal to derive loading information of the system based on the motor operations. "Load dithering" or load fluctuation could be used to determine the amount of current used by the motor, and therefore characterize the load on the drive train. Such motor loading fluctuation may be used while the drive train is moving to also interrogate combined drive train component loss (for example, how fast the entire drive train slows when the motor load is reduced by a predetermined amount). Additionally, inertial aspects of the drive train may be determined. An example of the inertial aspects may include how fast the system re-accelerates given a known motor signal input power from an initial slower speed to a pre-set higher speed. The dithering signal may be applied when the drive train is driven into a portion of the stroke in which the system is unable to move. Exemplary conditions resulting in stall conditions may include driving the tissue cutting blade into a lockout tab or into the fully retracted—proximal—position. Similarly, the inertia of the tissue cutting blade sub-system drive train may be characterized in the portion of the tissue cutting blade sub-system drive train motion where there is not additive loss, for example at the first 0.150″ of the drive train travel prior to engagement with the anvil cam while the tissue cutting blade remains in the anvil pocket. Analysis of the response to the dithering signal under such conditions may help characterize motor stall conditions, and may be used to update motor and/or drive operational calibration.

As disclosed above, a perturbation signal may be imposed on a typical motor control signal in order to characterize the operation of one or more sub-systems of the powered surgical stapling system. A "dithering" signal has been disclosed above. Another type of signal may be a "chirp" signal. A chirp signal may be considered as a short duration electrical signal in which the signal frequency increases and/or decreases over time. A chirp signal may be used to characterize a system response over the range of frequencies comprising the chirp. As with the dithering signal, the chirp signal may be overlaid on the motor control signal during operations of the motor. Alternatively, the term chirp is used interchangeably with a frequency swept signal. The change in frequency arising from the chirp signal may be coupled with the PWM motor control signal generated by the motor controller in order to interrogate differences of the motor output at different speed and torque performance levels. The response of the motor may allow a diagnosis of the system stability and mechanical elements of the drive system over a range of frequencies. A spectrum analysis of the motor response, such as speed, acceleration, deceleration, or torque may be monitored for to determine, for example, inertia, damping, losses, backlash, and tolerance slope with a threshold of the return signal being used to determine if any adjustments to the motor control signal are necessary. In some aspects, the dithering signal may be considered a type of chirp signal.

Figure 18:
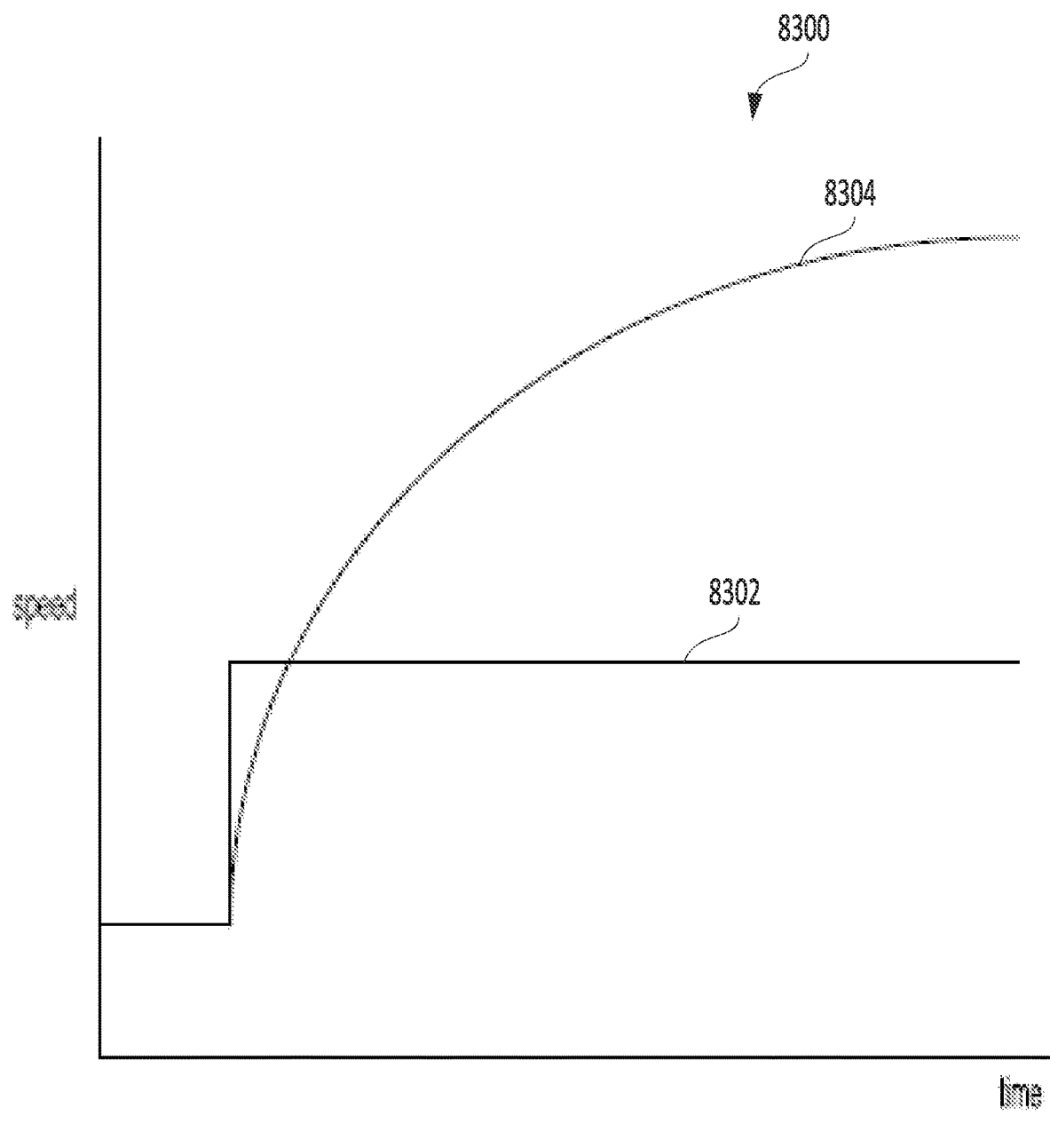
FIG. 18 illustrates a graph of a response of motor speed to the application of a step-function signal over time according to one aspect of this disclosure.

In another aspect, the response of a motor or drive train of a powered surgical stapling system may be determined by the application of a step-function signal to the motor. A step-function signal may be used to characterize motor response latency to improve the estimation of a future input speed target. The motor response to the step-function may be measured as well as the response of any components of a drive train in mechanical communication with the motor. In one non-limiting example, changes in the motor or drive train component speed over a time period after the step-function signal is applied may be measured. FIG. 18 illustrates a graph 8300 of a response of motor speed 8304 to the application of a step-function signal 8302 over time. In another example, a measurement of a time delay in response to the step-function signal of the motor and/or drive train components may also be analyzed. The time delay of the response of the motor to the applied step-function signal may characterize the electrical dynamics of the motor such as the resistance and/or inductance of the motor windings. The motor winding inductance may slow down the overall response of the system. Additionally, the motor mechanical dynamics may be assessed, such as rotor inertia and/or friction. An analysis of the motor response to the step-function signal may also indicate that the motor shaft is not perfectly straight, which may lead to additional friction to the system. A non-linearity of the motor shaft may also impact the inertia of the system.

In some aspects, the motors used in the powered surgical stapling system may include DC brushed motors. The brushes are used to transfer energy from the motor control signal to through a motor commutator. A commutator may be a rotary electrical switch that periodically reverses the current direction between the rotor and the external circuit. The electrical brushes may press against the commutator, making sliding contact with successive segments of the commutator as it rotates. The windings (coils of wire) on the armature are connected to the commutator segments. Variations in the brush pressure can cause variations to the friction of the system. Further, changes in the shape of the motor brushes may change the amount of current supplied to the commutator. Additionally, changes in brush shape may increase the friction between the brushes and the commutator, thereby effecting motor performance. In one aspect, the contact between the brush and the commutator may be intermittent ("brush bounce"). As a result of brush bounce, the brush may partially or entirely fail to make electrical contact with the commutator. As a result, current flow to the commutator may be reduced, modulated, or even interrupted. Thereby resulting in inconsistent motor torque generating capability.

Figure 20:
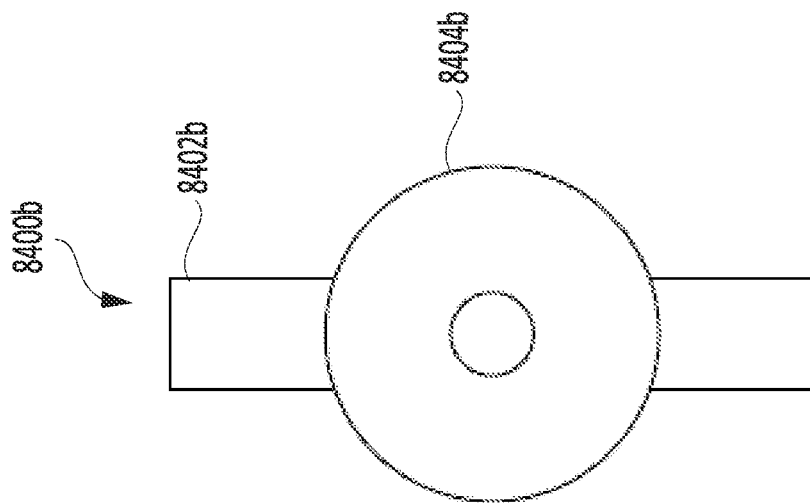
FIG. 20 illustrates a DC brushed motor having worn brushes according to one aspect of this disclosure.
Figure 19:
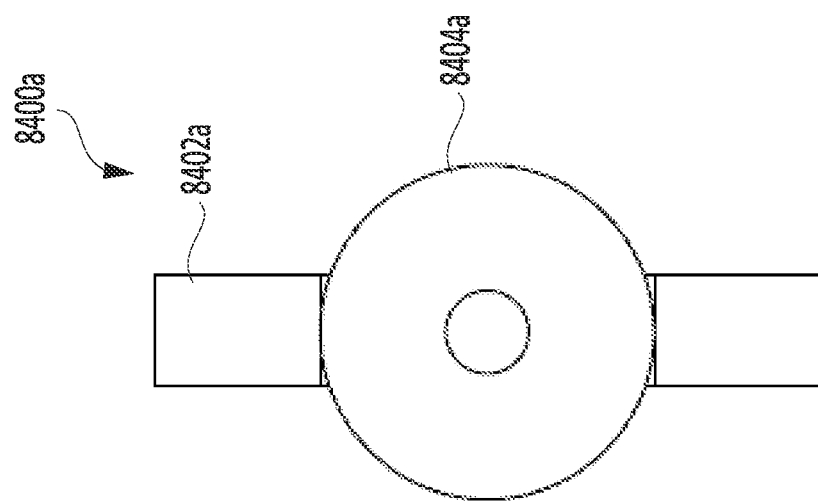
FIG. 19 illustrates a DC brushed motor having un-worn brushes according to one aspect of this disclosure.

FIGS. 19 and 20 illustrate DC brushed motors including their brushes and commutators. DC brushed motor 8400a includes an un-worn brush 8402a in contact with a commutator 8404a. DC brushed motor 8400b includes a worn brush 8402b in contact with a commutator 8404b. It can be observed that the un-worn brush 8402a is flat and makes a single point of electrical and mechanical contact with the commutator 8404a. The single point of contact is the only point of contact permitting the current to flow through each of a successive segment of the commutator 8404a as it rotates. The worn brush 8402b is rounded and can make multiple electrical and mechanical contacts with the multiple segments of the commutator 8404b as it rotates. It may be recognized that the multiple contacts may result in the worn brush having electrical contact with multiple successive segments of the commutator 8404b simultaneously. This may impact the smoothness of rotor turning.

In one aspect, powered surgical stapling system may include a motor gear reducer assembly in mechanical communication with a motor shaft. Before being assembled into the surgical stapling system, the motor gear reducer assembly and its associated motor may be tested using, for example, a step-function input, and characteristics related to the motor with motor gear reducer assembly operation may be collected. Such initial motor with motor gear reducer assembly data may include the output speed, current to run at no load, and numerous other electrical parameters of the motor. Mechanical aspects like gear backlash and varying frictions during operation can also be collected. Once assembled into the device, the motor with motor gear reducer assembly may be integrated into the larger mechanical system. By applying power to the motor with motor gear reducer assembly and re-running the same characterizing tests—in both the forward and reverse directions—information about the system including the motor can be characterized. A comparison of the initial motor with motor gear reducer assembly data against the data obtained from the motor with motor gear reducer assembly in the complete surgical stapling system after use can shed light on the overall system frictional requirements. In some aspects, the characterized frictional response of the motor with motor gear reducer assembly may differ between the forward and reverse directions. It is understood that a cutting blade moving in the forward direction may encounter additional friction due to the interaction of the tissue cutting blade and the tissue. However, when the tissue cutting blade operates in the reverse direction, away from the tissue, it is expected that the blade motion friction should be reduced since there is no tissue operating against the tissue cutting blade. The initial forward and reverse frictional response of the tissue cutting blade in an unused device may be used to set the threshold values for the operation of the tissue cutting blade. In this manner, a user of the powered surgical stapling system may be alerted to additional friction due to the tissue being cut, and not to friction inherent in the tissue cutting blade sub-system.

It may be generally understood that initial operations of the various sub-systems of a powered surgical stapling system may be used to gather initial data about the motor, motor gear reducer assembly, and drive train components. The motor may be coupled to each of the separate sub-systems—such as the articulation sub-system and the tissue blade sub-system—to characterize motor and/or motor gear reducer assemblies. The motor may be operated at various speeds and directions to characterize their operations when coupled to the sub-systems. Parameters that can characterize the motor and/or motor gear reducer assembly may include, without limitation, backlash and latency from the receipt of the motor control signal to the operations of the mechanical components. By characterizing these timings, the motor controller algorithms may be adjusted to minimize these latencies.

Figure 21:
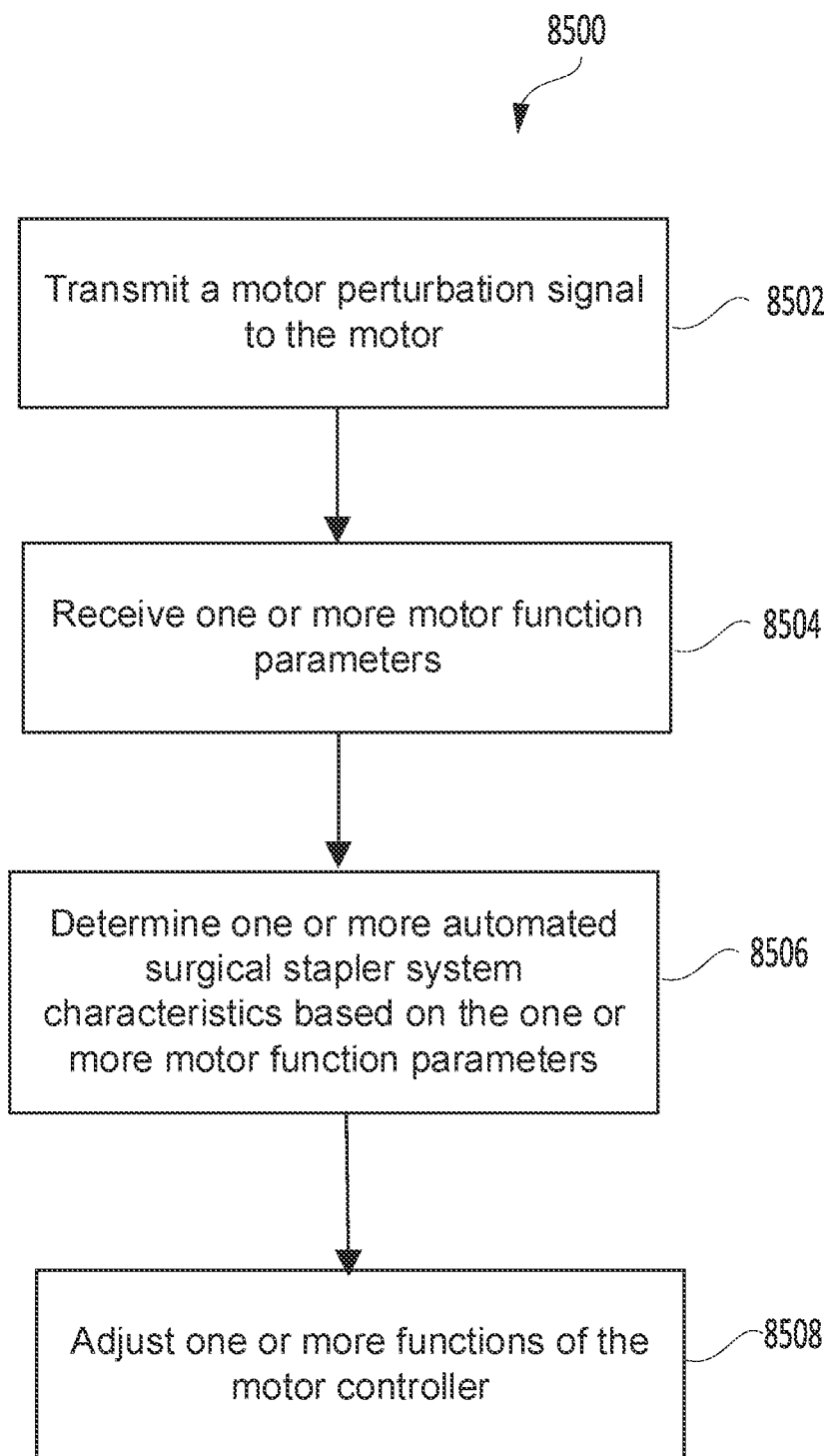
FIG. 21 is a flow chart of a method of characterizing a motor in a powered surgical stapling system, according to one aspect of this disclosure.

FIG. 21 depicts a flow chart 8500 of a method of characterizing a motor in a powered surgical stapling system. The motor controller may transmit 8502 to the motor a motor a perturbation signal. In one example, the perturbation signal may include a step signal. In another example, the perturbation signal may be transmitted to the motor along with the operational motor control signal. In some examples, the perturbation signal transmitted with the operational motor control signal may include a chirp signal or a dithering signal. The motor controller may receive 8504 one or more motor function parameters. Non-limiting examples of the motor function parameters may include a motor latency parameter, a motor frequency dependent torque parameter, or a motor current draw parameter. The motor controller may determine 8506 one or more automated surgical stapler system characteristics based on the one or more motor function parameters. Non-limiting examples of the automated surgical stapler system characteristic may include a system friction, a system inertia, a system backlash, or a system latency. The motor controller may then adjust 8508 one or more functions of the motor controller. Examples of motor controller functions that may be adjusted in response to the system characteristics may include, without limitation, a motor drive pulse-width modulation phase, a motor drive frequency, or a motor drive current.

In some aspects, the motor or motors of a powered surgical stapling system may include stepper motors. Stepper motors are digitally controlled brushless DC motors that divide a full rotation of the rotor into a number of equal steps. The stepper motor includes a number of electromagnets arranged around a central rotor. As each electromagnet is energized, the rotor rotates a fixed amount. When the electromagnets are energized in turn, for example by a series of pulse trains, the rotor turns synchronously with the energized electromagnet. A stepper motor can be characterized according to several different torque values. In one aspect, a pull-in torque may represent the amount of torque in which the motor may move the load without acceleration. Generally a pull-in torque-speed curve illustrates the speeds at which the motor may start, stop and reverse without losing synchronicity with the incoming pulses. A pull-out torque may relate to the amount of torque the motor may dynamically produce at various speeds. Generally this torque may be represented in conventional torque-speed curves. If the motor exceeds this torque, it loses synchronicity with the incoming pulses and stalls. A holding torque may represent the amount of external torque which must be exerted on the motor shaft when the motor is at full rated current and is at rest (zero speed). This condition may be met when only a single electromagnet is energized, and the motor does not move. This is a static torque and is generally not depicted on a torque-speed curve. The holding torque is generally about 20% higher than the low speed torque of a dynamic torque-speed curve. Finally, a detent torque represents the amount of torque required to move the motor rotor when the motor is not energized. This condition is met when no current passes through the winding and the motor is at rest.

Figure 22:
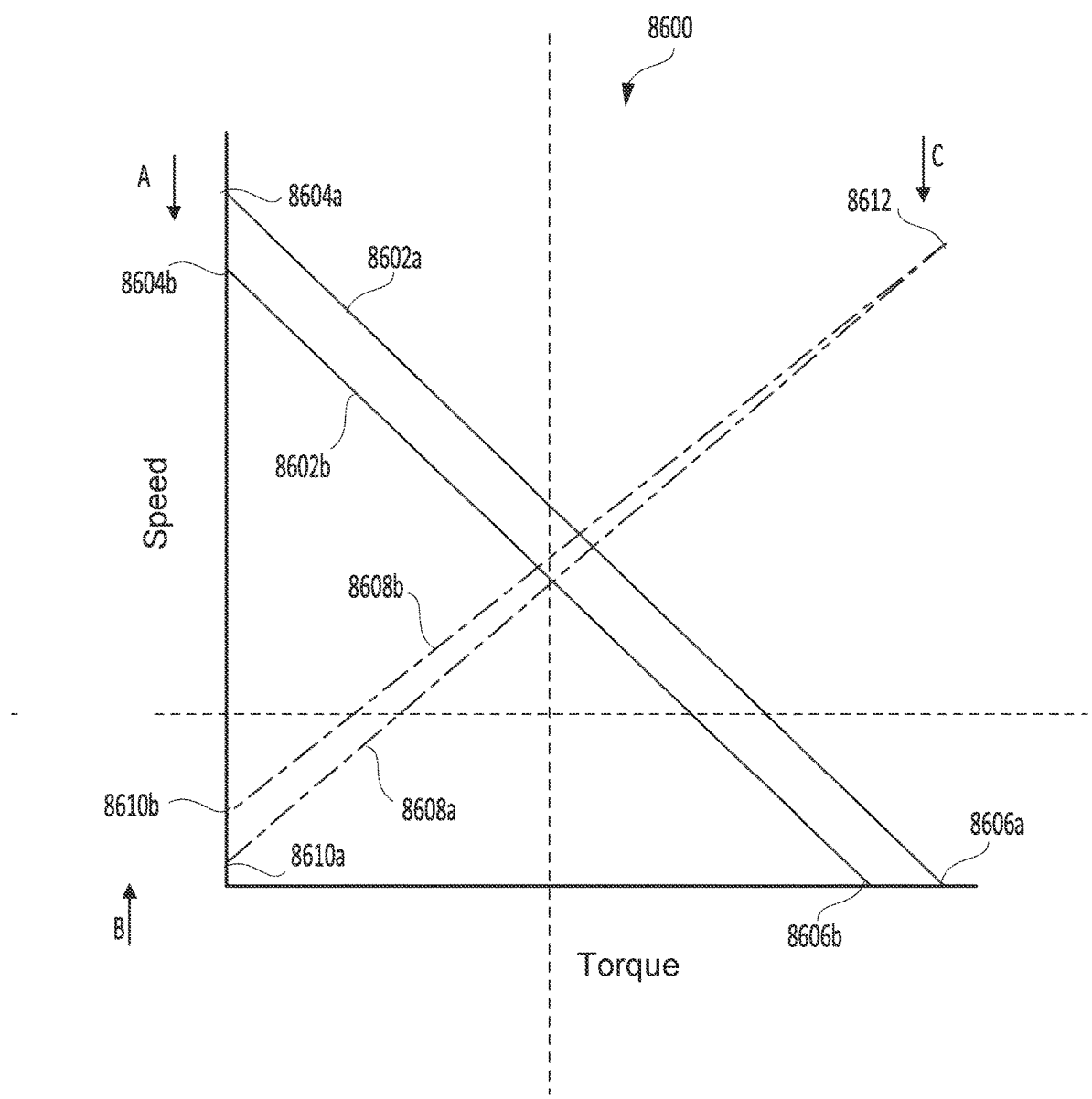
FIG. 22 illustrates a graph of stepper motor speed versus torque curves according to one aspect of this disclosure.

FIG. 22 is a graph 8600 that illustrates various speed versus torque curves for a stepper motor that may be used in a powered surgical stapling system. Curves 8602*a* and 8602*b* depict maximum speed versus torque curves for a stepper motor under various conditions. As discussed above, curves 8602*a* and 8602*b* may represent the stepper motor pull-out torque. An initial maximum speed versus torque curve 8602*a* illustrates a maximum speed attainable by the motor under various load conditions. Under a no-load condition 8604*a*, the motor can attain its maximum speed. As the load increases—requiring the motor to generate more torque—the maximum speed may decrease until the motor attains a stall torque 8606*a*. The stall torque 8606*a* occurs when the motor is unable to move due to the load. The initial speed versus torque curve 8602 may be obtained from a motor operating alone. As an example, the initial speed versus torque curve 8602 may be a speed versus torque curve supplied by the motor manufacturer. Parameters or data related to the initial speed versus torque curve 8602 may be obtained from the manufacturer and stored in a memory unit of the motor controller. Alternatively, the parameters or data related to the initial speed versus torque curve 8602 may be obtained through independent measurements of the motor alone or with the motor gear reducing assembly. The data may be stored directly in the memory unit of the motor controller or may be read from an external memory device, such as from a chip or thumb drive, or may be down-loaded from a server from a remote communication system.

Once the motor is installed in a powered surgical stapling system, the motor is required to move the various components of the drive trains. As the components of the drive trains have various frictional characteristics, the speed versus torque curve 8602*b* of the complete mechanical sub-system may be shifted down (arrow A) to lower values. Further, as the powered surgical stapling system is used, additional friction and wear may develop in the drive train components further reducing the speed versus torque curve 8602*b*. It may be understood that the motor and/or motor gear reducer assembly may suffer from wear, including, as one non-limiting example, loss of motor shaft, rotor, or gear reducer assembly concentricity. All of these effects may further reduce the speed versus torque curve 8602*b*. Reduction of the speed versus torque curve 8602*b* may result in both a lowering of the maximum speed under no-load condition 8604*b* and the maximum torque achievable (as measured at the stall torque 8606*b*).

Curves 8608*a,b* represent minimum speed (or current) versus torque curves. These curves illustrate the minimum speed or current the motor requires to generate a specific amount of torque. Curve 8608*a* may represent the minimum speed or current required to generate torque for a motor alone or only with the motor gear reducer assembly. Under no-load conditions, 8610*a*, the motor may require a minimum speed or current to overcome its internal resistance. In some aspects, the no-load minimum speed or current 8610*a* may represent the speed or current required to overcome the detent torque. The minimum speed or current able to generate the maximum torque 8612 may be related to the stall torque.

Once the motor is installed in a powered surgical stapling system, the motor is required to move the various components of the drive trains. As the components of the drive trains have various frictional characteristics, the minimum speed or current versus torque curve 8608*b* of the complete mechanical sub-system may be shifted upwards (arrow B) to higher values. Thus, even under no-load conditions 8610*b*, the minimum speed or current required to overcome the complete drive train resistance will be increased over the no-load condition 8610*a* of the minimum speed or current versus torque curve 8608*a* of the motor alone. Further, as the powered surgical stapling system is used, additional friction and wear may develop in the drive train components further increasing the minimum speed or current versus torque curve 8608*b*. It may be understood that the motor and/or motor gear reducer assembly may suffer from wear, including, as one non-limiting example, loss of motor shaft, rotor, or gear reducer assembly concentricity. All of these effects may further increase the minimum speed or current versus torque curve 8608*b*. An increase of the minimum speed or current versus torque curve 8608*b* may result in an increase of the minimum speed or current under no-load condition 8610*b* although the minimum speed or current at maximum torque 8612 may not be affected. However, the minimum current during motor use may result in motor coil heating. As the coils heat, their electrical resistance may increase, thereby reducing the amount of current through the motor windings. The reduction of motor current due to temperature-dependent changes in winding resistance may result in a decrease in the minimum speed or current at maximum torque 8612, as indicated by arrow C.

Figure 23:
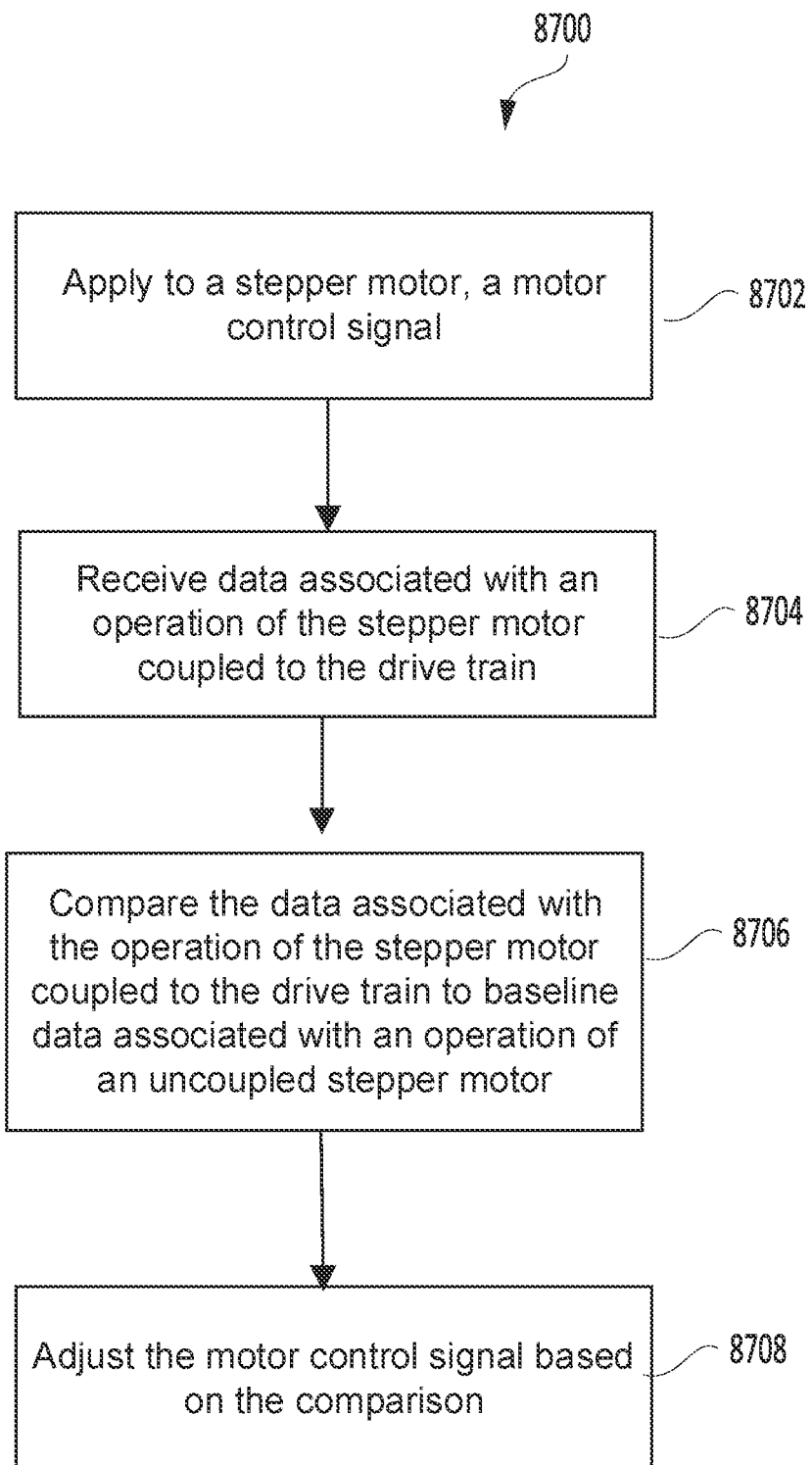
FIG. 23 is a flow chart of a method of controlling a stepper motor in a powered surgical stapling system according to one aspect of this disclosure.

FIG. 23 depicts a flow chart 8700 of a method of controlling a stepper motor in a powered surgical stapling system. The motor controller may apply 8702 to the stepper motor a motor control signal. The motor controller may receive 8704 data associated with an operation of the stepper motor coupled to the drive train. The motor controller may compare 8706 the data associated with the operation of the stepper motor coupled to the drive train to baseline data associated with an operation of an uncoupled stepper motor. In some non-limiting examples, the baseline data may include one or more of a motor pull-in torque, a motor pull-out torque, or a motor holding torque of the uncoupled stepper motor. The motor controller may then adjust 8708 the motor control signal based on the comparison. Examples of motor controller signals that may be adjusted in response to the comparison may include, without limitation, a motor drive frequency, a motor drive pulse width, or a motor drive current.

As disclosed above, a motor in a powered surgical stapling system may be coupled to one or more drive train components. In some non-limiting examples, the drive train may include a drive train to actuate a tissue cutting blade or a drive train to actuate an articulation joint. The drive trains may be composed of multiple components mechanically coupled to each other. In some aspects, the motor may drive the drive trains directly, or the motor may drive the drive trains through a motor gear reducer assembly. It may be recognized that each mechanical component of the drive train may exhibit its own mechanical operation which may suffer from friction, stiction, and backlash associated with the shape and linkage of the component. While knowledge of the overall operation of the drive train is useful, it may be important to characterize anomalous operations of each of the drive train components in order to better characterize the entire motor plus drive train assembly. Thus, differential measure and analysis of at least two separate portions of a linked or coupled drive train may insure better mechanical operation (verification of response) or quantify losses/inefficiencies that may differ between an ideal or intended response and an actual response of the system.

In some aspects, the motor controller algorithm may include detection of individual device drive train component properties. The powered surgical stapling system may monitor sub-system drive train component operations relative to input motor control signals from data obtained from sensors of the drive train component motions. The motor controller algorithm may then adjust the motor control signals based on the individual system response relative to pre-established baseline performance. In some non-limiting aspects, the monitored responses may be frictional loss, acceleration or deceleration responses to a stepped input signal, PID control variation, harmonics of the system, noise, or force versus speed. The adjustments to the motor controller algorithms may include adjustments to the PID control parameters, triggering delay of dynamic braking, level or function window around the triggering thresholds, motor power, motor current, motor voltage, or PWM signal characteristics.

In some aspects, multiple sensors may be configured to monitor separate components of the same drive system to enable the system to detect slop, backlash, or losses for each component. In one non-limiting example, rotational data from a rotary encoder coupled to the shaft of the motor may be compared to rotational data of an encoder coupled to the motor gear reducing assembly. A firing rack may be coupled to the motor gear reducing assembly. The comparison between the data from the motor shaft encoder and the motor gear reducing assembly may be used to determine the backlash, slop, clearances, and other losses of the motor gear reducing assembly. The comparison may result in better compensation by the motor controller, which may adjust one or more of the functions of the motor controller including, without limitation, a target motor speed, a PID duty cycle of the PWM, a voltage limit, or a current limit. By adjusting the one or more motor controller functions, the motor controller may cause the motor to operate drive train at desired operational speeds, braking, and holdings.

In some aspects, a sensor may be coupled to a drive bar actuated by the motor. The encoder associated with the motor shaft may provide rotational data for the operation of the motor, while the drive bar sensor may sense the linear actuation of the drive bar. The data from the encoder and the drive bar sensor may be used to calculate a mechanical transfer function between the motor rotational speeds to the drive bar linear movement. The transfer function can help determine the latency of the motor movement to the drive bar response. The resulting analysis may provide a measure of gear "slop" or backlash, and permit a determination of the requirements to take up the backlash in the gear train. In this manner, the motor response latency can be characterized to improve the estimation of future input speed target by the motor controller algorithms.

In another aspect, sensors may be associated with the clamping trigger and the anvil/channel area. The motor controller may determine the movement and timing of the closure trigger. The motor controller may then sense the movements of the anvil. With these data, the motor controller can determine a time delay between the input of the closure trigger and the movement of the anvil. Such data may be obtained for both the opening and closing functions of the anvil. As disclosed above, a transfer function based on the sensor data and the motor rotation data may be used to estimate the motor rotational speed in order to reduce position/velocity errors of the device.

Figure 24:
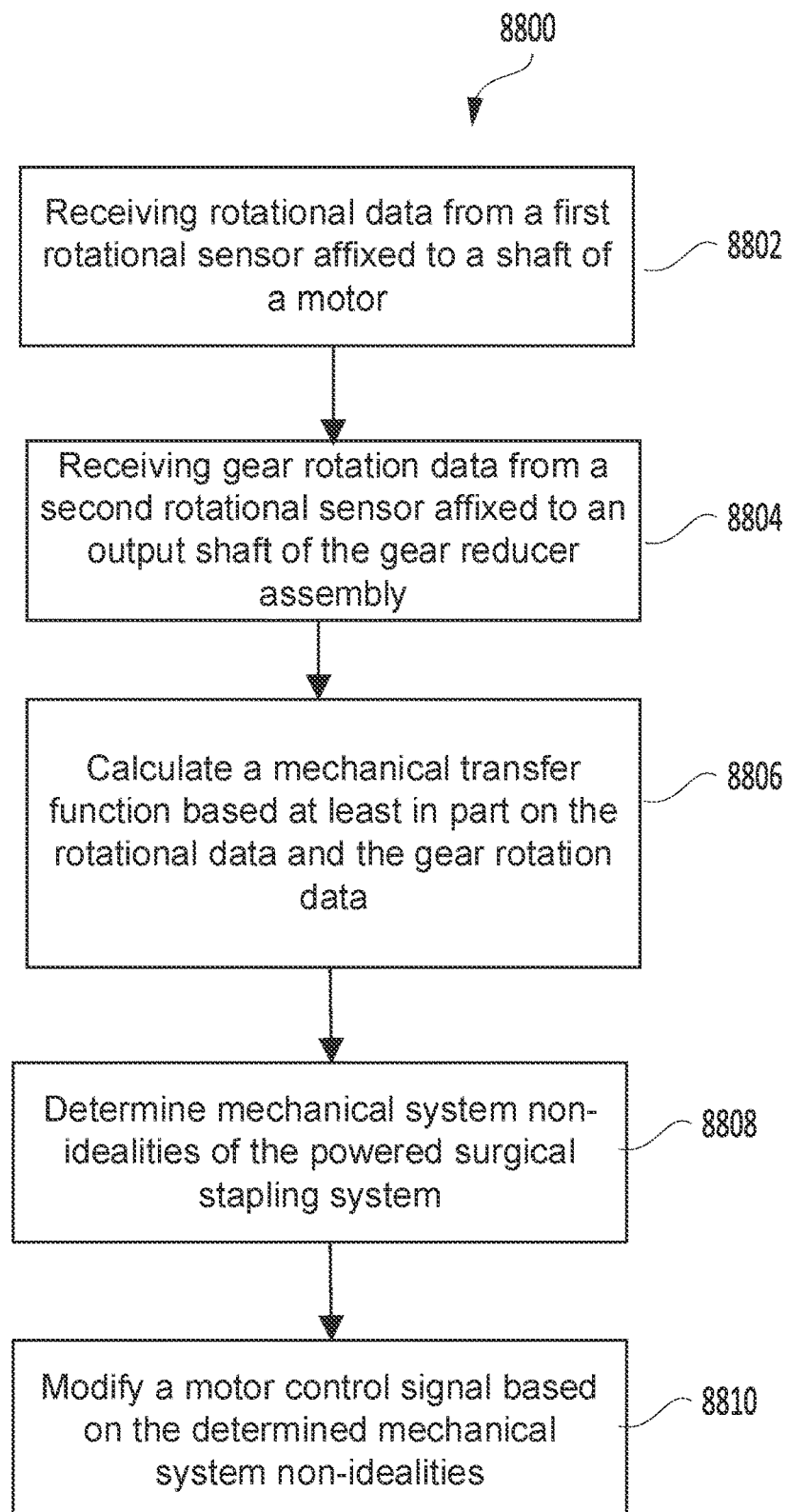
FIG. 24 is a flow chart of a method of controlling a motor in a powered surgical stapling system based on data received from multiple sensors of the operation of sub-system components, according to one aspect of this disclosure.

FIG. 24 depicts a flow chart 8800 of a method of controlling a motor in a powered surgical stapling system based on data received from multiple sensors of the operation of sub-system components. A motor controller may receive 8802 rotational data from a first rotational sensor affixed to a shaft of the motor. The first rotational sensor may be, for example, a rotary encoder positional sensor. The motor controller may then receive 8804 gear rotation data from a second rotational sensor affixed to an output shaft of the gear reducer assembly. Again, in some non-limiting examples, the second rotational sensor may be a rotary encoder positional sensor. Additional sensor data may also be received by the motor controller, such as trigger motion data from a motion sensor in mechanical communication with an anvil clamping trigger or anvil position data from an anvil position sensor. The motor controller may calculate 8806 a mechanical transfer function based at least in part on the rotational data and the gear rotation data. In some alternative aspects, the motor controller may also receive linear motion data from a sensor of a linear position of the drive bar. The motor controller may then calculate a second mechanical transfer function based at least in part on the rotational data, the gear rotation data, and the linear motion data. The motor controller may also include a motor response latency.

The motor controller may determine 8808 mechanical system non-idealities of the powered surgical stapling system. Mechanical non-idealities may include, without limitation, system component delays, backlash, gear slop, gear clearance, and a mechanical loss of the gear reducer assembly. The motor controller may modify 8810 a motor control signal based on the determined mechanical system non-idealities. In some aspects, the motor controller may modify one or more of a motor control signal voltage, a motor control signal current, and a motor control pulse duty cycle. In some additional aspects, the motor controller may receive trigger motion data from a motion sensor in mechanical communication with the anvil clamping trigger as well as anvil position data from an anvil position sensor. The motor controller may then determine a time delay between a motion of the anvil clamping trigger and a motion of the anvil.

As disclosed above, a powered surgical stapling system is composed of multiple mechanical and electrical subsystems. The components may include, without limitation, an end effector composed of a first jaw and a second jaw, in which the first jaw is configured to include a staple cartridge and the second jaw includes an anvil. The first and second jaws cooperatively deploy staples to a tissue grasped by the jaws when they close. The end effector may also include a blade or tissue cutting edge movable to sever the stapled tissue. The end effector may be mounted on a shaft assembly which may further include an articulation joint. The articulation joint may be configured to rotate about an articulation axis, thereby rotating the end effector about the articulation axis with respect to a longitudinal axis of the shaft assembly.

In some aspects, a user may cause the anvil to close on a tissue supported by the first jaw using a manual trigger mechanism. In some aspects, the tissue cutting edge may be driven by an electrically activated motor. In some other aspects, the articulation joint may be rotated either by the same electrically activated motor that drives the cutting edge, or a separate motor. The motor may be controlled by a combination of activation switches and one or more motor controllers through a series of motor control signals.

Thus, as disclosed above, the powered surgical stapling system is composed of a number of high-precision mechanical components working together to effect the stapling and cutting of the tissue. In some sub-systems, mechanical components may work together to cause the cutting edge to slide in a distal direction to cut tissue, and slide back to a home position once the cutting operation is completed. In some other sub-systems, mechanical components may work together to cause the articulation joint to rotate in a first direction and then back to a second position. These sub-systems may require the interaction of multiple mechanical linkages (drive-trains) with a motor with or without a gear reducer assembly. One or more sensors may be used to detect the types and speeds of the motions of the drive-trains for use as feed-back to a motor controller.

The motor controller may include one or more algorithms—implemented either in hardware, software, or firmware—designed to actuate the drive-trains in a manner responsive to the surgical environment. In one aspect, the surgical environment may reflect the type or thickness of a tissue grasped, stapled, and cut in the jaws. In another aspect, the surgical environment may reflect obstructions around the articulation joint. The motor controller should be configured to adjust the motor control signals so that the activation of the motor or motors may be optimized for the task at hand.

Additionally, the powered stapling system may be designed to proactively make small performance corrections to negate any performance deficiencies of a sub-system, such as the tissue cutting sub-system, the jaw-clamping sub-system, or the articulation sub-system. These adjustments may be gauged against past historical data from pervious cycles or anticipated for subsequent cycles based on the trending performance. These types of enhancements may normalize the performance of the device over repeated uses or normalize manufacturing deviations in performance between devices.

Time (age) and use may result in structural changes in the components of the drive-trains as well as in the motor or motors. Narrow elongated structures—such as the drive member, the intermediate firing shaft portion, the firing member, the articulation lock bar, the articulation rods, and the articulation system— may warp or bend with continued use. The teeth of the gears in the gear reducer assembly may chip, bend, or wear with use. In some aspects, plastic gears comprising the gear reducer assembly may become brittle and fracture with age. It may be understood that the sub-systems may become less responsive to the motor control signals unless the motor controller is able to adapt the motor control signals to the mechanical changes in the motors and drive-trains.

It is therefore understood that the motor controller should be able to adapt not only to changes in the surgical environmental, but also to the changes in the motor or motors and drive-train components as the powered surgical stapling system is used. Adaptation of the motor controller and motor control signals may result from comparative data of the motors and/or drive-train under different conditions or over time. In some non-limiting examples, such data may include operational data from the motors or sensors associated with the drive-trains. Thus, the motor controller may receive first data indicative of an operation of the motor operating under a first condition, receive second data indicative of an operation of the motor operating under a second condition, and adjust a motor control signal based on a difference between the first data and the second data.

Figure 25:
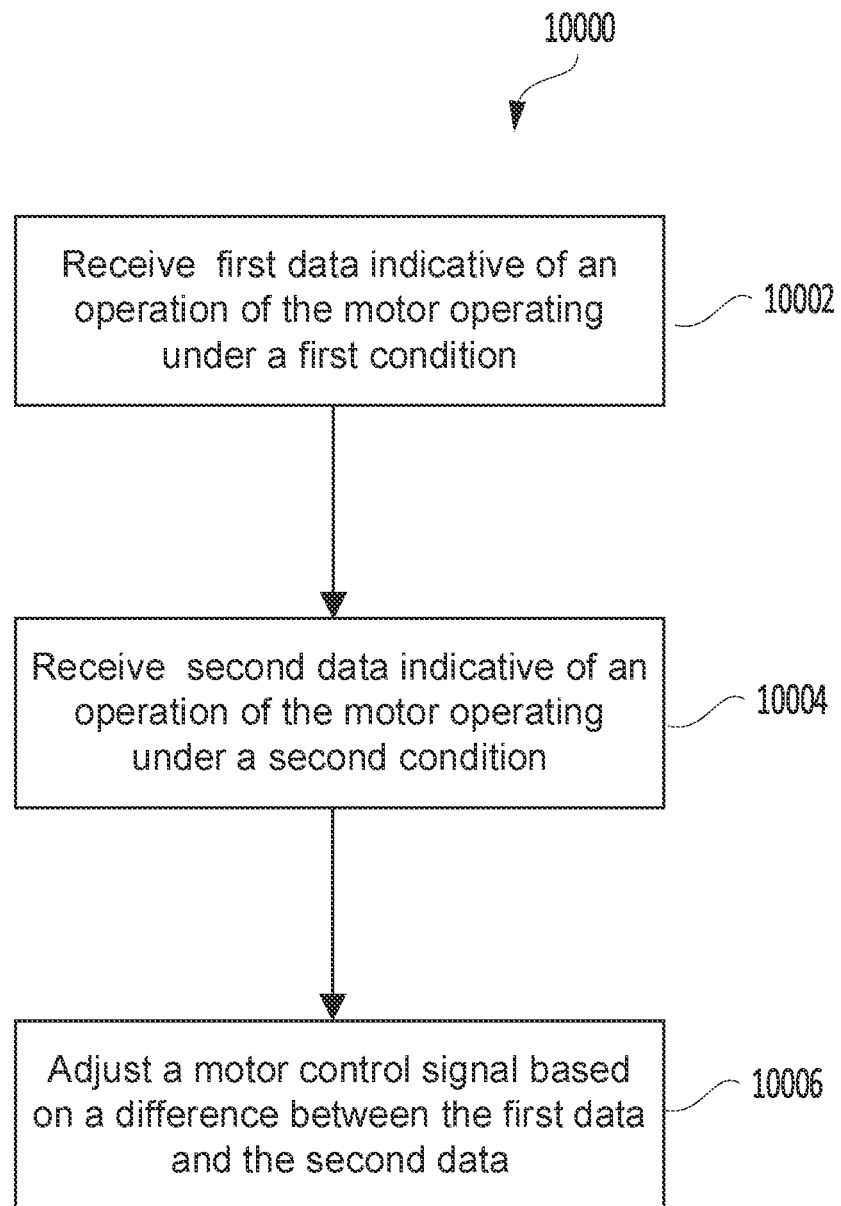
FIG. 25 is a flow chart of a method of adjusting a motor control signal based on motor operational data according to one aspect of this disclosure.

FIG. 25 depicts a flow chart 10000 of a method of controlling a motor in a powered surgical stapling system based on differential measurements of motor and/or drive-train operations. Thus, the motor controller may receive 10002 first data indicative of an operation of the motor operating under a first condition. Further, the motor controller may receive 10004 second data indicative of an operation of the motor operating under a second condition. The motor controller may then adjust 10006 a motor control signal, such as a pulse width modulation (PWM) signal, based on a difference between the first data and the second data.

In some aspects, a determination of motor and motor gear reducer assembly operations may be obtained from a first rotary encoder affixed to the motor drive shaft and a second rotary encoder affixed to the motor gear reducer assembly. In some aspects, the motor controller may receive first data including first rotational position data from the first rotary motion encoder mechanically associated with a shaft of the motor and first rotational position data from the second rotary motion encoder mechanically associated with an output of the motor gear reducer assembly. In some aspects, the motor controller may receive second data including second rotational position data from the first rotary motion encoder and second rotational position data from the second rotary motion encoder. The speed of the motor drive shaft and the motor gear reducer assembly may be measured from the respective encoders based on the change in positional output of the encoders over time. Thus, the motor controller may receive first data including one or more of first motor torque data or first motor speed data, and the second data indicative of the operation of the motor may include one or more of second motor torque data or second motor speed data.

Alternatively, the motor controller may receive first data including one or more of first motor gear reducer assembly torque data or first motor gear reducer assembly speed data, and the second data indicative of the operation of the motor gear reducer assembly data may include one or more of second motor gear reducer assembly torque data or second motor gear reducer assembly speed data. As a result, adjusting the motor control signal based on the difference between the first data and the second data may include adjusting the motor control signal based on a difference between the first rotational position data from the first rotary motion encoder and the first rotational position data from the second rotary motion encoder, or between the second rotational position data from the first rotary motion encoder and the second rotational position data from the second rotary motion encoder.

The speed of the motor drive shaft and the motor gear reducer assembly should be related by the gear-reduction ratio of the gear reducer assembly under no-load conditions. This may provide a no-load, maximum speed, minimum torque condition. Without load, the motor drive shaft output, as well as the output of the motor gear reducer assembly, should be in phase with the motor control signal. However, as the load increases, the motor drive shaft output or the output of the motor gear reducer assembly may shift in phase with respect to the motor control signal. As a result, the measured speed signals from either rotary encoder may deviate from the no-load conditions. Thus, in some aspects, the first data indicative of the operation of the motor operating under the first condition may include first data indicative of an operation of the motor in a mechanically unloaded condition, and the second data indicative of an operation of the motor operating under a second condition may include second data indicative of an operation of the motor in a mechanically loaded condition.

Similarly, the first data indicative of the operation of the motor gear reducer assembly operating under the first condition may include first data indicative of an operation of the motor gear reducer assembly in a mechanically unloaded condition, and the second data indicative of an operation of the motor gear reducer assembly operating under a second condition may include second data indicative of an operation of the motor gear reducer assembly in a mechanically loaded condition. A comparison thus may be made of the operations of the motor and/or motor gear reducer assembly between a mechanically un-loaded condition and a mechanically loaded condition.

The output speed of the motor gear reducer assembly may slow at a higher proportion than the motor speed signal phase. With increased mechanical wear, motor backlash due to gear take-up may increase. The increased backlash may also result in reduced speed of the motor gear reducer assembly. Thus, a comparison of the motor encoder data with the encoder data from the motor gear reducer assembly may be used to estimate output gear response, such as speed or torque, over time. The backlash may be measured under various loading conditions, including under no-load, as well as during a motor stall condition.

In other aspects, a comparison of motor characteristics under different conditions may include a measurement of current/power draw from each motor, motor temperature, motor acceleration/deceleration rates, and/or back electromagnetic force (EMF). These metrics may also be used to characterize changes in the motor operations, including, without limitation, output speed or torque.

In another aspect, physical measurements related to drive-train components may also be used to determine changes in motor and/or motor gear reducer assembly operations. Comparisons may be made of physical displacements, speed or positional losses, and component backlash associated with the components of the drive-train or drive-trains. For example, a drive-train operation may include positioning the components of drive-train at a known reset or re-configuration condition. In one aspect, a drive-train configured to actuate a tissue cutting blade may have a reset position in which the tissue cutting blade is located at a fully retracted position (proximal most position). In another aspect, a drive-train configured to rotate an end effector about an articulation joint may have a reset position in which a longitudinal axis of an end effector is aligned with a longitudinal axis of a shaft assembly (about a 180 degree angle between the longitudinal axis of the end effector and the longitudinal axis of the shaft assembly). In a further example, measurements of an angular motion of an articulation joint, a rate of change of the angular motion of the articulation joint, a location of a tissue cutting blade, or a rate of change of the location of the tissue cutting blade may be made using data obtained from relevant positional sensors over time. Thus, the first data indicative of the operation of the motor operating under the first condition may include first data indicative of one or more of an angular motion of the articulation joint, a rate of change of the angular motion of the articulation joint, a location of the tissue cutting blade, or a rate of change of the location of the tissue cutting blade, and the second data indicative of an operation of the motor operating under a second condition may include one or more of the angular motion of the articulation joint, the rate of change of the angular motion of the articulation joint, the location of the tissue cutting blade, or the rate of change of the location of the tissue cutting blade. These data may permit the motor controller to track changes in those parameters as the powered surgical stapling system is used. In a system that uses the same motor to drive two different drive-trains (for example the tissue cutting drive-train and the articulation motion drive-train), an exchange location which positions a first drive-train to a reset position before allowing the mechanical switch to engage a second drive-train could be used to monitor a "home position" over time. With these data, the motor controller may generate motor control signals of the motor speed and motor rotational position that are compensated for system variations over time.

As disclosed above, changes in data associated with the use of a powered stapling system may be used by the motor controller to update or change the algorithms used to control the operation of a motor in concert with a gear reducer assembly. Additional data, not associated with the active use of the device, may also be incorporated into the motor controller algorithms regarding the history of the device before deployment. Knowing the age of the device, shipping and storage conditions, and total run time of the components can all add valuable information to the system. Adjustments to the motor control signal based on such initial conditions may normalize the use of the powered stapling system by the surgeon over time and between devices. As a result, normalization of the device operation will keep surgical outcomes more consistent and predictable.

In one aspect, the first data received by the motor controller that is indicative of the operation of the motor under the first condition may include data indicative of an operation of the motor at initial manufacture. The second data received by the motor controller that is indicative of the operation of the motor under the second condition may include data indicative of an operation of the motor at some time after initial manufacture. Non-limiting examples of data indicative of an operation of the motor at some time after initial manufacture may include data obtained regarding a time that the powered surgical stapling system lies in storage, a total time of use of the powered surgical stapling system, a time between actuations of the tissue cutting blade, a time between rotations about the articulation joint, a total run-time between firings of the tissue cutting blade, a number of firings of the tissue cutting blade, a total time since build, and/or a total number of uses of the powered surgical stapling system.

The data indicative of an operation of the motor at initial manufacture may include any relevant electrical or mechanical data associated with the operation. Such data may include, without limitation, a starting current of the motor, a starting acceleration of the motor, a speed of the motor under no-load conditions, a time of motor operation for a complete actuation of the tissue cutting blade in a distal direction, a time of motor operation for a complete actuation of the tissue cutting blade in a proximal direction, a time of motor operation for a complete actuation of the tissue cutting blade in a proximal direction, a time of motor operation for a complete actuation of the articulation joint in a first motion (clockwise), a time of motor operation for a complete actuation of the articulation joint in a second motion (counter-clockwise), and a motor temperature under operation. Thus, a motor control signal may be adjusted based on the difference the operation of the motor at initial manufacture and the operation of the motor at the time after initial manufacture.

The data indicative of an operation of the motor at initial manufacture may be generated by executing a calibration sequence after full assembly of the powered stapling system. For statistical purposes, multiple calibration sequences may be run after initial manufacture, and appropriate statistics—such as mean values and standard deviation values—may be retained. The data indicative of an operation of the motor at initial manufacture may be stored in a memory device of the powered surgical stapling device, or may be accessible to the motor controller of the powered surgical stapling device over a network connection to any one or more of a surgical hub or a cloud-based networked system.

The data associated with the powered surgical stapling system immediately after manufacture may serve as a baseline against which the operation of the powered surgical stapling system may be compared. In this manner, operational degradation may be measured, and the control algorithms of the motor controller may be adjusted to compensate for the degradation. The adjustments to the control algorithms may include adjustment to control threshold values for the operation of the motor and/or the motor gear reducer assembly (such as motor current, motor voltage, or motor and/or the motor gear reducer assembly speed thresholds). Algorithms designed to adjust a pulse-width modulation (PWM) motor control signal may also be adjusted to compensate for non-use conditions.

As disclosed above, a comparison may be made between the operation of the powered surgical stapling system immediately after manufacture and at some time after manufacture. The time after manufacture may include a time after the powered surgical stapling system has been used for a predetermined number of cases. The time after manufacture may include a time of receipt of the powered surgical stapling system by a user. Additionally, initial operation data from the motor and/or motor gear reducer assembly manufacture may be obtained separately. In some aspects, the time after motor and/or motor gear reducer assembly manufacture may include the time of initial use of the powered surgical stapling system. Thus, the motor controller may receive initial manufacture motor and gear reducer assembly characteristic data from a manufacturer. The motor controller may then receive operational motor and gear reducer assembly data during an initial use of the powered surgical stapling system. The algorithms in the motor controller used to control the operation of the motor may then adjust one or more parameters of a motor control signal based on a comparison of between the initial manufacture motor and gear reducer assembly characteristic data and the operational motor and gear reducer assembly data during the initial use of the powered surgical stapling system. In certain aspects, the adjustment is based on a difference between the initial manufacture motor and gear reducer assembly characteristic data and the operational motor and gear reducer assembly data during the initial use of the powered surgical stapling system.

Figure 26:
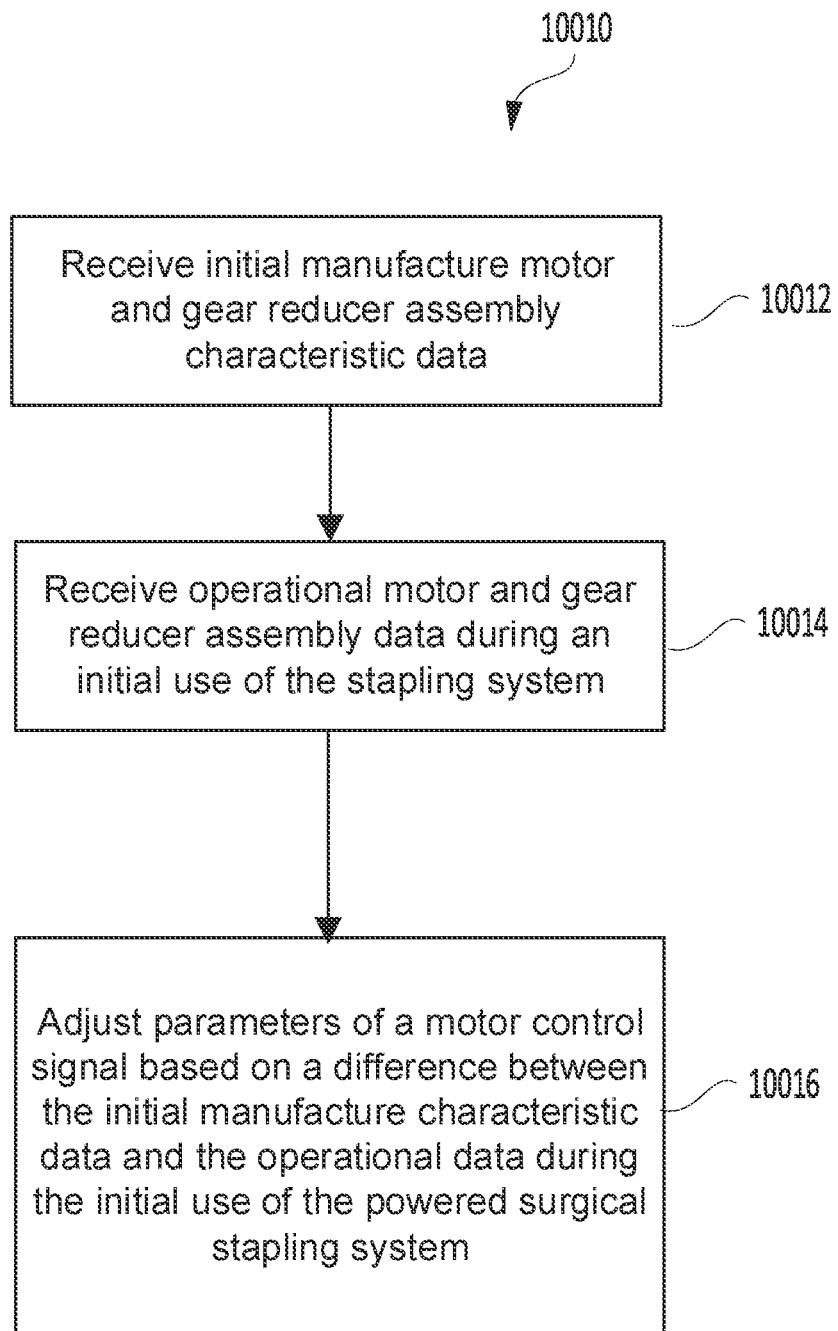
FIG. 26 is a flow chart of a method of adjusting parameters of a motor control signal based on differences between initial manufacture data and initial use data according to one aspect of this disclosure.

A method of adjusting an operation of a motor and/or a motor gear reducer assembly is depicted in flow chart 10010 in FIG. 26. Thus the motor controller may receive 10012 initial manufacturer motor and gear reducer assembly characteristic data from a manufacturer. The motor controller may receive 10014 operational motor and gear reducer assembly data during an initial use of the powered surgical stapling system. The motor controller may then adjust 10016 parameters of a motor control signal based on a difference between the initial manufacture motor and gear reducer assembly characteristic data and the operational motor and gear reducer assembly data during the initial use of the powered surgical stapling system.

In some aspects of the method, receiving the initial manufacture motor and gear reducer assembly characteristic data may include receiving one or more of initial motor speed data, initial motor torque data, initial gear reducer assembly torque transmission data, initial motor temperature data, or initial gear reducer assembly temperature data.

In some aspects of the method, receiving the operational motor and gear reducer assembly data during an initial use of the powered surgical stapling system may include receiving first use motor back electromagnetic force (EMF) data, first use motor temperature data, or first use gear reducer assembly temperature data.

In some aspects, the method may also include receiving, by the motor controller, initial manufacture motor and gear reducer assembly acceptance data.

In some aspects, the method may also include adjusting, by the motor controller, one or more parameters of the motor control signal based on a difference between the initial manufacture motor and gear reducer assembly acceptance data and the operational motor and gear reducer assembly data during the initial use of the powered surgical stapling system.

In some aspects of the method, adjusting one or more parameters of the motor control signal comprises adjusting one or more of a motor current maximum, a motor voltage, a PID controller parameter, a timing parameter, a motor speed or threshold step, or a motor control signal waveform.

The data received from the motor and/or motor gear reducer assembly manufacturer may be stored in non-volatile memory of the powered surgical stapling system after the data have been determined. Alternatively, the data received from the manufacturer may be shipped as a memory device—such as a flash drive—for a user to install in the powered surgical stapling system. In another alternative, the data received from the manufacturer may be accessible to the powered surgical stapling system over a computer network such as over a cloud-based computing system or through a direct connection to a server under control by the motor and/or motor gear reducer assembly manufacturer. As disclosed above, the initial data from the manufacturer may serve as a base-line for similar data obtained during or after use of the powered surgical stapling system.

The initial motor and/or motor gear reducer assembly manufacturing data may include, besides data associated with operation of a motor, data associated with a gear reducer assembly. Speed, torque, and operational temperature data may also be obtained separately for the gear reducer assembly. The operational temperature profile data for the gear reducer assembly may be overlaid with that of the equivalent motor heating, speed, and torque data to determine specific critical points. Non-concentric motor shaft issues could be discovered, which could help determine uneven rotor alignment in the motor. Additionally, motor torque variations over time may be identified, and parameters of the motor control signal algorithms may be adjusted to compensate for the variations. Additional data that may be obtained from the initial motor manufacturer may relate to motor winding variations, magnet strength of permanent magnets used in the motors, and brush/rotor contact area for DC brushed motors.

The initial temperature of motor assembly (either the motor alone or combined with the gear reducer assembly) may be used to determine initial performance characteristics of the powered surgical stapling system. An initial motor/heating transfer function may be used to better predict future motor performance. In addition to motor back EMF measurements, other current and/or voltage measurements may be obtained for either brushed or brushless DC motors. As disclosed above, the powered surgical stapling system may be usable with multiple interchangeable surgical shaft assemblies. By including the manufacturer data for both the motor and the motor gear reducer assembly, the motor control algorithm may adjust to the different shaft assemblies, thereby "normalizing" or matching the motor operations across all interchangeable shaft assemblies.

In some aspects, the initial motor and motor gear reducer assembly data may permit matching a higher performing motor with a slightly lower performing motor gear reducer assembly. In this manner, it is possible to keep the motor gear reducer assembly performance error bands narrower and minimize component scrap potential. This may permit the use of a wider range of components that under normal conditions would be scrapped.

As disclosed above, it may be useful to control component performance characteristics to normalize overall system performance outputs over a number of interchangeable shaft assemblies. In one non-limiting example, the motor and motor gear reducer assembly may undergo acceptance testing after final assembly to verify the assemblies are within performance targets. Both the motors and motor gear reducer assemblies may have target acceptance values for a normal system, including tolerance bands for minimum and maximum outputs. The target nominal performance of the motors and motor gear reducer assemblies could be affected by component tolerances and/or assembly, which may impact the drive variation in efficiencies and performance. Presently, all motors and motor gear reducer assemblies that are within the target performance tolerances can be assembled together for a final system. As an alternative matching performance of the motor to performance of the motor gear reducer assembly could drive the target output of the system to a defined target and minimize the variation of the overall system. Thus, a motor having 80% efficiency coupled to a 70% efficient motor gear reducer assembly with have an overall system efficiency of 75%. Alternatively, a motor having 70% efficient motor coupled to a 85% efficient motor gear reducer assembly would have an efficiency of 75%. Although independently the components differ in their respective efficiencies, the combination of components with the powered surgical stapling system would equalize the final output and drive for devices that have the same final output. In this manner, properly combining the motor and motor gear reducer assembly may lead to a reduction of variation between devices and performance outputs.

In some aspects, the initial manufacture data of the motors and motor gear reducer assemblies may be used as inputs to set and adjust motor control signal algorithm limits. In one non-limiting example, a manufacture may supply motor and motor gear reducer assembly acceptance data after final assembly to verify the motor assembles are within performance targets. These data could be stored onto the components by means of RFID or embedded into the cloud based on serial number. During manufacturing/assembly of the powered surgical stapling system, these data could be stored in and read by the motor controller to set various operational limits of that device. For example, the motor may have different outputs in voltage/temperature determined at a component level. The motor control algorithm could adapt to those limits for a specific powered surgical stapling system configuration to only run the algorithm within the predetermined motor operational range. Additionally the motor gear reducer assembly may have different efficiencies at different speeds. The motor gear reducer assembly acceptance data could be an input to drive the algorithm to operate at its most speed for that specific powered surgical stapling system configuration.

In the operation of various DC motors, the motor operation may be controlled by a pulse-width modulation (PWM) system. A PWM system generates a signal based on a base frequency defined by a time period in which current pulses are supplied to the motor. Each current pulse occurs over some portion of the time period and may represent any percentage of the time period from 0% (no current supplied over the time period) to 100% (current supplied over the entire time period). The speed of the motor may depend on the portion of the time period during which the current is supplied, hence the motor speed is modulated by the pulse width of the current over the time period.

Typically, the PWM base frequency is kept constant throughout the motor control sequence. However, additional tuning of motor action may be obtained by changing not only the pulse widths, but also the base frequency of the PWM system. Adaptation of the frequency of the PWM to change the motor output may improve active control of the dynamic inertia of the drive-train by shifting between two or more different operational states. The ability to make adjustments to the motor control algorithm after initial programming may be useful in intelligent surgical devices. In some operational states, the motor controller processor may run at a fixed frequency and outputting command information based on that fixed frequency. An independent system having greater processing capability, and running at a faster speed, can bring additional, more up to date information to the command signal from the processor. By merging or adapting the two signals, a more desirable signal may be generated to command the motor controller.

In one aspect, a PWM system could operate in at least two modes. In a first mode, the PWM motor control signal may drive the system in a single direction only, at a single PWM base frequency. In a second mode, the PWM motor control signal may operate at a frequency lower than the base frequency, which may cause the system to alternate between driving the motor and associated drive-train in the directed system and braking in the frictionally opposite direction. This second mode could enable a slower controlled motion of systems that use brushless motors or in systems where the gears in the gear reducer assembly may differ significantly in response as they age, as their working temperature increases, or with use. A reduction in base frequency of the PWM system may allow the motor controller to better control slower speeds and stops.

In one example, a powered surgical stapling system may clamp on a large bundle of tissue. Initially, the motor controller may supply constant power to the tissue blade drive system in order to increase its overall inertia. This may be done to ensure the necessary performance to begin cutting/stapling the tissue. During the initial part of the drive, the PWM base frequency may be increased to have more resolution in the small changes occurring to the tissue blade drive-train. These changes may be a function of both the tissue grasped in the jaw and the tissue blade drive-train. Once the tissue blade drive-train has established an initial nominal speed, the PWM frequency may be decreased for most of the remaining drive distance. Only if an operational anomaly is detected—such as a sudden increase in the tissue thickness that may affect the cutting speed—would the PWM frequency quickly increase again for finer motion control. At the end of the tissue cutting cycle, the PWM algorithm may again be adjusted when the knife stops travel. This adjustment of the PWM frequency during the complete cutting stroke operation may ensure a complete knife extension while also ensuring that the knife does not over travel at the end of the cut.

The adaptation of the PWM base frequency to operational conditions is a time based approach to modifying the interaction between the tissue blade drive-train and the tissue. By increasing the PWM signal base frequency for motors coupled to the tissue blade drive-train, the tissue would not have time to relax or react to the tissue cutting process. By slowing down the PWM signal base frequency, the motor controller may provide the tissue additional time to react or relax during the "off" cycle of the PWM.

Figure 27:
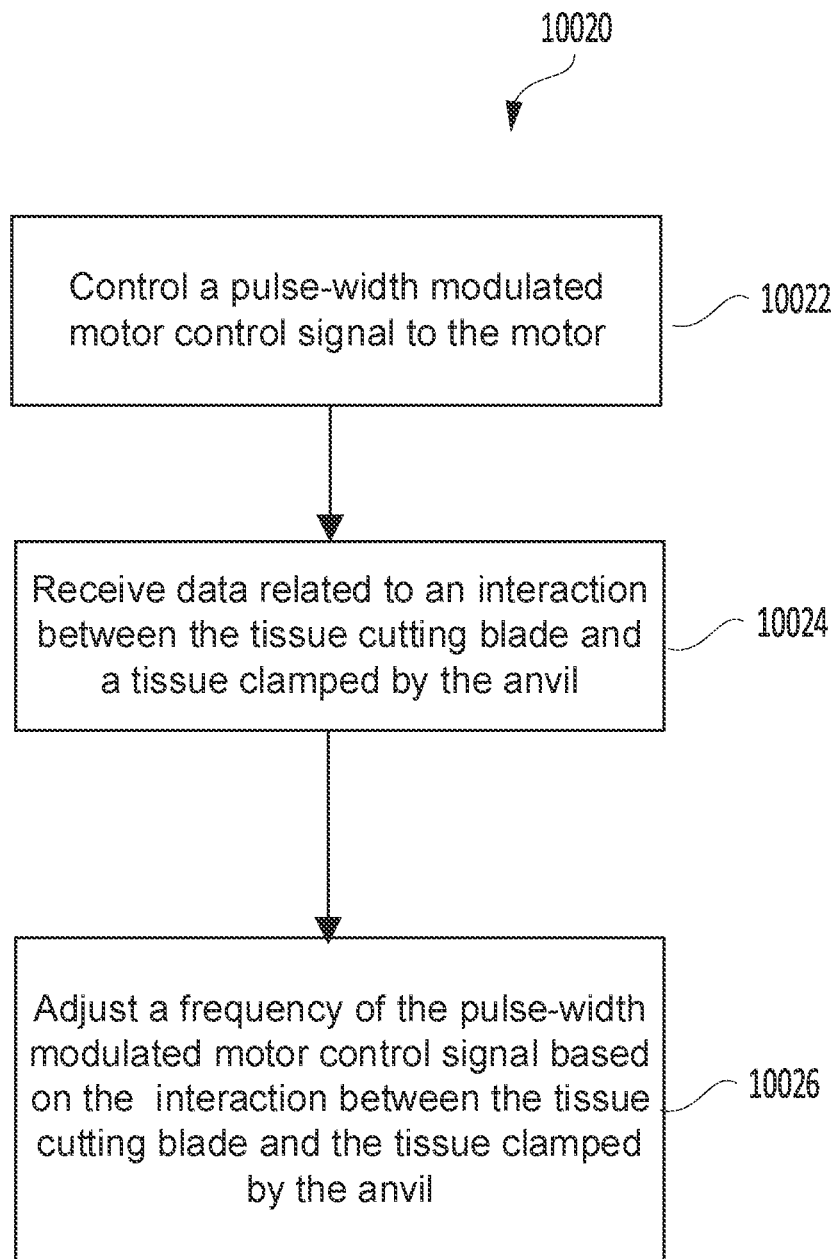
FIG. 27 is a flow chart of a method of adjusting a frequency of a pulse-width modulation motor control signal according to one aspect of this disclosure.

FIG. 27 presents a flow chart 10020 of a method for adjusting a motor and/or drive-train operation based on a change in the PWM base frequency. Thus, the motor controller may control (10022) a pulse-width modulated motor control signal to the motor. The motor controller may receive (10024) data related to an interaction between the tissue cutting blade and a tissue clamped by the anvil of the powered surgical stapling device. In one example, the data may relate to a current required to maintain a speed of the tissue cutting blade as it cuts the tissue. In another example, the data may relate to a time for the tissue cutting blade to traverse a given distance while cutting the tissue. In an alternative example, the data may relate to a change in tissue cutting blade speed when the tissue cutting blade first begins to cut the tissue. In yet another example, the data may relate to a change in tissue cutting speed when the tissue cutting blade finishes cutting the tissue and continues moving after encountering a tissue load. The motor controller may then adjust (10026) a frequency of the pulse-width modulated motor control signal based on the data related to the interaction between the tissue cutting blade and the tissue clamped by the anvil.

In one aspect, adjusting the frequency of the pulse-width modulated motor control signal includes maintaining a first frequency of the pulse-width modulated motor control signal when the tissue cutting blade makes no contact with the tissue.

In another aspect, adjusting the frequency of the pulse-width modulated motor control signal may include changing the frequency of the pulse-width modulated motor control signal between a first frequency and a second frequency. As one example, the motor controller may alternatingly drive the tissue cutting blade into the tissue at the first frequency and drive the tissue cutting blade away from the tissue at the second frequency. In another example, the tissue cutting blade may be driven at the first frequency when the tissue cutting blade first contacts the tissue and may be driven at the second frequency after the tissue cutting blade first contacts the tissue. In some examples, the second frequency may be less than the first frequency.

Various aspects of the subject matter described herein are set out in the following examples.

Example 1—A method of controlling a motor in a powered surgical stapling system, wherein the powered surgical stapling system comprises an anvil, a portion to receive surgical staples, a tissue cutting blade, the motor, a motor power supply, a drive train, and a motor controller. The method comprises applying, by the motor controller to the motor, a first motor control signal, receiving, by the motor controller, data associated with an operation of the drive train, comparing, by the motor controller, the data associated with the operation of the drive train to baseline data associated with the operation of the drive train, and applying, by the motor controller, a second motor control signal based on the comparison, wherein the second motor control signal differs from the first motor control signal in a shape of a pulse train of the first motor control signal.

Example 2—The method of Example 1, wherein receiving data associated with an operation of the drive train comprises receiving data associated with a frictional loss of the drive train, an acceleration response of the drive train, a deceleration response of the drive train, or mechanical harmonics of the drive train.

Example 3—The method of Examples 1 or 2, wherein applying the first motor control signal comprises using a delta-sigma modulation based bit-stream controller to generate the motor control signal.

Example 4—The method of any one of Examples 1-3, wherein applying the second motor control signal based on the comparison comprises adjusting a PID control parameter, triggering a delay of a dynamic braking function, changing a level or a function window around a triggering threshold, adjusting a power applied to the motor from the motor power supply, or adjusting a pulse-width modulation signal applied to the motor.

Example 5—The method of Example 4, wherein adjusting a pulse-width modulation signal applied to the motor comprises adjusting a shape of the pulse-width modulation signal rising portion, maximum amplitude portion, or falling portion.

Example 6—A method of characterizing a motor in a powered surgical stapling system, wherein the powered surgical stapling system comprises an anvil, a portion to receive surgical staples, a tissue cutting blade, the motor, a motor power supply, a gear reducer assembly, and a motor controller, the method comprising transmitting, by the motor controller to the motor, a motor perturbation signal, receiving, by the motor controller, one or more motor function parameters, determining, by the motor controller, one or more automated surgical stapler system characteristics based on the one or more motor function parameters, and, adjusting, by the motor controller, one or more functions of the motor controller.

Example 7—The method of Example 6, wherein adjusting one or more functions of the motor controller comprises adjusting a motor drive current, a motor drive pulse-width modulation phase, a motor drive frequency, or a motor drive current.

Example 8—The method of Examples 6 or 7, wherein receiving one or more motor function parameters comprises receiving a motor latency parameter, a motor frequency dependent torque parameter, or a motor current draw parameter.

Example 9—The method of any one of Examples 6-8, wherein determining one or more automated surgical stapler system characteristics comprises determining a system friction, a system inertia, a system backlash, or a system latency.

Example 10—The method of any one of Examples 6-9, wherein transmitting the motor perturbation signal comprises transmitting a step signal.

Example 11—The method of any one of Examples 6-10, further comprising transmitting, by the motor controller to the motor, a motor operational signal along with the motor perturbation signal.

Example 12—The method of any one of Examples 6-11, wherein the motor perturbation signal comprises a chirp signal.

Example 13—The method of any one of Examples 6-12, wherein the motor perturbation signal comprises a dithering signal.

Example 14—A method of controlling a stepper motor in a powered surgical stapling system, wherein the powered surgical stapling system comprises an anvil, a portion to receive surgical staples, a tissue cutting blade, the stepper motor, a drive train mechanically coupled to the stepper motor, a stepper motor power supply, and a stepper motor controller, the method comprising applying, by the stepper motor controller to the stepper motor, a motor control signal, receiving, by the stepper motor controller, data associated with an operation of the stepper motor coupled to the drive train, comparing, by the stepper motor controller, the data associated with the operation of the stepper motor coupled to the drive train to baseline data associated with an operation of an uncoupled stepper motor, and adjusting, by the motor controller, the motor control signal based on the comparison.

Example 15—The method of Example 14, wherein comparing the data associated with the operation of the stepper motor coupled to the drive train to baseline data associated with an operation of an uncoupled stepper motor comprises comparing the data associated with the operations of the stepper motor coupled to the drive train to one or more of a motor pull-in torque, a motor pull-out torque, or a motor holding torque of the uncoupled stepper motor.

Example 16—A method of controlling a motor in a powered surgical stapling system, wherein the powered surgical stapling system comprises an anvil, an anvil clamping trigger, the motor, a gear reducer assembly, a drive bar, and a motor controller, the method comprising receiving, by the motor controller, rotational data from a first rotational sensor affixed to a shaft of the motor, receiving, by the motor controller, gear rotation data from a second rotational sensor affixed to an output shaft of the gear reducer assembly, calculating, by the motor controller, a mechanical transfer function based at least in part on the rotational data and the gear rotation data, determining, by the motor controller, mechanical system non-idealities of the powered surgical stapling system, and modifying, by the motor controller, a motor control signal based on the determined mechanical system non-idealities.

Example 17—The method of Example 16, wherein modifying the motor control signal comprises modifying one or more of a motor control signal voltage, a motor control signal current, and a motor control pulse duty cycle.

Example 18—The method of Examples 16 or 17, further comprising determining, by the motor controller, a motor response latency.

Example 19—The method of any one of Examples 16-18, further comprising determining, by the motor controller, one or more of a gear backlash, a gear slop, gear clearance, and a gear mechanical loss of the gear reducer assembly.

Example 20—The method of any one of Examples 16-19 further comprising receiving, by the motor controller, linear motion data from a sensor of a linear position of the drive bar, and calculating, by the controller, a second mechanical transfer function based at least in part on the rotational data, the gear rotation data, and the linear motion data.

Example 21—The method of any one of Examples 16-20 further comprising receiving, by the controller, trigger motion data from a motion sensor in mechanical communication with the anvil clamping trigger, receiving, by the controller, anvil position data from an anvil position sensor; and determining, by the controller, a time delay between a motion of the anvil clamping trigger and a motion of the anvil.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail, and is incorporated herein by reference in its entirety.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in one or more aspects of the present disclosure, a microcontroller may generally comprise a memory and a microprocessor ("processor") operationally coupled to the memory. The processor may control a motor driver circuit generally utilized to control the position and velocity of a motor, for example. In certain instances, the processor can signal the motor driver to stop and/or disable the motor, for example. In certain instances, the microcontroller may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available for the product datasheet.

It should be understood that the term processor as used herein includes any suitable microprocessor, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In at least one instance, the processor may be any single core or multicore processor such as those known under the trade name ARM Cortex by Texas Instruments. Nevertheless, other suitable substitutes for microcontrollers and safety processor may be employed, without limitation.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

Various instruments, tools, hubs, devices and/or systems, in accordance with the present disclosure, may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

One or more motor assemblies, as described herein, employ one or more electric motors. In various forms, the electric motors may be a DC brushed driving motor, for example. In other arrangements, the motor may include a brushless motor, a cordless motor, a synchronous motor, a stepper motor, or any other suitable electric motor. The electric motors may be powered by a power source that in one form may comprise a removable power pack. Batteries may each comprise, for example, a Lithium Ion ("LI") or other suitable battery. The electric motors can include rotatable shafts that operably interface with gear reducer assemblies, for example. In certain instances, a voltage polarity provided by the power source can operate an electric motor in a clockwise direction wherein the voltage polarity applied to the electric motor by the battery can be reversed in order to operate the electric motor in a counter-clockwise direction. In various aspects, a microcontroller controls the electric motor through a motor driver via a pulse width modulated control signal. The motor driver can be configured to adjust the speed of the electric motor either in clockwise or counter-clockwise direction. The motor driver is also configured to switch between a plurality of operational modes which include an electronic motor braking mode, a constant speed mode, an electronic clutching mode, and a controlled current activation mode. In electronic braking mode, two terminal of the drive motor are shorted and the generated back EMF counteracts the rotation of the electric motor allowing for faster stopping and greater positional precision.

As used in any aspect herein, a wireless transmission such as, for example, a wireless communication or a wireless transfer of a data signal can be achieved, by a device including one or more transceivers. The transceivers may include, but are not limited to cellular modems, wireless mesh network transceivers, Wi-Fi® transceivers, low power wide area (LPWA) transceivers, and/or near field communications transceivers (NFC). The device may include or may be configured to communicate with a mobile telephone, a sensor system (e.g., environmental, position, motion, etc.) and/or a sensor network (wired and/or wireless), a computing system (e.g., a server, a workstation computer, a desktop computer, a laptop computer, a tablet computer (e.g., iPad®, GalaxyTab® and the like), an ultraportable computer, an ultramobile computer, a netbook computer and/or a subnotebook computer; etc. In at least one aspect of the present disclosure, one of the devices may be a coordinator node.

The transceivers may be configured to receive serial transmit data via respective universal asynchronous receiver-transmitters (UARTs) from a processor to modulate the serial transmit data onto an RF carrier to produce a transmit RF signal and to transmit the transmit RF signal via respective antennas. The transceiver(s) can be further configured to receive a receive RF signal via respective antennas that includes an RF carrier modulated with serial receive data, to demodulate the receive RF signal to extract the serial receive data and to provide the serial receive data to respective UARTs for provision to the processor. Each RF signal has an associated carrier frequency and an associated channel bandwidth. The channel bandwidth is associated with the carrier frequency, the transmit data and/or the receive data. Each RF carrier frequency and channel bandwidth is related to the operating frequency range(s) of the transceiver(s). Each channel bandwidth is further related to the wireless communication standard and/or protocol with which the transceiver(s) may comply. In other words, each transceiver may correspond to an implementation of a selected wireless communication standard and/or protocol, e.g., IEEE 802.11 a/b/g/n for Wi-Fi® and/or IEEE 802.15.4 for wireless mesh networks using Zigbee routing.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

In this specification, unless otherwise indicated, terms "about" or "approximately" as used in the present disclosure, unless otherwise specified, means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

In this specification, unless otherwise indicated, all numerical parameters are to be understood as being prefaced and modified in all instances by the term "about," in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Also, all ranges recited herein are inclusive of the end points of the recited ranges. For example, a range of "1 to 10" includes the end points 1 and 10. Any maximum numerical limitation recited in this specification is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material. In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A method of controlling a motor in a powered surgical stapling system, wherein the powered surgical stapling system comprises an anvil, a portion to receive surgical staples, a tissue cutting blade, the motor, a motor power supply, a drive train, and a motor controller, the method comprising:

applying, by the motor controller to the motor, a first motor control signal;

receiving, by the motor controller, data associated with an operation of the drive train;

comparing, by the motor controller, the data associated with the operation of the drive train to baseline data associated with the operation of the drive train; and applying, by the motor controller, a second motor control signal based on the comparison, wherein the second motor control signal differs from the first motor control signal in a shape of a pulse train of the first motor control signal, wherein applying the second motor control signal based on the comparison comprises adjusting a PID control parameter, triggering a delay of a dynamic braking function, changing a level or a function window around a triggering threshold, adjusting a power applied to the motor from the motor power supply, or adjusting a pulse-width modulation signal applied to the motor.

2. The method of claim 1, wherein receiving data associated with an operation of the drive train comprises receiving data associated with a frictional loss of the drive train, an acceleration response of the drive train, a deceleration response of the drive train, or mechanical harmonics of the drive train.

3. The method of claim 1, wherein applying the first motor control signal comprises using a delta-sigma modulation based bit-stream controller to generate the motor control signal.

4. The method of claim 1, wherein adjusting a pulse-width modulation signal applied to the motor comprises adjusting a shape of the pulse-width modulation signal rising portion, maximum amplitude portion, or falling portion.

5. A method of characterizing a motor in a powered surgical stapling system, wherein the powered surgical stapling system comprises an anvil, a portion to receive surgical staples, a tissue cutting blade, the motor, a motor power supply, a gear reducer assembly, and a motor controller, the method comprising:

transmitting, by the motor controller to the motor, a motor perturbation signal, wherein the motor perturbation signal comprises a chirp signal or a dithering signal;

receiving, by the motor controller, one or more motor function parameters;

determining, by the motor controller, one or more automated surgical stapler system characteristics based on the one or more motor function parameters; and, adjusting, by the motor controller, one or more functions of the motor controller.

6. The method of claim 5, wherein adjusting one or more functions of the motor controller comprises adjusting a motor drive current, a motor drive pulse-width modulation phase, a motor drive frequency, or a motor drive current.

7. The method of claim 5, wherein receiving one or more motor function parameters comprises receiving a motor latency parameter, a motor frequency dependent torque parameter, or a motor current draw parameter.

8. The method of claim 5, wherein determining one or more automated surgical stapler system characteristics comprises determining a system friction, a system inertia, a system backlash, or a system latency.

9. The method of claim 5, wherein transmitting the motor perturbation signal comprises transmitting a step signal.

10. The method of claim 5, further comprising transmitting, by the motor controller to the motor, a motor operational signal along with the motor perturbation signal.

11. A method of controlling a stepper motor in a powered surgical stapling system, wherein the powered surgical stapling system comprises an anvil, a portion to receive surgical staples, a tissue cutting blade, the stepper motor, a drive train mechanically coupled to the stepper motor, a stepper motor power supply, and a stepper motor controller, the method comprising:

applying, by the stepper motor controller to the stepper motor, a motor control signal;

receiving, by the stepper motor controller, data associated with an operation of the stepper motor coupled to the drive train;

comparing, by the stepper motor controller, the data associated with the operation of the stepper motor coupled to the drive train to baseline data associated with an operation of an uncoupled stepper motor, wherein the baseline data associated with an operation of an uncoupled stepper motor comprises one or more of a motor pull-in torque, a motor pull-out torque, or a motor holding torque of the uncoupled stepper motor; and adjusting, by the motor controller, the motor control signal based on the comparison.

12. A method of controlling a motor in a powered surgical stapling system, wherein the powered surgical stapling system comprises an anvil, an anvil clamping trigger, the motor, a gear reducer assembly, a drive bar, and a motor controller, the method comprising:

receiving, by the motor controller, rotational data from a first rotational sensor affixed to a shaft of the motor;

receiving, by the motor controller, gear rotation data from a second rotational sensor affixed to an output shaft of the gear reducer assembly;

calculating, by the motor controller, a mechanical transfer function based at least in part on the rotational data and the gear rotation data;

determining, by the motor controller, mechanical system non-idealities of the powered surgical stapling system; and modifying, by the motor controller, a motor control signal based on the determined mechanical system non-idealities.

13. The method of claim 12, wherein modifying the motor control signal comprises modifying one or more of a motor control signal voltage, a motor control signal current, and a motor control pulse duty cycle.

14. The method of claim 12, further comprising determining, by the motor controller, a motor response latency.

15. The method of claim 12, further comprising determining, by the motor controller, one or more of a gear backlash, a gear slop, gear clearance, and a gear mechanical loss of the gear reducer assembly.

16. The method of claim 12 further comprising:

receiving, by the motor controller, linear motion data from a sensor of a linear position of the drive bar; and calculating, by the controller, a second mechanical transfer function based at least in part on the rotational data, the gear rotation data, and the linear motion data.

17. The method of claim 12 further comprising:

receiving, by the controller, trigger motion data from a motion sensor in mechanical communication with the anvil clamping trigger;

receiving, by the controller, anvil position data from an anvil position sensor; and determining, by the controller, a time delay between a motion of the anvil clamping trigger and a motion of the anvil.

* * * * *